US012268977B2

(12) United States Patent
Polasek

(10) Patent No.: US 12,268,977 B2
(45) Date of Patent: Apr. 8, 2025

(54) COMPOUNDS FOR SEPARATION OF RARE EARTH ELEMENTS AND S-, P-, D-METALS, METHOD OF SEPARATION, AND USE THEREOF

(71) Applicant: USTAV ORGANICKE CHEMIE A BIOCHEMIE AV CR, V.V.I., Prague (CZ)

(72) Inventor: Miloslav Polasek, Prague (CZ)

(73) Assignee: USTAV ORGANICKE CHEMIE A BIOCHEMIE AV CR. V.V.I., Prague (CZ)

(*) Notice: Subject to any disclaimer, the term of this patent is extended or adjusted under 35 U.S.C. 154(b) by 181 days.

(21) Appl. No.: 16/768,169

(22) PCT Filed: Nov. 30, 2018

(86) PCT No.: PCT/EP2018/083215
§ 371 (c)(1),
(2) Date: May 29, 2020

(87) PCT Pub. No.: WO2019/106182
PCT Pub. Date: Jun. 6, 2019

(65) Prior Publication Data
US 2020/0282331 A1  Sep. 10, 2020

(30) Foreign Application Priority Data
Dec. 1, 2017  (EP) .................... 17204972

(51) Int. Cl.
*B01D 15/08* (2006.01)
*C07D 401/06* (2006.01)
*C22B 59/00* (2006.01)

(52) U.S. Cl.
CPC .......... *B01D 15/08* (2013.01); *C07D 401/06* (2013.01); *C22B 59/00* (2013.01)

(58) Field of Classification Search
CPC ........ B01D 15/08; C07D 401/06; C22B 59/00
See application file for complete search history.

(56) References Cited

U.S. PATENT DOCUMENTS 5,756,065 A    5/1998 Wilson et al.
5,910,300 A *  6/1999 Tournier ............. B82Y 5/00
                                                424/9.34

FOREIGN PATENT DOCUMENTS

WO    WO-94/26275 A1    11/1994
WO    WO-95/01346 A1     1/1995

OTHER PUBLICATIONS

Hanaoka et al. J. Am. Chem. Soc. 2007, 129, 13502-13509. (Year: 2007).*
Hanaoka et al. J. Am. Chem. Soc. 2007, 129 (Supp), S1-S25. (Year: 2007).*
Sarzanini J. Chromatogr. A, 850, 1999, 213-228. (Year: 1999).*
Thompson et al. Inorg. Chem. 3(7), 1964, 1015-1018. (Year: 1964).*
Funasaka et al. J. Phys. Chem. 1995, 99, 1826-1830. (Year: 1995).*
Polasek et al. Inorg. Chem. 2009, 48, 1-11. (Year: 2009).*
Vanek et al. J. Luminescence 2012, 132, 2030-2035. (Year: 2012).*
Baek, Ah Rum et al: "Gadolinium Complex of 1,4,7, 1 O-Tetraazacyclododecane-1 ,4, 7-trisacetic Acid ( DO3A)-Ethoxybenzyl (EOB) Conjugate as a New Macrocyclic Hepatobiliary MRI Contrast Agent", J.of Med. Chem., vol. 60, No. 12, May 31, 2017, p. 4861-4868, XP55448653, ISSN: 0022-2623, DOI: 10.1021/acs.jmedchem.7b00060.
Beeby A et al: "Intramolecular Sensitisation Of Lanthanide(Iii) Luminescence by Acetophenone-Containing Ligands: the Critical Effect of Para-Substitutents and Solvent", Journal of the Chemical Society, Dal Ton Transactions, Jan. 1, 2002, pp. 48-54, XP001147821, ISSN: 1472-7773, DOI: 10.1039/B105966C.
Dietz M. L. et al.; "Applications of Extraction Chromatography in the Development of Radionuclide Generator Systems for Nuclear Medicine", (2000), Ind. Eng. Chem. Res. 39(9), 3181-3188.
Harvey, P. et al. "Moving the goal posts: enhancing the sensitivity of PARASHIFT proton magnetic resonance imaging and spectroscopy", (2013), Chem. Sci., 4(11), 4251-4258.

(Continued)

*Primary Examiner* — Johann R Richter
*Assistant Examiner* — Sean R Donohue
(74) *Attorney, Agent, or Firm* — Foley & Lardner LLP

(57) ABSTRACT

The present invention relates to compounds of general formula (I) for chromatographic separation of rare earth elements and/or s-, p-, d-metals, as well as to the method of the separation of rare earth elements.

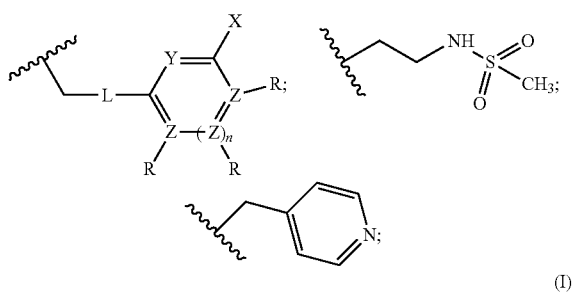

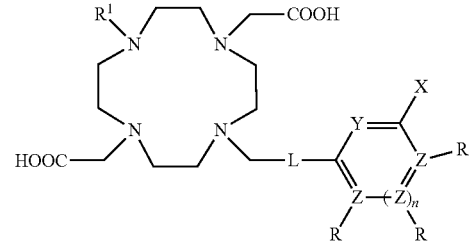

(I)

18 Claims, 3 Drawing Sheets

(56) References Cited

OTHER PUBLICATIONS

International Search Report and Written Opinion in PCT/EP2018/083215, dated Jan. 22, 2019 (15 pages).
Kifle, D. et al., "Selective liquid chromatographic separation of yttrium from heavier rare earth elements using acetic acid as a novel eluent", G. (2013), J. Chromatogr. A 1307, 86-90.
Kifle, D. et al: "Selective liquid chromatographic separation of yttrium from heavier rare earth elements using acetic acid as a novel eluent", Journal of Chromatography A, vol. 1307, pp. 86-90, XP028693363.
Liao, Z. et al: "Spectrally resolved confocal microscopy using lanthanide centred near-IR emission", Chemical Communications, vol. 51, No. 12, Jan. 1, 2015, p. 2372-2375, XP055448444.
Liu, Wei-Min et al: "A Two-Armed Lanthanoid-Chelating Paramagnetic NMR Probe Linked to Proteins via Thioether Linkages", Chemistry—A European Journal, vol. 20, No. 21, Apr. 15, 2014, p. 6256-6258, XP055540223.
Martins et al: "A Bis(pyridine N-oxide) Analogue of DOTA: Relaxometric Properties of the Gd III Complex and Efficient Sensitization of Visible and NIR-Emitting Lanthanide(III) Cations Including Pr III and Ho III", Chemistry—A European Journal, vol. 20, No. 45, Nov. 3, 2014, p. 14834-14845, XP055540209.
Medvedev D. G. et al. "Development of a large scale production of 67Cu from 68Zn at the high energy proton accelerator: Closing the 68Zn cycle", (2012), Appl. Radiat. Isot. 70(3), 423-429.
Mizukami. S. et al: "Lanthanide-Based Protease Activity Sensors for Time-Resolved Fluorescence Measurements", Journal of the American Chemical Society, vol. 130, No. 44, Nov. 5, 2008, pp. 14376-14377, XP055448437.
Nayak D. et al. "Separation of the Carrier Free Radioisotopes of Lanthanide Series Elements", (1999), Solvent Extr. Ion Exch. 17(5), 1133-1154.
Ogan MD et al: "A Specific Radioimmunoassay for the Measurement Of Gadoteridol, a Contrast Agent for Magnetic Resonance Imaging in Biological Fluids", J.of Pharma. Sciences, vol. 82, No. 5, May 1, 1993, p. 475-479, XP001119429, ISSN: 0022-3549, DOI: 10.1002/JPS.2600820509.
Polasek M. et al. "PAMAM Dendrimers Conjugated with an Uncharged Gadolinium(III) Chelate with a Fast Water Exchange: The Influence of Chelate Charge on Rotational Dynamics", (2009), Bioconjugate Chem. 20(11), 2142-2153.
Polasek M. et al. "Pyridine-N-oxide Analogues of DOTA and Their Gadolinium(III) Complexes Endowed with a Fast Water Exchange on the Square-Antiprismatic Isomer", (2009), Inorg. Chem. 48(2), 455-465.
Quici, S. et al: "Highly Photoluminescent Silica Layers Doped with Efficient Eu(III) and Tb(III) Antenna Complexes", Chemistry of Materials, vol. 21, No. 13, Jul. 14, 2009, p. 2941-2949, XP055448439.
Regueiro-Figueroa, M. et al: "Lanthanide dota-like Complexes Containing a Picolinate Pendant: Structural Entry for the Design of Ln III -Based Luminescent Probes", Inorganic Chemistry, vol. 50, No. 9, May 2, 2011, p. 4125-4141, XP055448649.
Routledge, J. et al: "Kinetically Stable Lanthanide Complexes Displaying Exceptionally High Quantum Yields upon Long-Wavelength Excitation: Synthesis, Photophysical Properties, and Solution Speciation", Inorganic Chemistry, vol. 54, No. 7, Apr. 6, 2015, pp. 3337-3345, XP055448333.
Routledge, J. et al: "Lanthanide Complexes that Respond to Changes in Cyanide Concentration in Water", Angewandte Chemie International Edition, vol. 56, No. 27, Jun. 5, 2017, pp. 7783-7786,XP055448460.
Schwantes, J. M. et al. "Preparation of a one-curie 171Tm target for the detector for advanced neutron capture experiments (DANCE)", (2008) J. Radioanal. Nucl. Chem. 276(2), 533-542.
Ung, P. et al: "Extending the Excitation Wavelength of Potential Photosensitizers via Appendage of a Kinetically Stable Terbium(III) Macrocyclic Complex for Applications in Photodynamic Therapy", Inorganic Chemistry, vol. 56, No. 14, Jul. 6, 2017, p. 7960-7974, XP055448463, ISSN: 0020-1669, DOI: 10.1021 /acs.inorgchem.7b00677.
Xie, F. et al. "A critical review on solvent extraction of rare earths from aqueous Solutions", (2014), Miner. Eng. 56, 10-28.
Xie, F. et al: "A critical review on solvent extraction of rare earths from aqueous solutions", Minerals Engineering., vol. 56, Feb. 1, 2014, pp. 10-28, XP055304805.
Gempf, K et al "Direct and selective tagging of cysteine residues inpeptides and proteins with 4-nitropyridyl lanthanide complexes", Chem. Commun., 2013,49, 9104-9106.
Martin Regueiro-Figueroa et al "Highly Stable Complexes of Divalent Metal Ions (Mg2 ,Ca2 , Cu2 , Zn2 , Cd2 , and Pb2 ) with a Dota-Like Ligand Containing a Picolinate Pendant", Eur. J. Inorg. Chem. 2014, 6165-6173.

* cited by examiner

COMPOUNDS FOR SEPARATION OF RARE EARTH ELEMENTS AND S-, P-, D-METALS, METHOD OF SEPARATION, AND USE THEREOF

CROSS-REFERENCE TO RELATED APPLICATIONS

This application is a U.S. National Phase Application under 35 U.S.C. § 371 of International Application No. PCT/EP2018/083215, filed on Nov. 30, 2018, which claims the benefit of priority to EP Application Serial No. 17204972.8, filed on Dec. 1, 2017, the contents of each of which are herein incorporated by reference.

TECHNICAL FIELD

This invention relates to compounds suitable for separation of rare earth elements and/or s-, p-, d-block metals, a method of chromatographic separation of rare earth elements and/or s-, p-, d-block metals from a mixture of metal ions, at least one of them being a rare earth metal selected from Ce, Dy, Er, Eu, Gd, Ho, La, Lu, Nd, Pr, Pm, Sm, Sc, Tb, Tm, Yb and Y, alkaline earth metal, Al, Ga, In, Tl, Sn, Pb or transitional metal, and use thereof for extraction and separation of rare earth metals and/or s-, p-, d-block metals from mixtures.

BACKGROUND ART

Radionuclides of metal elements are increasingly used in nuclear medicine, mainly for diagnosis and therapy of oncological diseases. There is a growing interest in targeted radiotherapy that uses a targeting vector (peptide, antibody, etc.) to deliver the radioactive payload specifically to cancer tissue. Radionuclides of metal elements are advantageous because the connection to the targeting vector can be conveniently achieved through coordination to a bifunctional chelator.

To reduce the possibility of unwanted toxicity and to maximize efficiency of the treatment, radionuclides for medical applications are preferred in a so-called "no-carrier-added" (NCA) form, i.e. containing no unnecessary matter. However, achieving this extremely high purity of metal radionuclides is a major challenge. Most commonly, medical radionuclides are prepared from a stable nuclide by a particle-induced nuclear reaction. Preparation of NCA radionuclide requires complete removal of the parent nuclide and byproducts, both usually present in several orders of magnitude larger quantities. Contamination with trace metals from solvents, chemicals and equipment must be strictly avoided. Furthermore, handling radioactivity brings many technical difficulties. Common separation methods are either not practical for work with radioactivity or not efficient enough to provide NCA radionuclides. New separation methods specifically designed for metal radionuclides are needed.

Rare earth elements (scandium—Sc, yttrium—Y, lanthanum—La, cerium—Ce, praseodymium—Pr, neodymium—Nd, promethium—Pm, samarium—Sm, europium—Eu, gadolinium—Gd, terbium—Tb, dysprosium—Dy, holmium—Ho, erbium—Er, thulium—Tm, ytterbium—Yb and lutetium—Lu) are a group of metals that offer a broad choice of radionuclides for medical applications. Radionuclides $^{90}$Y and $^{153}$Sm are approved by FDA, clinical trials are ongoing with $^{166}$Ho and $^{177}$Lu, and others show advantageous properties ($^{44}$Sc, $^{47}$Sc, $^{86}$Y, $^{149}$Pm, $^{159}$Gd, $^{149}$Tb, $^{161}$Tb, $^{165}$Dy, $^{161}$Ho, $^{169}$Er and $^{175}$Yb). These metals are chemically similar, providing the advantage that the same targeting vector, bioconjugation and labelling chemistry can be used with any member of the group. However, obtaining these radionuclides as NCA is notoriously difficult, as it usually requires separation of two neighboring rare earth elements with extremely similar properties.

The techniques so far applied to separation of rare earth radionuclides are ion exchange chromatography, extraction chromatography and liquid-liquid extraction (Nayak D., Lahiri S. (1999), *Solvent Extr. Ion Exch.* 17(5), 1133-1154). These techniques take advantage of small differences in the ionic radii that almost linearly decrease from La$^{3+}$ to Lu$^{3+}$. The ionic radius influences basicity and steric demands of the ions, properties that are used in the separation process. A common feature of these separation techniques is that the rare earth ion is involved in relatively weak interactions that allow rapid exchange of its immediate surrounding. These interactions include ionic interactions, solvation and coordination. As the molecular interactions are repeated many times during the exchange process, even small differences in properties between the metal ions are amplified, ultimately leading to separation. It is important to note that the coordinating ligands used in these techniques provide kinetically labile complexes with the rare earth ions to allow the exchange. Typical examples of such ligands are di-(2-ethylhexyl)phosphoric acid (HDEHP) and α-hydroxyisobutyric acid (α-HIBA) (Xie, F. et al. (2014), *Miner. Eng.* 56, 10-28). Strongly chelating ligands such as those derived from 1,4,7,10-tetraazacyclododecane (cyclen) are not used, because these provide kinetically inert complexes that do not permit the exchange (a typical example of such strong chelators is 1,4,7,10-tetraazacyclododecane-1,4,7,10-tetraacetic acid (DOTA)).

There are also alternative separation techniques that take advantage of more exotic oxidation states (other than 3+) of rare earth elements, but these are limited to the very few cases where such oxidation states are possible (Nayak D., Lahiri S. (1999), *Solvent Extr. Ion Exch.* 17(5), 1133-1154).

The techniques for separation of radionuclides of s-, p- and d-block metals are similar to those mentioned above for rare earth elements. Most commonly used are ion exchange chromatography, extraction chromatography and liquid-liquid extraction (Dietz M. L., Horwitz E. P. (2000), *Ind. Eng. Chem. Res.* 39(9), 3181-3188). Less commonly also precipitation, distillation and electrochemical deposition. Typically, no single technique can provide satisfactory result and a combination of techniques must be used, with ion exchange chromatography or extraction chromatography as the last step (Medvedev D. G. et al. (2012), *Appl. Radiat. Isot.* 70(3), 423-429). The use of a single technique for the separation greatly simplifies the overall process and is highly desired. Also for these metals, strongly chelating ligands such as those derived from 1,4,7,10-tetraazacyclododecane (cyclen) are not used.

The need for an effective and fast separation of rare earth elements and s-, p- and d-block metals therefore remains.

DISCLOSURE OF THE INVENTION

Even though the state of the art teaches away from use of strong chelators for rare earth elements separation, surprisingly we have found that certain strong chelators are extremely efficient in such separations, and, moreover, they can also be used for s-, p-, d-block metals separations. s-, p-, d-metals are defined as metals belonging into groups II.A (alkaline earth metals), III.A (Al, Ga, In, Tl) and IV.A (Sn, Pb) and transitional metals (I.B to VIII.B group). The present invention relates to new types of chelators structurally derived from cyclen, and to a method of their use for separation of rare earth elements and/or s-, p-, d-block metals. The principle of separation is notably different from the abovementioned existing separation techniques, and provides simplified (and therefore faster) manipulation with rare earth and/or s-, p-, d-block metal radionuclides in solution, their processing and purification. The speed and simplicity of the method is crucial for manipulation with radionuclides, which undergo the radioactive decay. When bound to rare earth ions and/or s-, p-, d-block metals, the chelators of the present invention respond to even very small differences in the ionic radii of the metals by pronounced differences in polarity of the respective resulting chelates. Because of the varying polarity, the chelates can be separated by conventional chromatography on normal or reversed phase. The metals are thus separated in the form of chelates. Importantly, the chelators disclosed in this invention form chelates that are kinetically inert on the time-scale of the separation process. The kinetic inertness effectively protects the radionuclide from additional contamination with other metals, as the radionuclide cannot escape from the chelate nor can it be replaced by another metal ion during the chromatography. Importantly, this property allows using conventional chromatographic columns and instrumentation that consist of metal parts. The separation method of the present invention can be used to separate rare earth elements regardless of the particular isotopes of the involved elements.

The subject of the present invention is the use of compounds of general formula (I)

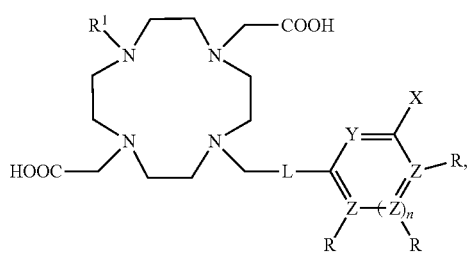

(I)

wherein
X is selected from a group consisting of H; OH; SH; $CF_3$; F; Cl; Br; I; $C_1$ to $C_6$ alkyl; $C_1$ to $C_6$ alkyloxy; $C_1$ to $C_6$ alkylthio; $NH_2$; $C_1$ to $C_6$ alkylamino; di($C_1$ to $C_6$ alkyl)amino; $NO_2$; COOH;
Y is selected from a group consisting of nitrogen; carbon, which can optionally be substituted with OH or F; oxygen; N-oxide ($N^+$—$O^-$);
Z atoms are independently selected from the group consisting of carbon and nitrogen, wherein R is only present when the valence of Z allows it; and wherein at least one Z is carbon; and wherein n=0 or 1;
L is covalent bond or —C(O)—;
R are independently selected from the group consisting of H; $C_1$ to $C_6$ alkyl; $C_1$ to $C_6$ alkyloxy; $C_6$ to $C_{10}$ aryloxy; benzyloxy; $C_1$ to $C_6$ alkylthio; $C_6$ to $C_{10}$ arylthio; F; Cl; Br; I; OH; SH; $NH_2$; $C_1$ to $C_6$ alkylamino; di($C_1$ to $C_6$ alkyl)amino; $C_1$ to $C_6$ acylamino; di($C_1$ to $C_6$ acyl)amino; $C_6$ to $C_{10}$ arylamino; di($C_6$ to $C_{10}$ aryl)amino; CN; OH; nitro; $COOR_n$, $C(O)NHR_n$, $C(O)N(R_n)_2$, wherein $R_n$ is independently H or $C_1$ to $C_{10}$ alkyl or $C_6$ to $C_{10}$ aryl; or neighboring two R together with neighboring two Z form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl; or X and the neighboring carbon, Z and R together form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl;

$R^1$ is selected from the group consisting of H; —($C_1$ to $C_6$ alkyl); benzyl, which can be optionally substituted independently with one or more substituents selected from nitro, OH; —($C_1$ to $C_2$ alkylen)COOH, the alkylen of which can optionally be substituted with $C_1$ to $C_6$ alkyl; —$CH_2P(O)(OH)_2$; —$CH_2P(O)(OH)(C_1$ to $C_6$ alkyl);

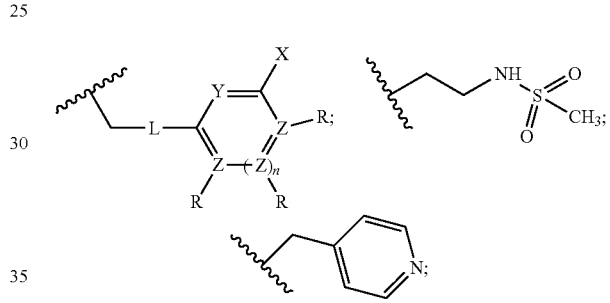

for chromatographic separation of rare earth elements and/or s-, p- and d-block metals.

Rare earth elements are cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb) and yttrium (Y). s-, p- and d-block metals are preferably II.A, III.A, IV.A, V.A metals and transitional metals, more preferably II.A, III.A (Al, Ga, In, Tl), IV.A (Sn, Pb), V.A (Bi), I.B, II.B, and VIII. B group metals, most preferably selected from $Ca^{2+}$, $Fe^{2+}$, $Fe^{3+}$, $Co^{2+}$, $Ni^{2+}$, $Cu^{2+}$, $Zn^{2+}$, $Al^{3+}$, $Pb^{2+}$, $Bi^{3+}$.

The general formula (I) of the present invention is meant to include all isomers, enantiomers and diastereoisomers.

In one preferred embodiment, the use according to the present invention relates to chromatographic separation of rare earth elements.

In one preferred embodiment, the use according to the present invention relates to chromatographic separation of s-, p- and d-block metals, selected from groups II.A, III.A, IV.A, V.A, transitional metals (such as I.B, II.B, and VIII. B), preferably selected from $Ca^{2+}$, $Fe^{2+}$, $Fe^{3+}$, $Co^{2+}$, $Ni^{2+}$, $Cu^{2+}$, $Zn^{2+}$, $Al^{3+}$, $Pb^{2+}$, $Bi^{3+}$.

Preferably, at most one Z is other than carbon in each ring of the general formula (I), containing Z atoms. Preferably, the ring containing Z atoms is selected from pyridine, pyrimidine, pyrrole, imidazole, indole, isoquinoline, quinoline, pyrazine, pyridine N-oxide, quinoline N-oxide, isoquinoline N-oxide, benzene, naphtalene, furan, hydroxyquinoline; more preferably, the ring containing Z atoms is a pyridine ring, pyridine N-oxide ring, quinoline N-oxide, isoquinoline N-oxide or benzene ring.

Preferably, X is H, F, Cl, Br, I, $CH_3$, COOH.

Preferably, $R^1$ is selected from H, —$CH_2COOH$, —$CH_2CH_2COOH$, —$CH(CH_3)COOH$, —$CH_2P(O)(OH)_2$, —$CH_2P(O)(OH)(C_1$ to $C_6$ alkyl),

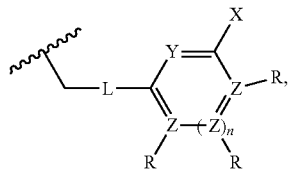

wherein L, X, Y, Z and R are independently selected and defined as above.

Preferably, L is a covalent bond.

Preferably, R is selected from H, OH, $OCH_3$, $NO_2$, F, Cl, Br, I, $CH_3$, COOH, $COOR_n$, $C(O)NHR_n$, $C(O)N(R_n)_2$, wherein R is defined as above.

In one preferred embodiment, when Y is nitrogen, all Z are carbon, and n is 1, then X is other than H, preferably X is F, Cl, Br, I, $CH_3$, $CF_3$, $OCH_3$, $SCH_3$, OH, SH, $NH_2$, $NO_2$, more preferably X is F, Cl, Br, I, $CH_3$. Substituents R, $R^1$ and L are as defined by the general formula (I).

In another preferred embodiment, when Y is nitrogen, one Z is nitrogen, and n is 1, then X is other than H, preferably X is F, Cl, Br, I, $CH_3$, $CF_3$, $OCH_3$, $SCH_3$, OH, SH, $NH_2$, $NO_2$, more preferably X is F, Cl, Br, I, $CH_3$. Substituents R, $R^1$ and L are as defined by the general formula (I).

In another preferred embodiment, when Y is N-oxide ($N^+$—$O^-$), Z is carbon, and n is 1, then X is H or X and the neighboring carbon, Z and R form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl) amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl. Substituents R, $R^1$ and L are as defined by the general formula (I).

In another preferred embodiment, when Y is carbon, as well as all Z are carbon, and n is 1, then X is H, $NH_2$, $NO_2$, and substituents R, $R^1$ and L are as defined by the general formula (I), more preferably R is OH or $C_1$ to $C_6$ alkyloxy.

In another preferred embodiment, when Y is nitrogen, all Z are carbon, and n is 1, then X is H or X and the neighboring carbon, Z and R form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl) amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl. Substituents R, $R^1$ and L are as defined by the general formula (I).

In another preferred embodiment, when Y is nitrogen, all Z are carbon, and n is 1, then X is COOH. Substituents R, $R^1$ and L are as defined by the general formula (I).

In one preferred embodiment, the compounds for use for separation of rare earth elements are selected from the group consisting of: 2,2',2''-(1-((6-fluoropyridin-2-yl)methyl)-1,4,7,10-tetraazacyclododecane-1,4,7-triyl)triacetic acid (1); 2,2',2''-(1-((6-chloropyridin-2-yl)methyl)-1,4,7,1-tetraaza- cyclododecane-1,4,7-triyl)triacetic acid (2); 2,2',2''-(10-((6-bromopyridin-2-yl)methyl)-1,4,7,10-tetraazacyclododecane-1,4,7-triyl)triacetic acid (3); 2,2',2''-(10-((6-(trifluoromethyl)pyridin-2-yl)methyl)-1,4,7,10-tetraazacyclododecane-1,4,7-triyl)triacetic acid (4); 2,2',2''-(10-((6-methoxypyridin-2-yl)methyl)-1,4,7,1-tetraazacyclododecane-1,4,7-triyl)triacetic acid (5); 2,2',2''-(10-((6-methylpyridin-2-yl)methyl)-1,4,7,1-tetraazacyclododecane-1,4,7-triyl)triacetic acid (6); 2,2',2''-(10-((4,6-dimethylpyridin-2-yl)methyl)-1,4,7,10-tetraazacyclododecane-1,4,7-triyl)triacetic acid (7); 2,2',2''-(10-(pyridin-2-ylmethyl)-1,4,7,10-tetraazacyclododecane-1,4,7-triyl)triacetic acid (8); 2,2',2''-(10-(isoquinolin-1-ylmethyl)-1,4,7,10-tetraazacyclododecane-1,4,7-triyl) triacetic acid (9); 2,2',2''-(10-(isoquinolin-3-ylmethyl)-1,4,7,10-tetraazacyclododecane-1,4,7-triyl)triacetic acid (10); 2,2',2''-(10-(quinolin-2-ylmethyl)-1,4,7,10-tetraazacyclododecane-1,4,7-triyl)triacetic acid (11); 2,2',2''-(10-((6-carboxypyridin-2-yl)methyl)-1,4,7,10-tetraazacyclododecane-1,4,7-triyl)triacetic acid (12); 2,2',2''-(10-((6-methylpyrazin-2-yl)methyl)-1,4,7,10-tetraazacyclododecane-1,4,7-triyl) triacetic acid (13); 2,2',2''-(10-(pyrazin-2-ylmethyl)-1,4,7,10-tetraazacyclododecane-1,4,7-triyl)triacetic acid (14); 4-methyl-2-((4,7,10-tris(carboxymethyl)-1,4,7,10-tetraazacyclododecan-1-yl)methyl)pyridine 1-oxide (15); 2-methyl-6-((4,7,10-tris(carboxymethyl)-1,4,7,10-tetraazacyclododecan-1-yl)methyl)pyridine 1-oxide (16); 4-carboxy-2-((4,7,10-tris(carboxymethyl)-1,4,7,10-tetraazacyclododecan-1-yl)methyl)pyridine 1-oxide (17); 2-((4,7,10-tris(carboxymethyl)-1,4,7,10-tetraazacyclododecan-1-yl) methyl)pyridine 1-oxide (18); 4-chloro-2-((4,7,10-tris(carboxymethyl)-1,4,7,10-tetraazacyclododecan-1-yl) methyl)pyridine 1-oxide (19); 2-((4,7,10-tris(carboxymethyl)-1,4,7,10-tetraazacyclododecan-1-yl) methyl)quinoline 1-oxide (20); 1-((4,7,10-tris(carboxymethyl)-1,4,7,10-tetraazacyclododecan-1-yl) methyl)isoquinoline 2-oxide (21); 3-((4,7,10-tris(carboxymethyl)-1,4,7,10-tetraazacyclododecan-1-yl) methyl)isoquinoline 2-oxide (22); 2,2',2''-(10-(2-hydroxybenzyl)-1,4,7,10-tetraazacyclododecane-1,4,7-triyl) triacetic acid (23); 2,2',2''-(10-(2-hydroxy-3-methylbenzyl)-1,4,7,10-tetraazacyclododecane-1,4,7-triyl)triacetic acid (24); 2,2',2''-(10-(2-hydroxy-4-methylbenzyl)-1,4,7,10-tetraazacyclododecane-1,4,7-triyl)triacetic acid (25); 2,2',2''-(10-(2-hydroxy-5-(methoxycarbonyl)benzyl)-1,4,7,10-tetraazacyclododecane-1,4,7-triyl)triacetic acid (26); 2,2',2''-(10-(2-hydroxy-5-nitrobenzyl)-1,4,7,10-tetraazacyclododecane-1,4,7-triyl)triacetic acid (27); 2,2',2''-(10-(2-methoxybenzyl)-1,4,7,10-tetraazacyclododecane-1,4,7-triyl)triacetic acid (28); 2,2',2''-(10-((3-methoxynaphthalen-2-yl)methyl)-1,4,7,10-tetraazacyclododecane-1,4,7-triyl)triacetic acid (29); 2,2',2''-(10-((1-methoxynaphthalen-2-yl)methyl)-1,4,7,10-tetraazacyclododecane-1,4,7-triyl)triacetic acid (30); 2,2',2''-(10-(2-carboxybenzyl)-1,4,7,10-tetraazacyclododecane-1,4,7-triyl)triacetic acid (31); 2,2',2''-(10-(3-carboxybenzyl)-1,4,7,10-tetraazacyclododecane-1,4,7-triyl) triacetic acid (32); 2,2',2''-(10-(4-carboxybenzyl)-1,4,7,10-tetraazacyclododecane-1,4,7-triyl)triacetic acid (33); 2,2',2''-(10-benzyl-1,4,7,10-tetraazacyclododecane-1,4,7-triyl) triacetic acid (34); 2,2',2''-(10-(4-methylbenzyl)-1,4,7,10-tetraazacyclododecane-1,4,7-triyl)triacetic acid (35); 2,2',2''-(10-(2-methylbenzyl)-1,4,7,10-tetraazacyclododecane-1,4,7-triyl)triacetic acid (36); 2,2',2''-(10-(4-nitrobenzyl)-1,4,7,10-tetraazacyclododecane-1,4,7-triyl)triacetic acid (37); 2,2',2''-(10-(2-nitrobenzyl)-1,4,7,10-tetraazacyclododecane-1,4,7-triyl)triacetic acid (38); 2,2',2''-(10-((perfluorophenyl)

methyl)-1,4,7,10-tetraazacyclododecane-1,4,7-triyl)triacetic acid (39); 2,2',2''-(10-(2-fluorobenzyl)-1,4,7,10-tetraazacyclododecane-1,4,7-triyl)triacetic acid (40); 2,2',2''-(10-(2,6-difluorobenzyl)-1,4,7,10-tetraazacyclododecane-1,4,7-triyl) triacetic acid (41); 2,2',2''-(10-(naphthalen-2-ylmethyl)-1,4,7,10-tetraazacyclododecane-1,4,7-triyl)triacetic acid (42); 2,2',2''-(10-(furan-2-ylmethyl)-1,4,7,10-tetraazacyclododecane-1,4,7-triyl)triacetic acid (43); 2,2',2''-(10-(2-oxo-2-phenylethyl)-1,4,7,10-tetraazacyclododecane-1,4,7-triyl)triacetic acid (44); 2,2'-(4-(2-hydroxy-5-nitrobenzyl)-1,4,7,10-tetraazacyclododecane-1,7-diyl)diacetic acid (45); 2,2'-(4,10-bis(2-hydroxy-5-nitrobenzyl)-1,4,7,10-tetraazacyclododecane-1,7-diyl)diacetic acid (46); 2,2'-(4-((6-carboxypyridin-2-yl)methyl)-1,4,7,10-tetraazacyclododecane-1,7-diyl)diacetic acid (47); 6,6'-((4,10-bis(carboxymethyl)-1,4,7,10-tetraazacyclododecane-1,7-diyl)bis(methylene))dipicolinic acid (48); 2,2'-(4-((6-methylpyridin-2-yl)methyl)-1,4,7,10-tetraazacyclododecane-1,7-diyl)diacetic acid (49); 2,2'-(4,10-bis((6-methylpyridin-2-yl)methyl)-1,4,7,10-tetraazacyclododecane-1,7-diyl)diacetic acid (50); 2-((4,10-bis(carboxymethyl)-1,4,7,10-tetraazacyclododecan-1-yl) methyl)pyridine 1-oxide (51); 2,2'-((4,10-bis (carboxymethyl)-1,4,7,10-tetraazacyclododecane-1,7-diyl) bis(methylene))bis(pyridine 1-oxide) (52); 2,2'-(4-((5-carboxyfuran-2-yl)methyl)-1,4,7,10-tetraazacyclododecane-1,7-diyl)diacetic acid (53); 5,5'-((4,10-bis(carboxymethyl)-1,4,7,10-tetraazacyclododecane-1,7-diyl)bis(methylene))bis(furan-2-carboxylic acid) (54); 2,2'-(4,10-dibenzyl-1,4,7,10-tetraazacyclododecane-1,7-diyl)diacetic acid (56); 2,2'-(4-((perfluorophenyl)methyl)-1,4,7,10-tetraazacyclododecane-1,7-diyl)diacetic acid (57); 2,2'-(4,10-bis((perfluorophenyl)methyl)-1,4,7,10-tetraazacyclododecane-1,7-diyl)diacetic acid (58); 2,2'-(4-((1-methoxynaphthalen-2-yl)methyl)-1,4,7,10-tetraazacyclododecane-1,7-diyl)diacetic acid (59); 2,2'-(4-((3-methoxynaphthalen-2-yl)methyl)-1,4,7,10-tetraazacyclododecane-1,7-diyl)diacetic acid (60); 2,2'-(4-(2-carboxybenzyl)-1,4,7,10-tetraazacyclododecane-1,7-diyl)diacetic acid (61); 2,2'-(4-(3-carboxybenzyl)-1,4,7,10-tetraazacyclododecane-1,7-diyl)diacetic acid (62); 2,2'-(4-(4-carboxybenzyl)-1,4,7,10-tetraazacyclododecane-1,7-diyl)diacetic acid (63); 2,2'-(4-(2-hydroxybenzyl)-1,4,7,10-tetraazacyclododecane-1,7-diyl)diacetic acid (64); 2,2'-(4-(2-hydroxy-3-methylbenzyl)-1,4,7,10-tetraazacyclododecane-1,7-diyl)diacetic acid (65); 2-((4,10-bis(carboxymethyl)-1,4,7,10-tetraazacyclododecan-1-yl) methyl)-6-methylpyridine 1-oxide (66); 2,2'-(4-(3-carboxy-2-hydroxybenzyl)-1,4,7,10-tetraazacyclododecane-1,7-diyl) diacetic acid (67); 2,2'-(4-((8-hydroxyquinolin-2-yl) methyl)-1,4,7,10-tetraazacyclododecane-1,7-diyl)diacetic acid (68); 2,2'-(4-benzyl-10-(2-hydroxy-5-nitrobenzyl)-1,4,7,10-tetraazacyclododecane-1,7-diyl)diacetic acid (69); 2-((7-benzyl-4,10-bis(carboxymethyl)-1,4,7,10-tetraazacyclododecan-1-yl)methyl)pyridine 1-oxide (70); 2,2'-(4-benzyl-10-((6-carboxypyridin-2-yl)methyl)-1,4,7,10-tetraazacyclododecane-1,7-diyl)diacetic acid (71); 2,2'-(4-(2-carboxyethyl)-10-((6-methylpyridin-2-yl)methyl)-1,4,7,10-tetraazacyclododecane-1,7-diyl)diacetic acid (72); 2,2'-(4-((6-bromopyridin-2-yl)methyl)-10-(2-carboxyethyl)-1,4,7,10-tetraazacyclododecane-1,7-diyl)diacetic acid (73); 2,2'-(4-(2-carboxyethyl)-10-((6-chloropyridin-2-yl)methyl)-1,4,7,10-tetraazacyclododecane-1,7-diyl)diacetic acid (74); 2,2'-(4-(2-carboxyethyl)-10-((6-fluoropyridin-2-yl)methyl)-1,4,7,10-tetraazacyclododecane-1,7-diyl)diacetic acid (75); 2,2'-(4-(2-carboxyethyl)-10-(pyridin-2-ylmethyl)-1,4,7,10-tetraazacyclododecane-1,7-diyl)diacetic acid (76); 2-((7-(2-carboxyethyl)-4,10-bis(carboxymethyl)-1,4,7,10-tetraazacyclododecan-1-yl)methyl)pyridine 1-oxide (77); 2-((4,10-bis(carboxymethyl)-7-(2-hydroxy-5-nitrobenzyl)-1,4,7,10-tetraazacyclododecan-1-yl)methyl)pyridine 1-oxide (78); 2-((4,10-bis(carboxymethyl)-7-((6-carboxypyridin-2-yl) methyl)-1,4,7,10-tetraazacyclododecan-1-yl)methyl)pyridine 1-oxide (79); 2,2'-(4-((6-carboxypyridin-2-yl)methyl)-10-(2-hydroxy-5-nitrobenzyl)-1,4,7,10-tetraazacyclododecane-1,7-diyl)diacetic acid (80); 2,2'-(4-((6-carboxypyridin-2-yl)methyl)-10-((6-chloropyridin-2-yl) methyl)-1,4,7,10-tetraazacyclododecane-1,7-diyl)diacetic acid (81); 2,2'-(4-((6-bromopyridin-2-yl)methyl)-10-((6-carboxypyridin-2-yl)methyl)-1,4,7,10-tetraazacyclododecane-1,7-diyl)diacetic acid (82); 2,2'-(4-((6-carboxypyridin-2-yl)methyl)-10-((6-methylpyridin-2-yl)methyl)-1,4,7,10-tetraazacyclododecane-1,7-diyl)diacetic acid (83); 2,2'-(4-((6-carboxypyridin-2-yl)methyl)-10-(pyridin-4-ylmethyl)-1,4,7,10-tetraazacyclododecane-1,7-diyl)diacetic acid (84); 2,2'-(4-((6-carboxypyridin-2-yl)methyl)-10-methyl-1,4,7,10-tetraazacyclododecane-1,7-diyl)diacetic acid (85); 2,2'-(4-((6-chloropyridin-2-yl)methyl)-10-(phosphonomethyl)-1,4,7,10-tetraazacyclododecane-1,7-diyl)diacetic acid (86); 2,2'-(4-((6-bromopyridin-2-yl)methyl)-10-((hydroxy (methyl)phosphoryl)methyl)-1,4,7,10-tetraazacyclododecane-1,7-diyl)diacetic acid (87); 2,2'-(4-((6-chloropyridin-2-yl)methyl)-10-((hydroxy(methyl)phosphoryl)methyl)-1,4,7,10-tetraazacyclododecane-1,7-diyl)diacetic acid (88); 2,2',2''-(10-(2-oxo-2-(pyridin-2-yl)ethyl)-1,4,7,10-tetraazacyclododecane-1,4,7-triyl)triacetic acid (89); 2,2',2''-(10-(pyrimidin-2-ylmethyl)-1,4,7,10-tetraazacyclododecane-1,4,7-triyl)triacetic acid (90); 2,2'-(4-(1-carboxyethyl)-10-((6-chloropyridin-2-yl)methyl)-1,4,7,10-tetraazacyclododecane-1,7-diyl)diacetic acid (91); 2,2'-(4-((6-chloropyridin-2-yl)methyl)-10-(2-(methylsulfonamido)ethyl)-1,4,7,10-tetraazacyclododecane-1,7-diyl)diacetic acid (92), 4-(butylcarbamoyl)-2-((4,7,10-tris(carboxymethyl)-1,4,7,10-tetraazacyclododecan-1-yl)methyl) pyridine 1-oxide; 4-(hexylcarbamoyl)-2-((4,7,10-tris (carboxymethyl)-1,4,7,10-tetraazacyclododecan-1-yl) methyl)pyridine 1-oxide; 4-(octylcarbamoyl)-2-((4,7,10-tris (carboxymethyl)-1,4,7,10-tetraazacyclododecan-1-yl) methyl)pyridine 1-oxide; 4-(tert-butylcarbamoyl)-2-((4,7,10-tris(carboxymethyl)-1,4,7,10-tetraazacyclododecan-1-yl)methyl)pyridine 1-oxide; 4-(benzylcarbamoyl)-2-((4,7,10-tris(carboxymethyl)-1,4,7,10-tetraazacyclododecan-1-yl)methyl)pyridine 1-oxide; 4-(butoxycarbonyl)-2-((4,7,10-tris(carboxymethyl)-1,4,7,10-tetraazacyclododecan-1-yl) methyl)pyridine 1-oxide; 4-((hexyloxy)carbonyl)-2-((4,7,10-tris(carboxymethyl)-1,4,7,10-tetraazacyclododecan-1-yl)methyl)pyridine 1-oxide; 4-((octyloxy)carbonyl)-2-((4,7,10-tris(carboxymethyl)-1,4,7,10-tetraazacyclododecan-1-yl)methyl)pyridine 1-oxide; 4-((benzyloxy)carbonyl)-2-((4,7,10-tris(carboxymethyl)-1,4,7,10-tetraazacyclododecan-1-yl)methyl)pyridine 1-oxide; 4-(isopropoxycarbonyl)-2-((4,7,10-tris(carboxymethyl)-1,4,7,10-tetraazacyclododecan-1-yl)methyl)pyridine 1-oxide; 5-(butylcarbamoyl)-2-((4,7,10-tris(carboxymethyl)-1,4,7,10-tetraazacyclododecan-1-yl) methyl)pyridine 1-oxide; 5-((benzyloxy)carbonyl)-2-((4,7,10-tris(carboxymethyl)-1,4,7,10-tetraazacyclododecan-1-yl)methyl)pyridine 1-oxide.

The object of the present invention is further a method of chromatographic separation of rare earth elements and/or s-, p- and d-block metals, selected from groups II.A, III.A, IV.A, V.A metals, transitional metals (preferably I.B, II.B and VIII.B group), from a mixture of at least two metal ions, at least one of them being a metal selected from Ce, Dy, Er, Eu, Gd, Ho, La, Lu, Nd, Pr, Pm, Sm, Sc, Tb, Tm, Yb, Y, alkaline earth metals, Al, Ga, In, Tl, Sn, Pb, Bi, transitional metals (preferably at least one of them being a metal selected from Ce, Dy, Er, Eu, Gd, Ho, La, Lu, Nd, Pr, Pm, Sm, Sc, Tb, Tm, Yb, Y, Ca, Fe, Co, Ni, Cu, Zn, Al, Pb, Bi), which comprises the following steps:

(a) providing a mixture of at least one metal ion selected from Ce, Dy, Er, Eu, Gd, Ho, La, Lu, Nd, Pr, Pm, Sm, Sc, Tb, Tm, Yb, Y, alkaline earth metals, Al, Ga, In, Tl, Sn, Pb, Bi, transitional metals, and at least one further metal ion, wherein said further metal ion is selected from rare earth metal ions, transition metal ions, non-transition metal ions and actinide ions, (b) metal ions comprised in said mixture are subjected to reaction with at least one compound of general formula (I) as defined in any one of the preceding claims to form chelates;

(c) the chelates from step (b) are subjected to chromatographic separation, preferably, the stationary phase is selected from silica ($SiO_2$), alumina ($Al_2O_3$), titania ($TiO_2$), zirconia ($ZrO_2$) or (C1-C18)derivatized reversed phase (such as C1-C18, phenyl, pentafluorophenyl, C1-C18 alkyl-phenyl or polymer-based reversed phase or carbon), and, preferably, the mobile phase comprises one or more of the solvents selected from water, C1-C4 alcohol, acetonitrile, acetone, N,N-dimethylformamide, dimethylsulfoxide, tetrahydrofurane, aqueous ammonia, the mobile phase can eventually comprise one or more additives for pH adjustment, such as acids, bases or buffers; the additives for pH adjustment are known to the person skilled in the art;

whereas optionally step (c) can be performed at least twice in order to increase the purity of at least one separated metal chelate;

and, optionally, (d) at least one metal chelate obtained from the chromatographic separation is subjected to acidic decomplexation to afford a non-complexed metal ion.

Preferably, fractions/spots containing the separated metal chelate from step (c) are combined together; preferably, the combined fractions containing the metal chelate being separated are concentrated, e.g. by evaporation, before repetition of step (c).

In one preferred embodiment, the method of chromatographic separation according to the present invention is the method of chromatographic separation of rare earth elements from a mixture of at least two metal ions, at least one of them being a rare earth metal selected from Ce, Dy, Er, Eu, Gd, Ho, La, Lu, Nd, Pr, Pm, Sm, Sc, Tb, Tm, Yb and Y, using compounds of general formula (I) as defined above, and comprising the following steps:

(a) providing a mixture of at least one rare earth metal ion selected from Ce, Dy, Er, Eu, Gd, Ho, La, Lu, Nd, Pr, Pm, Sm, Sc, Tb, Tm, Yb and Y, and at least one further metal ion, wherein said further metal ion is selected from rare earth metal ions, transition metal ions, non-transition metal ions and actinide ions, (b) metal ions comprised in said mixture are subjected to reaction with at least one compound of general formula (I) as defined above to form chelates;

(c) the chelates from step (b) are subjected to chromatographic separation, such as column chromatography, thin layer chromatography or high-performance liquid chromatography (HPLC); preferably, the stationary phase is selected from silica ($SiO_2$), alumina ($Al_2O_3$), titania ($TiO_2$), zirconia ($ZrO_2$) or (C1-C18)derivatized reversed phase (such as C1-C18, phenyl, pentafluorophenyl, C1-C18 alkyl-phenyl or polymer-based reversed phase or carbon)

and, preferably, the mobile phase comprises one or more of the solvents selected from water, C1-C4 alcohol, acetonitrile, acetone, N,N-dimethylformamide, dimethylsulfoxide, tetrahydrofurane, aqueous ammonia, the mobile phase can eventually comprise one or more additives for pH adjustment, such as acids, bases or buffers; the additives for pH adjustment are known to the person skilled in the art;

whereas optionally step (c) can be performed at least twice in order to increase the purity of at least one separated metal chelate;

and, optionally, (d) at least one metal chelate obtained from the chromatographic separation is subjected to acidic decomplexation to afford a non-complexed rare earth metal ion.

Preferably, fractions/spots containing the separated metal chelate from step (c) are combined together; preferably, the combined fractions containing the metal chelate being separated are concentrated, e.g. by evaporation, before repetition of step (c).

The further metal ion mentioned in step (a) is selected from rare earth metal ions, transition metal ions, non-transition metal ions and actinide ions. The rare earth metals are Ce, Dy, Er, Eu, Gd, Ho, La, Lu, Nd, Pr, Pm, Sm, Sc, Tb, Tm, Yb and Y, transition metals are metals of the d-block of the periodic table (groups I.B to VIII.B), non-transition metals are metals from the main group elements (groups A) of the periodic table and actinides are actinium through lawrencium, chemical elements with atomic numbers from 89 to 103.

The acid used for decomplexation in step (d) is preferably selected from hydrofluoric, hydrochloric, hydrobromic, hydroiodic, sulfuric, nitric, peroxosulfuric, perchloric, methanesulfonic, trifluoromethanesulfonic, formic, acetic, trifluoroacetic acid or a mixture thereof.

Step (d) can be followed by a chromatography of the resulting mixture in order to purify the free rare earth metal ions from molecules of the compound of general formula (I) or its fragments resulting from acid decomplexation. The method of chromatographic separation takes place in solution, and it is a routine work of a person skilled in the art to find suitable conditions for such chromatographic purification.

In one preferred embodiment, the chromatography in step a) is high-performance liquid chromatography (HPLC) performed using a stationary reversed phase, preferably selected from C1-C18, phenyl, pentafluorophenyl, C1-C18 alkyl-phenyl or polymer-based reversed phases, and a mobile phase consisting of water and 0-40% (vol.) of a water-miscible organic solvent, selected from the group comprising methanol, ethanol, propanol, isopropanol, acetonitrile, acetone, N,N-dimethylformamide, dimethylsulfoxide, tetrahydrofurane, and, optionally, the mobile phase further containing up to 10% (w/w) of an ion-pairing additive consisting of a cationic part and an anionic part, wherein the cationic part is selected from the group comprising $H^+$, $Li^+$, $Na^+$, $K^+$, $Rb^+$, $Cs^+$, $NH_4^+$, C1-C8 tetraalkylammonium, and wherein the anionic part is selected from the group comprising $F^-$, $Cl^-$, $Br^-$, $I^-$, sulfate, hydrogen sulfate, nitrate, perchlorate, methanesulfonate, trifluoromethanesulfonate, (C2-C18 alkyl)sulfonate, formate, acetate, (C2-C18 alkyl)carboxylate, lactate, malate, citrate, 2-hydroxyisobutyrate, mandelate, diglycolate, tartarate.

In a preferred embodiment, a solution containing the mixture provided in step (a) in the form of salts (e.g. chloride, bromide, sulfate, nitrate, methanesulfonate, trifluoromethanesulfonate, formate, acetate, lactate, malate, citrate, 2-hydroxyisobutyrate, mandelate, diglycolate, tartarate) or a solid phase containing the mixture provided in step (a) (e.g. in the form of oxide, hydroxide, carbonate), is mixed with a solution of the compound of general formula (I) in molar ratio of metal ions to compound of general formula (I) from 1:0.5 to 1:100, preferably from 1:0.7 to 1:50, more preferably from 1:0.9 to 1:10. Concentrations of the soluble components may be selected from the concentration range permitted by solubility of such compounds in a given solvent at a given temperature, preferably in the concentration range 0.000001-0.5 mol/L. The solvent may be water, a water-miscible organic solvent such as methanol, ethanol, propanol, isopropanol, acetone, acetonitrile, N,N-dimethylformamide, dimethylsulfoxide, tetrahydrofurane, or a mixture thereof. An organic or inorganic base, such as LiOH, NaOH, KOH, aqueous $NH_3$, triethylamine, N,N-diisopropylethylamine or pyridine, is added to the reaction mixture in order to compensate for protons released during the complexation, and the complexation takes place in the solution. Preferably, 1-10 molar equivalents of base are added per molecule of the compound of general formula (I). Eventually, the reaction can take place in a buffer. In such case there is no need of adding organic or inorganic base to the reaction mixture. The mixture is stirred or shaken at room temperature or elevated temperature for up to 24 hours to afford complete complexation. Preferably, the mixture is stirred or shaken at 40° C. for 15 minutes. A reasonable excess of the compound of general formula (I) may be used to accelerate the complexation and to shift the equilibrium towards formation of the chelates. The result of step (b) is a mixture of different metal chelates in solution.

In a preferred embodiment, the chromatographic separation of the chelates in step (b) takes place on normal or reversed stationary phase. The normal phase may be silica ($SiO_2$) or alumina ($Al_2O_3$). A variety of reversed phases may be used, including C1-C18, phenyl, pentafluorophenyl, (C1-C18 alkyl)-phenyl and polymer-based reversed phases. The solution of metal chelates may optionally be centrifuged or filtered prior to the chromatography in step (b), in order to remove particulates, such as insoluble impurities or dust. The separation may be achieved via a variety of chromatographic arrangements including column chromatography, thin layer chromatography (TLC) and high-performance liquid chromatography (HPLC). The excess of compound of general formula (I) is also separated during the chromatography. Preferably, the chromatographic separation is achieved using HPLC on C8, C18 or phenyl-hexyl reversed phase. In a preferred embodiment, a mobile phase is used that consists of water and 3-40% of methanol, ethanol or acetonitrile. Optionally, 0.01-0.1 mol/L of a buffer is used in the mobile phase, wherein the buffer comprises sodium acetate pH=4.5, ammonium formate pH=7.0 or ammonium acetate pH=7.0. Fractions containing the desired metal chelate are collected and combined, resulting in a solution significantly enriched in the content of the desired rare earth metal chelate compared to the original mixture of metal chelates prior to the chromatography. The process may be repeated to further increase the purity of the product.

In a preferred embodiment, the decomposition of the purified chelate in step (d) is performed by treating of the solution of the chromatographically purified chelate with an organic or inorganic acid in order to achieve decomplexation of the metal ion from the chelate. The organic or inorganic acid is selected from a group comprising hydrofluoric, hydrochloric, hydrobromic, hydroiodic, sulfuric, nitric, peroxosulfuric, perchloric, methanesulfonic, trifluoromethanesulfonic, formic, acetic, trifluoroacetic acid or a mixture thereof. The choice of the acid and of reaction conditions for achieving completeness of the decomplexation would be apparent to a person skilled in the art. Preferably, the decomplexation is achieved by using hydrochloric acid (0.01-12 mol/L) at 25-95° C. for time period of 5 minutes to 24 hours. A secondary chromatographic purification is then performed to remove the free chelator molecule (compound of general formula (I)) from rare earth metal ions. This may be achieved by a column chromatography or solid-phase extraction using a stationary reversed phase. Preferably, the reversed phase is C18 or polymer-based reversed phase. Preferably, a mobile phase is used that consists of pure water or water containing 0.01-1% (vol.) of the acid used in step (d) for decomposition of the chelate. The chelator is retained on the reversed phase, while the free metal ions are eluted in the form of a salt with the acid used in step (d) for decomposition of the chelate. Alternatively, the chromatographic separation described in step (c) is used. Yet another alternative is mineralization of the purified metal chelate by means of oxidation in nitric acid or peroxosulfuric acid. Preferably, the mineralization is achieved by mixing 1 part of the metal chelate solution with 4 or more parts of 70% nitric acid and incubating at 25-95° C. for time period of 5 minutes to 24 hours. In such case the chelator molecule is digested and no separation is needed.

The increase of concentration of combined fractions containing the metal chelate being separated before repetition of step (c) can be achieved by partial evaporation of the solvent or by adsorption of the chelate to lipophilic materials, such as a reversed phase. Preferably, the same reversed phase is used as for the chromatographic separation in step (c). When aqueous solution of the chelate is brought to physical contact with the reversed phase, it results in adsorption of the chelate. The chelate may then be desorbed from the reversed phase with a stronger eluent, wherein the stronger eluent contains higher percentage of a water-miscible organic solvent than the original solution of the chelate, wherein the water-miscible organic solvent is methanol, ethanol, propanol, isopropanol, acetone, acetonitrile, N,N-dimethylformamide, dimethylsulfoxide, tetrahydrofurane, or a mixture thereof. The strength of the eluent is controlled by the percentage of the water-miscible organic solvent in the mobile phase.

In a preferred embodiment, solution of metal chelates of the compounds of general formula (I) are concentrated by adsorption to reversed phase in two steps: (i) A diluted aqueous solution of the chelate is passed through the reversed phase, resulting in adsorption of the chelate. If the solution is a chromatographic fraction collected from a previous chromatographic separation and, as such, contains a water-miscible organic solvent, it is first diluted with distilled water prior to adsorption to decrease the eluent strength. Preferably, the solution is diluted with equal or higher volume of water, thus decreasing the percentage of the water-miscible organic solvent to one half or less of the original value. (ii) In the second step, the chelate is desorbed from the reversed phase with a stronger eluent containing higher percentage of the water-miscible organic solvent.

Preferably, the mobile phase used for chromatographic separation in step (c) is used as the eluent. In that case, a secondary chromatographic separation can be directly performed. Alternatively, a stronger eluent is used of a volume that is smaller than the original volume of adsorbed solution and the desorbed metal chelate is directly collected. In that case the concentration of the metal chelate is increased compared to the original solution. The advantage of this method is that it allows concentrating solutions of metal chelates without the need for time consuming evaporation, an operation that is not preferred particularly when working with radionuclides. Importantly, on a reversed-phase chromatographic column this method leads to sorption of the metal chelates in a narrow band at the beginning of the column and consecutively leads to sharp peaks and more efficient chromatographic separation. This is in contrast to broad peaks and poor separation that would result from the presence of a strong eluent in previously collected fractions, if such fractions were used unchanged for another chromatographic separation. Moreover, this method allows to repeat the chromatographic separations of previously collected chromatographic fractions in fast succession. Fast repetition of the chromatographic purification provides the desired metal chelate in high purity in shorter time.

The object of the present invention are also compounds of general formula (Ia),

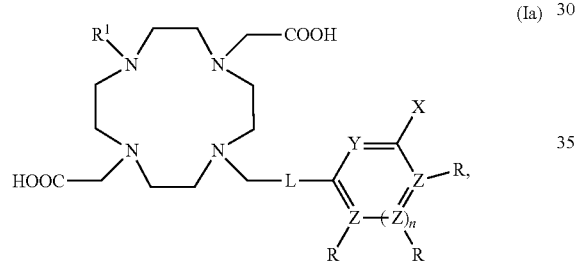

(Ia)

wherein

X is selected from a group consisting of H; F; Cl; Br; I; $C_1$ to $C_6$ alkyl; —Y is selected from a group consisting of nitrogen; N-oxide ($N^+$—$O^-$);

Z atoms are independently selected from the group consisting of carbon and nitrogen, wherein R is only present when the valence of Z allows it; and wherein at least one Z is carbon; and wherein n=0 or 1;

L is covalent bond;

at most one Z is other than carbon in each ring of the general formula (Ia), containing Z atoms;

R are independently selected from the group consisting of H; $C_1$ to $C_6$ alkyl; $C_1$ to $C_6$ alkyloxy; $C_6$ to $C_{10}$ aryloxy; benzyloxy; $C_1$ to $C_6$ alkylthio; $C_6$ to $C_{10}$ arylthio; F; Cl; Br; I; OH; SH; $NH_2$; $C_1$ to $C_6$ alkylamino; di($C_1$ to $C_6$ alkyl)amino; $C_1$ to $C_6$ acylamino; di($C_1$ to $C_6$ acyl)amino; $C_6$ to $C_{10}$ arylamino; di($C_6$ to $C_{10}$ aryl)amino; CN; OH; nitro; $COOR_n$, $C(O)NHR_n$, $C(O)N(R_n)_2$, wherein $R_n$ is independently H or $C_1$ to $C_{10}$ alkyl or $C_6$ to $C_{10}$ aryl; or neighboring two R together with neighboring two Z form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl; or X and the neighboring carbon, Z and R together form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl;

$R^1$ is selected from the group consisting of H; —($C_1$ to $C_6$ alkyl); benzyl, which can be optionally substituted independently with one or more substituents selected from nitro, OH; —($C_1$ to $C_2$ alkylen)COOH, the alkylen of which can optionally be substituted with $C_1$ to $C_6$ alkyl; —$CH_2P(O)(OH)_2$; —$CH_2P(O)(OH)(C_1$ to $C_6$ alkyl);

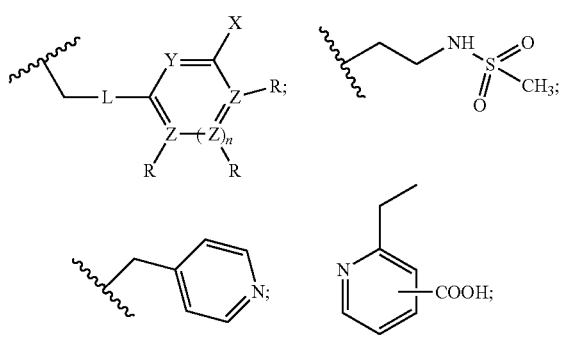

with the proviso that when Y is nitrogen, then at most one Z is nitrogen, and when Y is nitrogen, at most one Z is nitrogen and n is 1, then X is other than H;

or when Y is N-oxide, Z is carbon, and n is 1, then X is H, $CH_3$ or X and the neighboring carbon, Z and R form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein R is independently H or $C_1$ to $C_{10}$ alkyl or $C_6$ to $C_{10}$ aryl;

provided that the compound of general formula (Ia) is not:

4-carboxy-2-((4,7,10-tris(carboxymethyl)-1,4,7,10-tetraazacyclododecan-1-yl)methyl)pyridine 1-oxide; 2-((4,7,10-tris(carboxymethyl)-1,4,7,10-tetraazacyclododecan-1-yl)methyl)pyridine 1-oxide; 2,2'-((4,10-bis(carboxymethyl)-1,4,7,10-tetraazacyclododecane-1,7-diyl)bis(methylene))bis(pyridine 1-oxide); 6,6'-((4,10-bis(carboxymethyl)-1,4,7,10-tetraazacyclododecane-1,7-diyl)bis(methylene))bis(3-aminopyridine 1-oxide).

The general formula (Ia) of the present invention is meant to include all isomers, enantiomers and diastereoisomers.

Preferably, at most one Z is other than carbon.

Preferably, the ring containing Z atoms is selected from pyridine, pyrimidine, pyrrol, imidazol, indol, isoquinoline, quinoline, pyrazine, pyridine N-oxide, quinoline N-oxide, isoquinoline N-oxide, hydroxyquinoline; more preferably, the ring containing Z atoms is a pyridine ring, pyridine N-oxide ring, quinoline N-oxide or isoquinoline N-oxide.

Preferably, X is H, F, Cl, Br, I, $CH_3$.

Preferably, $R^1$ is selected from H, —$CH_2COOH$, —$CH_2CH_2COOH$, —$CH(CH_3)COOH$, —$CH_2P(O)(OH)_2$, —$CH_2P(O)(OH)(C_1$ to $C_6$ alkyl),

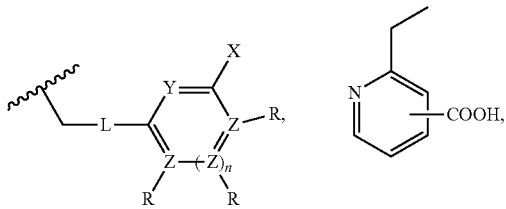

wherein L, X, Y, Z and R are independently selected and defined as above.

Preferably, R is selected from H, OH, $OCH_3$, F, Cl, Br, I, $CH_3$, $COOR_n$, $C(O)NHR_n$, $C(O)N(R_n)_2$, wherein R is independently H or $C_1$ to $C_{10}$ alkyl or $C_6$ to $C_{10}$ aryl.

In one preferred embodiment, when Y is nitrogen, all Z are carbon, and n is 1, then X is other than H, preferably X is F, Cl, Br, I, $CH_3$. Substituents R, $R^1$ and L are as defined by the general formula (Ia).

In another preferred embodiment, when Y is nitrogen, one Z is nitrogen, and n is 1, then X is other than H, preferably X is F, Cl, Br, I, $CH_3$. Substituents R, $R^1$ and L are as defined by the general formula (Ia).

In another preferred embodiment, when Y is N-oxide ($N^+$—$O^-$), Z is carbon, and n is 1, then X is H, $CH_3$ or X and the neighboring carbon, Z and R form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl) amino, $NO_2$, COOH, $COOR_n$, $C(O)NHR_n$, $C(O)N(R_n)_2$, wherein R is independently H or $C_1$ to $C_{10}$ alkyl or $C_6$ to $C_{10}$ aryl. Substituents R, $R^1$ and L are as defined by the general formula (Ia).

In another preferred embodiment, when Y is nitrogen, all Z are carbon, and n is 1, then X and the neighboring carbon, Z and R form a six-membered ring, optionally substituted with one or more substituents independently selected from the group consisting of OH, SH, $CF_3$, F, Cl, Br, I, $C_1$ to $C_6$ alkyl, $C_1$ to $C_6$ alkyloxy, $C_1$ to $C_6$ alkylthio, $NH_2$, $C_1$ to $C_6$ alkylamino, di($C_1$ to $C_6$ alkyl)amino, $NO_2$, COOH, $COOR_n$, $C(O)NHR_n$, $C(O)N(R_n)_2$, wherein $R_n$ is independently H or $C_1$ to $C_{10}$ alkyl or $C_6$ to $C_{10}$ aryl.

Substituents R, $R^1$ and L are as defined by the general formula (Ia).

In a preferred embodiment, the compounds of general formula (Ia) as defined above are selected from the group consisting of: 2,2',2''-(10-((6-fluoropyridin-2-yl)methyl)-1,4,7,10-tetraazacyclododecane-1,4,7-triyl)triacetic acid; 2,2',2''-(10-((6-chloropyridin-2-yl)methyl)-1,4,7,10-tetraazacyclododecane-1,4,7-triyl)triacetic acid; 2,2',2''-(10-((6-bromopyridin-2-yl)methyl)-1,4,7,10-tetraazacyclododecane-1,4,7-triyl)triacetic acid; 2,2',2''-(10-((6-methylpyridin-2-yl)methyl)-1,4,7,10-tetraazacyclododecane-1,4,7-triyl)triacetic acid; 2,2',2''-(10-((4,6-dimethylpyridin-2-yl)methyl)-1,4,7,10-tetraazacyclododecane-1,4,7-triyl)triacetic acid; 2,2',2''-(10-((6-methylpyrazin-2-yl)methyl)-1,4,7,10-tetraazacyclododecane-1,4,7-triyl)triacetic acid; 4-methyl-2-((4,7,10-tris(carboxymethyl)-1,4,7,10-tetraazacyclododecan-1-yl)methyl)pyridine 1-oxide; 2-methyl-6-((4,7,10-tris(carboxymethyl)-1,4,7,10-tetraazacyclododecan-1-yl)methyl)pyridine 1-oxide; 4-chloro-2-((4,7,10-tris(carboxymethyl)-1,4,7,10-tetraazacyclododecan-1-yl)methyl)pyridine 1-oxide; 2-((4,7,10-tris(carboxymethyl)-1,4,7,10-tetraazacyclododecan-1-yl)methyl)quinoline 1-oxide; 1-((4,7,10-tris(carboxymethyl)-1,4,7,10-tetraazacyclododecan-1-yl)methyl)isoquinoline 2-oxide; 3-((4,7,10-tris(carboxymethyl)-1,4,7,10-tetraazacyclododecan-1-yl)methyl)isoquinoline 2-oxide; 2,2'-(4-((6-methylpyridin-2-yl)methyl)-1,4,7,10-tetraazacyclododecane-1,7-diyl)diacetic acid; 2,2'-(4,10-bis((6-methylpyridin-2-yl)methyl)-1,4,7,10-tetraazacyclododecane-1,7-diyl)diacetic acid; 2-((4,10-bis(carboxymethyl)-1,4,7,10-tetraazacyclododecan-1-yl)methyl)pyridine 1-oxide; 2-((4,10-bis(carboxymethyl)-1,4,7,10-tetraazacyclododecan-1-yl)methyl)-6-methylpyridine 1-oxide; 2,2'-(4-((8-hydroxyquinolin-2-yl)methyl)-1,4,7,10-tetraazacyclododecane-1,7-diyl)diacetic acid; 2-((7-benzyl-4,10-bis(carboxymethyl)-1,4,7,10-tetraazacyclododecan-1-yl)methyl)pyridine 1-oxide; 2,2'-(4-(2-carboxyethyl)-10-((6-methylpyridin-2-yl)methyl)-1,4,7,10-tetraazacyclododecane-1,7-diyl)diacetic acid; 2,2'-(4-((6-bromopyridin-2-yl)methyl)-10-(2-carboxyethyl)-1,4,7,10-tetraazacyclododecane-1,7-diyl)diacetic acid; 2,2'-(4-(2-carboxyethyl)-10-((6-chloropyridin-2-yl)methyl)-1,4,7,10-tetraazacyclododecane-1,7-diyl)diacetic acid; 2,2'-(4-(2-carboxyethyl)-10-((6-fluoropyridin-2-yl)methyl)-1,4,7,10-tetraazacyclododecane-1,7-diyl)diacetic acid; 2-((7-(2-carboxyethyl)-4,10-bis(carboxymethyl)-1,4,7,10-tetraazacyclododecan-1-yl)methyl)pyridine 1-oxide; 2-((4,10-bis(carboxymethyl)-7-(2-hydroxy-5-nitrobenzyl)-1,4,7,10-tetraazacyclododecan-1-yl)methyl)pyridine 1-oxide; 2-((4,10-bis(carboxymethyl)-7-((6-carboxypyridin-2-yl)methyl)-1,4,7,10-tetraazacyclododecan-1-yl)methyl)pyridine 1-oxide; 2,2'-(4-((6-carboxypyridin-2-yl)methyl)-10-((6-chloropyridin-2-yl)methyl)-1,4,7,10-tetraazacyclododecane-1,7-diyl)diacetic acid; 2,2'-(4-((6-bromopyridin-2-yl)methyl)-10-((6-carboxypyridin-2-yl)methyl)-1,4,7,10-tetraazacyclododecane-1,7-diyl)diacetic acid; 2,2'-(4-((6-carboxypyridin-2-yl)methyl)-10-((6-methylpyridin-2-yl)methyl)-1,4,7,10-tetraazacyclododecane-1,7-diyl)diacetic acid; 2,2'-(4-((6-chloropyridin-2-yl)methyl)-10-(phosphonomethyl)-1,4,7,10-tetraazacyclododecane-1,7-diyl)diacetic acid; 2,2'-(4-((6-bromopyridin-2-yl)methyl)-10-((hydroxy(methyl)phosphoryl)methyl)-1,4,7,10-tetraazacyclododecane-1,7-diyl)diacetic acid; 2,2'-(4-((6-chloropyridin-2-yl)methyl)-10-((hydroxy(methyl)phosphoryl)methyl)-1,4,7,10-tetraazacyclododecane-1,7-diyl)diacetic acid; 2,2'-(4-(1-carboxyethyl)-10-((6-chloropyridin-2-yl)methyl)-1,4,7,10-tetraazacyclododecane-1,7-diyl)diacetic acid; 2,2'-(4-((6-chloropyridin-2-yl)methyl)-10-(2-(methylsulfonamido)ethyl)-1,4,7,10-tetraazacyclododecane-1,7-diyl)diacetic acid, 4-(butylcarbamoyl)-2-((4,7,10-tris(carboxymethyl)-1,4,7,10-tetraazacyclododecan-1-yl)methyl)pyridine 1-oxide; 4-(hexylcarbamoyl)-2-((4,7,10-tris(carboxymethyl)-1,4,7,10-tetraazacyclododecan-1-yl)methyl)pyridine 1-oxide; 4-(octylcarbamoyl)-2-((4,7,10-tris(carboxymethyl)-1,4,7,10-tetraazacyclododecan-1-yl)methyl)pyridine 1-oxide; 4-(tert-butylcarbamoyl)-2-((4,7,10-tris(carboxymethyl)-1,4,7,10-tetraazacyclododecan-1-yl)methyl)pyridine 1-oxide; 4-(benzylcarbamoyl)-2-((4,7,10-tris(carboxymethyl)-1,4,7,10-tetraazacyclododecan-1-yl)methyl)pyridine 1-oxide; 4-(butoxycarbonyl)-2-((4,7,10-tris(carboxymethyl)-1,4,7,10-tetraazacyclododecan-1-yl)methyl)pyridine 1-oxide; 4-((hexyloxy)carbonyl)-2-((4,7,10-tris(carboxymethyl)-1,4, 7,10-tetraazacyclododecan-1-yl)methyl)pyridine 1-oxide; 4-((octyloxy)carbonyl)-2-((4,7,10-tris(carboxymethyl)-1,4, 7,10-tetraazacyclododecan-1-yl)methyl)pyridine 1-oxide; 4-((benzyloxy)carbonyl)-2-((4,7,10-tris(carboxymethyl)-1, 4,7,10-tetraazacyclododecan-1-yl)methyl)pyridine 1-oxide; 4-(isopropoxycarbonyl)-2-((4,7,10-tris(carboxymethyl)-1,4, 7,10-tetraazacyclododecan-1-yl)methyl)pyridine 1-oxide; 5-(butylcarbamoyl)-2-((4,7,10-tris(carboxymethyl)-1,4,7, 10-tetraazacyclododecan-1-yl)methyl)pyridine 1-oxide; 5-((benzyloxy)carbonyl)-2-((4,7,10-tris(carboxymethyl)-1, 4,7,10-tetraazacyclododecan-1-yl)methyl)pyridine 1-oxide.

The disclosed invention represents an integrated approach for manipulation with metal ions in solution that greatly simplifies their transfer, purification and volume reduction, while simultaneously preventing contamination with other metals. This is particularly useful in handling metal radionuclides where these operations are problematic. The present invention allows to perform these operations in rapid succession, repeatedly and in varying order.

The method for chromatographic separation of metal ions according to the present invention is distinctly different from the existing chromatographic methods. In the existing methods, the selectivity towards different elements, such as rare earth elements, is introduced by the stationary phase, or by an additive that is added to the mobile phase in excess relative to the separated metals, or by both simultaneously (Kifle, D., Wibetoe, G. (2013), *J. Chromatogr. A* 1307, 86-90; Schwantes, J. M. et al. (2008) *J. Radioanal. Nucl. Chem.* 276(2), 533-542). In contrast, in the method according to the present invention the selectivity originates from the chelator molecule that remains closely associates with the metal ion throughout the whole separation process. The present invention thus allows using conventional stationary phases (e.g. normal phase: $SiO_2$; reversed phase: C18, C8, phenyl-hexyl, phenyl, polymer-based reversed phase) and mobile phases (such as: water/acetonitrile, water/methanol, water/ethanol, water/isopropanol), bearing no particular selectivity towards the particular elements for their efficient separation.

There are several distinct features of the chelators disclosed in this invention that present an important difference from the chelators and ligands used in the existing techniques for separation of elements, such as rare earth elements. The disclosed chelators possess an aromatic moiety that plays a major role in the polarity of the metal chelates. For this reason, the aromatic moiety is crucial for the ability of the chelators to distinguish metals based on polarity of the chelates. In addition, the aromatic moiety serves as a chromophore that facilitates detection of the chelator and metal chelates based on UV absorbance or quenching of fluorescence on a TLC plate. Another important feature of the disclosed chelators is that they form chelates with metals that are kinetically inert for the duration of the separation process. Notably, this property reduces the risk of contamination with other metals, as the metal to be purified cannot readily escape from the chelate nor can it be replaced by another metal ion.

The present invention provides a fast and convenient way to efficient separation even of neighboring lanthanides from each other, i.e. a separation that is a notoriously difficult problem.

All these operations can be easily automated to limit exposure of the operator to radiation in case that metal radionuclides are used. Presence of an aromatic chromophore moiety in the structure of the chelators facilitates detection by UV absorbance or by quenching of fluorescence on a TLC plate. Therefore, the present invention represents an integrated approach allowing to perform rapid transfer, purification and volume reduction of solutions of metal radionuclides.

EXAMPLES

Figure 1:
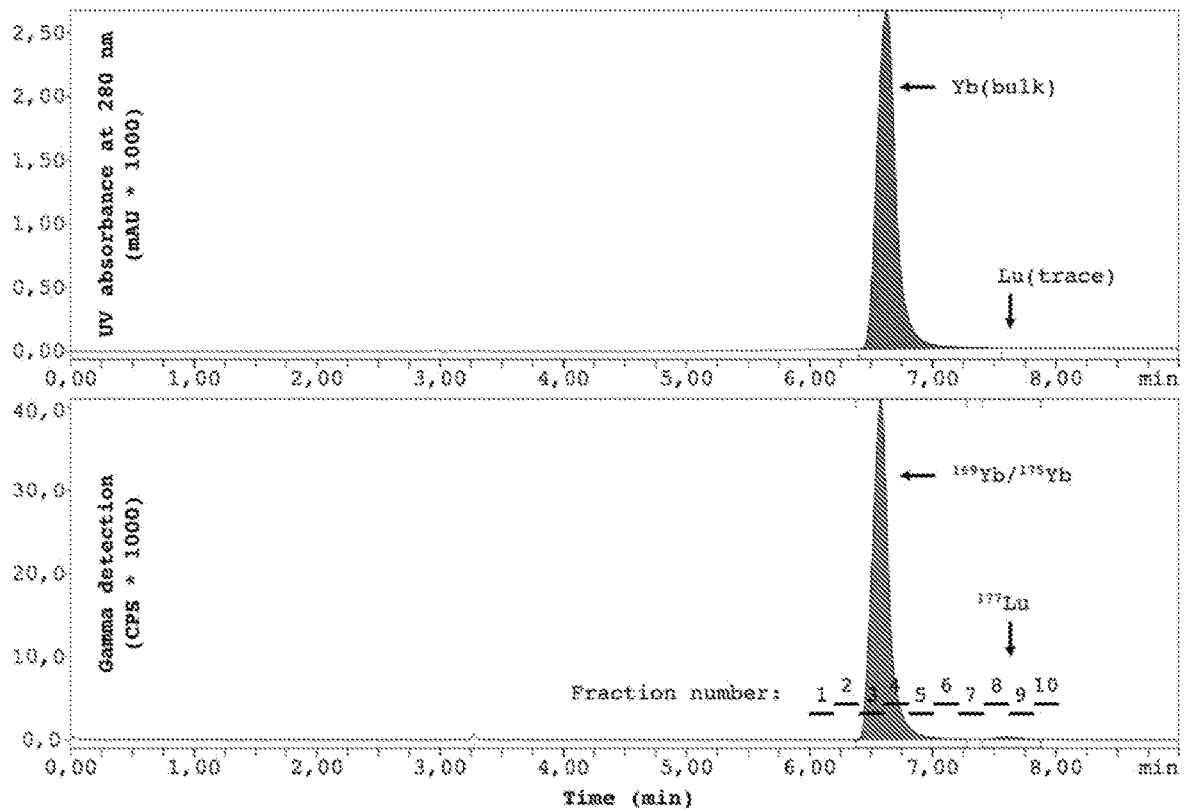
FIG. 1: A chromatogram showing UV absorbance at 280 nm (upper panel) and gamma detection (lower panel) of the separation of $^{177}$Lu from Yb target using a reversed-phase C18 column and elution with methanol/water mobile phase as described in Example 93 in accordance with the present invention. Positions of collected chromatographic fractions are marked in the lower panel.

The numerical values of chemical shift in NMR spectra are given in ppm. Notation used in the NMR spectra: s (singlet), d (dublet), t (triplet), q (quartet), m (multiplet), bs (broad singlet). The reference was set to the following values:

$^1$H (25° C.): 7.26 ppm ($CDCl_3$); 2.50 ppm (DMSO); 3.31 ppm ($CD_3OD$).

$^1$H (95° C.): 3.75 ppm (Dioxane); 1.95 ppm (MeCN); 4.23 ppm (HOD).

$^1$H (100° C.): 2.50 ppm (DMSO).

$^{13}$C (25° C.): 77.16 ppm ($CDCl_3$); 39.7 ppm (DMSO); 49.0 ppm ($CD_3OD$).

$^{13}$C (95° C.): 67.2 ppm (Dioxane).

$^{13}$C (100° C.): 39.7 ppm (DMSO).

$^{19}$F (95° C.): −163.0 ppm ($C_6F_6$).

$^{31}$P (95° C.): 0.0 ppm ($H_3PO_4$).

List of Abbreviations

EI (electron ionization); ESI (electrospray ionization); HATU (1-[Bis(dimethylamino)methylene]-1H-1,2,3-triazolo[4,5-b]pyridinium 3-oxid hexafluorophosphate); HPLC (high performance liquid chromatography); HRMS (high resolution mass spectrometry); LC-MS (liquid chromatography-mass spectrometry); NCA (no-carrier-added); TFA (trifluoroacetic acid); TLC (thin layer chromatography); UV (ultraviolet).

I. Synthesis of Compounds

Structures A and B of starting macrocyclic derivatives

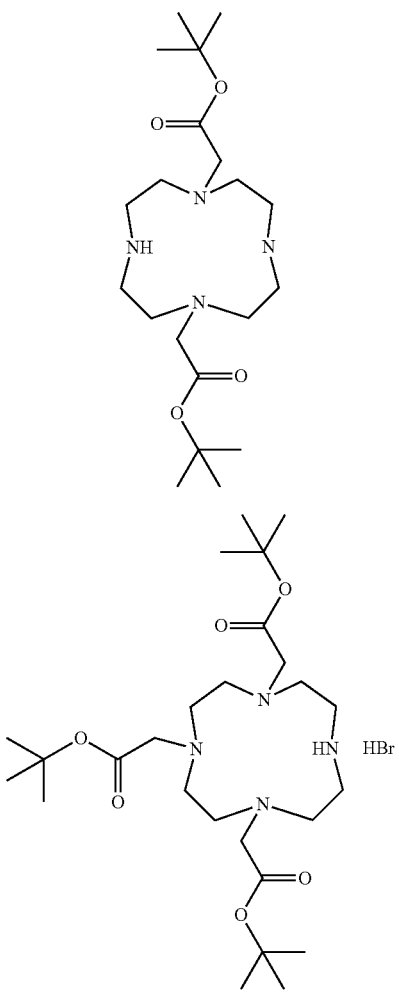

Example 1: Preparation of 2,2',2"-(10-((6-fluoropyridin-2-yl)methyl)-1,4,7,10-tetraazacyclododecane-1,4,7-triyl)triacetic acid (1)

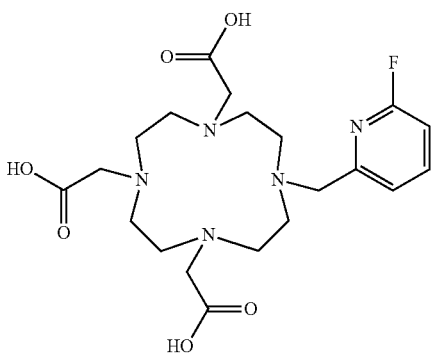 [SMILES: O=C(O)CN1CCN(CC(=O)O)CCN(Cc2cccc(F)n2)CCN(CC(=O)O)CC1]

Starting compound B (200 mg, 0.336 mmol), 2-(chloromethyl)-6-fluoropyridine hydrochloride (72 mg, 0.393 mmol), anhydrous potassium carbonate (185 mg, 1.340 mmol) and acetonitrile (10 mL) were placed into a 20 mL vial and the mixture was stirred under argon for 24 hours at room temperature. The solids were filtered off and the filtrate was concentrated on rotary evaporator. Resulting oil was purified on preparative HPLC (C18 column, acetonitrile/water gradient with 0.1% trifluoroacetic acid in the mobile phase). Fractions containing pure product in the form of tert.butyl ester were pooled, evaporated and dried in high vacuum. The residue was dissolved in neat trifluoroacetic acid (3 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and eluted with distilled water (10 mL). The eluate was lyophilized, redissolved in distilled water (2 mL) and lyophilized again, giving 199 mg of the product as a white fluffy solid (0.283 mmol, 84% yield relative to B).

$^1$H NMR (D$_2$O with internal dioxane reference, 95° C., 500 MHz): $\delta_H$ 3.15-3.33 (cycle, m, 8H); 3.47-3.54 (cycle, m, 8H); 3.63 (CH$_2$—COOH, s, 4H); 4.10 (CH$_2$—COOH, s, 2H); 4.53 (CH$_2$-arom., s, 2H); 7.13-7.23 (arom., m, 1H); 7.46-7.52 (arom., m, 1H); 8.03-8.11 (arom., m, 1H). $^{13}$C{$^1$H} NMR (D$_2$O with internal dioxane reference, 95° C., 125 MHz): 49.4 (cycle, s); 49.7 (cycle, s); 51.6 (cycle, s); 52.0 (cycle, s); 54.2 (CH$_2$—COOH, s); 55.4 (CH$_2$—COOH, s); 58.1 (CH$_2$-arom., s); 111.3 (arom., d, $^2J_{CF}$=35 Hz); 122.9 (arom., d, $^4J_{CF}$=4 Hz); 144.8 (arom., d, $^3J_{CF}$=9 Hz); 149.6 (arom., d, $^3J_{CF}$=9 Hz); 163.8 (arom., d, $^1J_{CF}$=242 Hz); $^{19}$F{$^1$H} NMR (D$_2$O with external C$_6$F$_6$ reference, 95° C., 470 MHz): −63.8 (s).

HRMS (ESI) m/z: [(M−H)$^-$] (C$_{20}$H$_{29}$FN$_5$O$_6$) calculated: 454.2107, found: 454.2106.

Elem. analysis: M·2.1TFA·0.5H$_2$O, calculated: C (41.3), H (4.7), N (9.9), F (19.7), found: C (41.9), H (4.8), N (9.3), F (19.4).

Example 2: Preparation of 2,2',2"-(10-((6-chloropyridin-2-yl)methyl)-1,4,7,10-tetraazacyclododecane-1,4,7-triyl)triacetic acid (2)

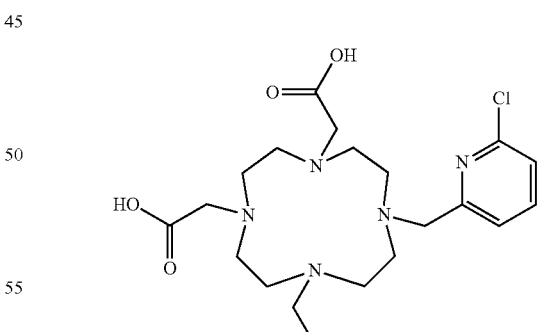

According to procedure in Example 1, reaction of starting compound B (410 mg, 0.688 mmol), 2-(bromomethyl)-6-chloropyridine (129 mg, 0.625 mmol) and anhydrous potassium carbonate (345 mg, 2.496 mmol) in acetonitrile (5 mL) gave analogously 324 mg of the product as a white fluffy solid (0.429 mmol, 69% yield relative to 2-(bromomethyl)-6-chloropyridine).

¹H NMR (D₂O with internal dioxane reference, 95° C., 500 MHz): δ$_H$ 3.28-3.35 (cycle, m, 4H); 3.35-3.42 (cycle, m, 4H); 3.51-3.60 (cycle, m, 8H); 3.73 (CH₂—COOH, s, 4H); 4.13 (CH₂—COOH, s, 2H); 4.56 (CH₂-arom., s, 2H); 7.63 (arom., d, 1H, ³J$_{HH}$=8 Hz); 7.64 (arom., d, 1H, ³J$_{HH}$=8 Hz); 8.00 (arom., t, 1H, ³J$_{HH}$=8 Hz); ¹³C{¹H} NMR (D₂O with internal dioxane reference, 95° C., 125 MHz): δ$_C$ 49.7 (cycle, s); 49.9 (cycle, s); 51.5 (cycle, s); 51.9 (cycle, s); 54.4 (CH₂—COOH, s); 55.5 (CH₂—COOH, s); 58.6 (CH₂-arom., s); 124.4 (arom., s); 126.1 (arom., s); 142.2 (arom., s); 151.7 (arom., s); 152.2 (arom., s); 170.1 (CO, s); 172.9 (CO, s). HRMS (ESI) m/z: [(M−H)⁻] (C₂₀H₂₉ClN₅O₆) calculated: 470.1812, found: 470.1811. Elem. analysis: M·2.2TFA·1.8H₂O, calculated: C (38.8), H (4.8), N (9.3), F (16.6), Cl (4.7), found: C (38.9), H (4.5), N (9.0), F (16.5), Cl (4.9).

Example 3: Preparation of 2,2',2''-(10-((6-bromopyridin-2-yl)methyl)-1,4,7,10-tetraazacyclododecane-1,4,7-triyl)triacetic acid (3)

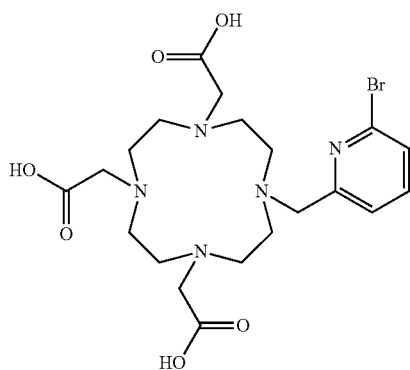

According to procedure in Example 1, reaction of starting compound B (200 mg, 0.336 mmol), 2-bromo-6-(chloromethyl)pyridine hydrochloride (83 mg, 0.340 mmol), anhydrous potassium carbonate (185 mg, 1.340 mmol) in acetonitrile (10 mL) gave analogously 179 mg of the product as a white fluffy solid (0.232 mmol, 69% yield relative to B).

¹H NMR (D₂O with internal dioxane reference, 95° C., 500 MHz): δ$_H$ 3.31-3.38 (cycle, m, 4H); 3.38-3.45 (cycle, m, 4H); 3.52-3.62 (cycle, m, 8H); 3.76 (CH₂—COOH, s, 4H); 4.14 (CH₂—COOH, s, 2H); 4.57 (CH₂-arom., s, 2H); 7.71 (arom., d, 1H, ³J$_{HH}$=8 Hz); 7.82 (arom., d, 1H, ³J$_{HH}$=8 Hz); 7.92 (arom., t, 1H, ³J$_{HH}$=8 Hz), ¹³C{¹H} NMR (D₂O with internal dioxane reference, 95° C., 125 MHz): δ$_C$ 49.8 (cycle, s); 50.0 (cycle, s); 51.5 (cycle, s); 51.9 (cycle, s); 54.4 (CH₂—COOH, s); 55.4 (CH₂—COOH, s); 58.6 (CH₂-arom., s); 125.0 (arom., s); 130.0 (arom., s); 141.8 (arom., s); 142.2 (arom., s); 152.8 (arom., s); 170.1 (CO, s); 172.8 (CO, s). HRMS (ESI) m/z: [(M−H)⁻] (C₂₀H₂₉BrN₅O₆) calculated: 514.1307, found: 514.1304. Elem. analysis: M·2TFA·1.6H₂O, calculated: C (37.3), H (4.6), N (9.1), F (14.7), Br (10.3), found: C (37.6), H (4.1), N (8.5), F (14.5), Br (10).

Example 4: Preparation of 2,2',2''-(10-((6-(trifluoromethyl)pyridin-2-yl)methyl)-1,4,7,10-tetraazacyclododecane-1,4,7-triyl)triacetic acid (4)

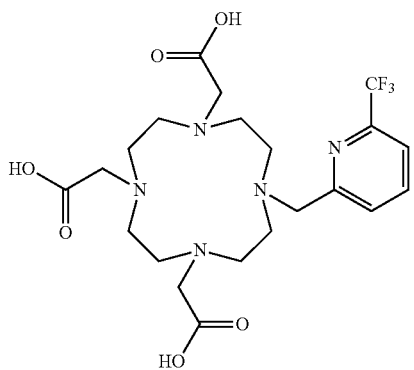 [SMILES: O=C(O)CN1CCN(CC(=O)O)CCN(Cc2cccc(C(F)(F)F)n2)CCN(CC(=O)O)CC1]

According to procedure in Example 1, reaction of starting compound B (76 mg, 0.128 mmol), 2-(chloromethyl)-6-(trifluoromethyl)pyridine (25 mg, 0.128 mmol), anhydrous potassium carbonate (71 mg, 0.511 mmol) in acetonitrile (5 mL) gave analogously 73 mg of the product as a white fluffy solid (0.103 mmol, 80% yield relative to B).

HRMS (ESI) m/z: [(M+H)⁺] (C₂₁H₃₁F₃N₅O₆) calculated: 506.2221, found: 506.2222.

Elem. analysis: M·1.5TFA·1.8H₂O, calculated: C (40.7), H (5.0), N (9.9), F (20.1), found: C (40.9), H (4.6), N (9.5), F (19.8).

Example 5: Preparation of 2,2',2''-(10-((6-methoxypyridin-2-yl)methyl)-1,4,7,10-tetraazacyclododecane-1,4,7-triyl)triacetic acid (5)

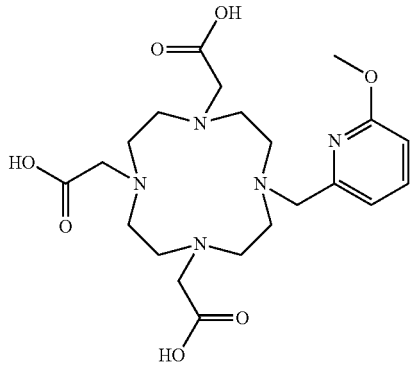 [SMILES: COc1cccc(CN2CCN(CC(=O)O)CCN(CC(=O)O)CCN(CC(=O)O)CC2)n1]

According to procedure in Example 1, reaction of starting compound B (250 mg, 0.420 mmol), 2-(chloromethyl)-6-methoxypyridine hydrochloride (95 mg, 0.489 mmol), anhydrous potassium carbonate (235 mg, 1.700 mmol) in, acetonitrile (10 mL) gave analogously 146 mg of the product as a white fluffy solid (0.211 mmol, 50% yield relative to B).

¹H NMR (D₂O with internal dioxane reference, 95° C., 500 MHz): δ$_H$ 3.25-3.36 (cycle, m, 4H); 3.36-3.48 (cycle, m, 12H); 3.68 (CH₂—COOH, s, 4H); 3.91 (CH₂—COOH, s, 2H); 4.12 (CH₃, s, 3H); 4.35 (CH₂-arom., s, 2H); 7.20 (arom., d, 1H, ³J$_{HH}$=9 Hz); 7.38 (arom., d, ³J$_{HH}$=7 Hz); 8.10 (arom., dd, ³J$_{HH}$=9 Hz, ³J$_{HH}$=7 Hz); ¹³C{¹H} NMR (D₂O with internal dioxane reference, 95° C., 125 MHz): 50.1

(cycle, s); 50.2 (cycle, s); 50.4 (cycle, s); 51.0 (cycle, s); 54.9 (CH$_2$—COOH, s); 55.2 (CH$_2$—COOH, s); 56.6 (CH$_3$, s); 57.2 (CH$_2$-arom., s); 111.9 (arom., s); 120.1 (arom., s); 144.6 (arom., s); 147.9 (arom., s); 164.4 (arom., s); 171.3 (CO, s); 172.0 (CO, s). HRMS (ESI) m/z: [(M+H)$^+$] (C$_{21}$H$_{34}$N$_5$O$_7$) calculated: 468.2453, found: 468.2454. Elem. analysis: M·1.9TFA·0.5H2O, calculated: C (43.0), H (5.2), N (10.1), F (15.6), found: C (42.9), H (5.0), N (9.9), F (15.5).

Example 6: Preparation of 2,2',2''-(10-((6-methylpyridin-2-yl)methyl)-1,4,7,10-tetraazacyclododecane-1,4,7-triyl)triacetic acid (6)

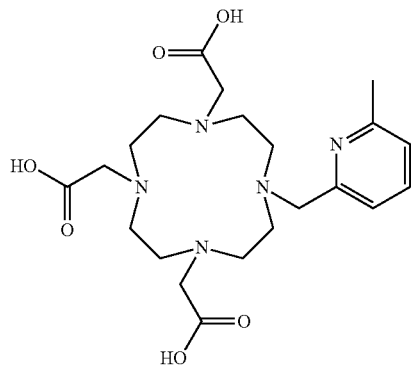

According to procedure in Example 1, reaction of starting compound B (400 mg, 0.672 mmol), 2-(chloromethyl)-6-methylpyridine hydrochloride (144 mg, 0.809 mmol), anhydrous potassium carbonate (371 mg, 2.686 mmol) in acetonitrile (20 mL) gave analogously 492 mg of the product as a white fluffy solid (0.593 mmol, 88% yield relative to B).

$^1$H NMR (D$_2$O with internal dioxane reference, 95° C., 500 MHz): δ$_H$ 2.89 (CH$_3$, s, 3H); 2.94-3.29 (cycle, m, 8H); 3.27-3.56 (cycle and CH$_2$—COOH, m, 6H); 3.56-3.74 (cycle, m, 4H); 3.76-4.02 (CH$_2$—COOH, m, 4H); 4.10 (CH$_2$-arom., s, 2H); 7.88 (arom., d, 1H, $^3$J$_{HH}$=8 Hz); 7.91 (arom., d, 1H, $^3$J$_{HH}$=8 Hz); 8.44 (arom., t, 1H, $^3$J$_{HH}$=8 Hz); $^{13}$C{$^1$H} NMR (D$_2$O with internal dioxane reference, 95° C., 125 MHz): δ$_C$ 20.3 (CH$_3$, s); 48.8 (cycle, s); 48.9 (cycle, s); 51.5 (cycle, s); 52.9 (cycle, s); 53.9 (CH$_2$—COOH, s); 54.5 (CH$_2$-arom., s); 56.4 (CH$_2$—COOH, s); 126.4 (arom., s); 128.6 (arom., s); 147.5 (arom., s); 149.6 (arom., s); 157.8 (arom., s); 169.3 (CO, s); 174.7 (CO, s). HRMS (ESI) m/z: [(M−H)$^-$] (C$_{21}$H$_{32}$N$_5$O$_6$) calculated: 450.2358, found: 450.2355. Elem. analysis: M·3.1TFA·1.4H$_2$O, calculated: C (39.4), H (4.7), N (8.4), F (21.3), found: C (39.3), H (4.5), N (8.2), F (21.1).

Example 7: Preparation of 2,2',2''-(10-((4,6-dimethylpyridin-2-yl)methyl)-1,4,7,10-tetraazacyclododecane-1,4,7-triyl)triacetic acid (7)

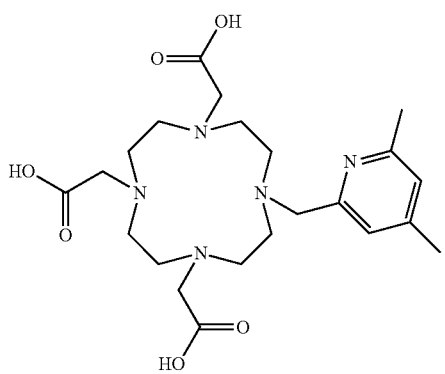 [SMILES: Cc1cc(C)nc(CN2CCN(CC(=O)O)CCN(CC(=O)O)CCN(CC(=O)O)CC2)c1]

According to procedure in Example 1, reaction of starting compound B (117 mg, 0.196 mmol), anhydrous potassium carbonate (108 mg, 0.781 mmol) and 2-(bromomethyl)-4,6-dimethylpyridine (55 mg, 0.275 mmol) gave analogously 86 mg of the product as a white fluffy solid (88 mmol, 45% yield relative to B).

$^1$H NMR (D$_2$O with internal dioxane reference, 95° C., 500 MHz): δ$_H$ 2.59 (CH$_3$, s, 3H); 2.77 (CH$_3$, s, 3H); 2.91-3.28 (cycle, m, 8H); 3.38-4.10 (cycle+CH$_2$—COOH+CH$_2$-arom., m, 16H); 7.65 (arom., s, 1H); 7.71 (arom., s, 1H). $^{13}$C{$^1$H} NMR (D$_2$O with internal dioxane reference, 95° C., 125 MHz): 19.9 (CH$_3$, s); 22.0 (CH$_3$, s); 48.8 (cycle, s); 48.9 (cycle, s); 51.5 (cycle, s); 53.0 (cycle, s); 53.8 (CH$_2$-arom., s); 54.3 (CH$_2$—COOH, s); 55.8 (CH$_2$—COOH, s); 127.1 (arom., s); 128.7 (arom., s); 148.6 (arom., s); 156.1 (arom., s); 162.3 (arom., s); 169.1 (CO, s); 174.8 (CO, s). HRMS (ESI) m/z: [(M+H)$^+$] (C$_{22}$H$_{36}$N$_5$O$_6$) calculated: 466.2660, found: 466.2661. Elem. analysis: M·4.3TFA·1.2H$_2$O, calculated: C (37.6), H (4.3), N (7.2), F (25.1), found: C (37.3), H (4.0), N (7.1), F (25.0).

Example 8: Preparation of 2,2',2''-(10-(pyridin-2-ylmethyl)-1,4,7,10-tetraazacyclododecane-1,4,7-triyl)triacetic acid (8)

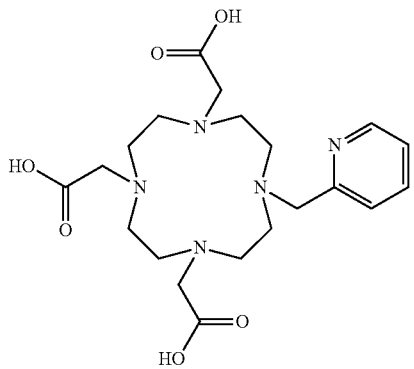 [SMILES: O=C(O)CN1CCN(CC(=O)O)CCN(Cc2ccccn2)CCN(CC(=O)O)CC1]

According to procedure in Example 1, reaction of starting compound B (200 mg, 0.336 mmol), anhydrous potassium carbonate (139 mg, 1.01 mmol) and 2-(chloromethyl)pyridine hydrochloride (65 mg, 0.396 mmol) gave analogously 226 mg of the product as a white fluffy solid (276 mmol, 82% yield relative to B).

HRMS (ESI) m/z: [(M+H)⁺] ($C_{20}H_{32}N_5O_6$) calculated: 438.2347, found: 438.2348. Elem. analysis: M·3.2TFA·1.0H$_2$O, calculated: C (38.7), H (4.4), N (8.5), F (22.2), found: C (38.7), H (4.2), N (8.5), F (22.0).

Example 9: Preparation of 2,2',2''-(10-(isoquinolin-1-ylmethyl)-1,4,7,10-tetraazacyclododecane-1,4,7-triyl)triacetic acid (9)

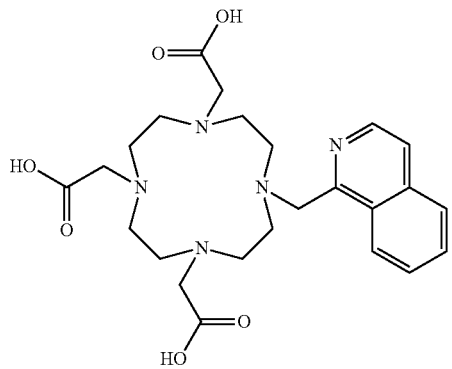 [SMILES: O=C(O)CN1CCN(CC(=O)O)CCN(Cc2nccc3ccccc23)CCN(CC(=O)O)CC1]

Example 10: Preparation of 2,2',2''-(10-(isoquinolin-3-ylmethyl)-1,4,7,10-tetraazacyclododecane-1,4,7-triyl)triacetic acid (10)

According to procedure in Example 1, reaction of starting compound (240 mg, 0.403 mmol), anhydrous potassium carbonate (200 mg, 1.45 mmol) and 1-(bromomethyl)isoquinoline (80 mg, 0.360 mmol) in acetonitrile (10 mL) gave analogously 235 mg of the product as a white fluffy solid (0.294 mmol, 82% yield relative to 1-(bromomethyl)isoquinoline).

¹H NMR (D$_2$O with internal dioxane reference, 95° C., 500 MHz): $\delta_H$ 3.00-3.74 (cycle+CH$_2$—COOH, m, 22H); 4.81 (CH$_2$-arom, s, 2H); 8.11 (arom., ddd, 1H, ³$J_{HH}$=8 Hz, ³$J_{HH}$=7 Hz, ⁴$J_{HH}$=1 Hz); 8.24 (arom., ddd, 1H, ³$J_{HH}$=8 Hz, ³$J_{HH}$=7 Hz, ⁴$J_{HH}$=1 Hz); 8.30 (arom., dm, 1H, ³$J_{HH}$=8 Hz); 8.38 (arom., dm, 1H, ³$J_{HH}$=7 Hz); 8.53 (arom., d, 1H, ³$J_{HH}$=7 Hz); 8.63 (arom., ddd, 1H, ³$J_{HH}$=9 Hz, ⁴$J_{HH}$=2 Hz, ⁴$J_{HH}$=1 Hz); ¹³C{¹H} NMR (D$_2$O with internal dioxane reference, 95° C., 125 MHz): $\delta_C$ 49.3 (cycle, s); 50.0 (cycle, s); 51.1 (cycle, s); 52.0 (CH$_2$-arom., s); 52.4 (cycle, s); 54.1 (CH$_2$—COOH, s); 56.0 (CH$_2$—COOH, s); 126.1 (arom., s); 126.5 (arom., s); 127.0 (arom., s); 129.3 (arom., s); 132.4 (arom., s); 133.8 (arom., s); 137.1 (arom., s); 139.7 (arom., s); 153.3 (arom., s); 169.7 (CO, s); 175.0 (CO, s).

HRMS (ESI) m/z: [(M−H)⁻] ($C_{24}H_{32}N_5O_6$) calculated: 486.2358, found: 486.2359.

Elem. analysis: M·2.4TFA·2.1H$_2$O, calculated: C (43.3), H (5.0), N (8.8), F (17.1), found: C (42.7), H (4.4), N (8.4), F (16.6).

According to procedure in Example 1, reaction of starting compound B (240 mg, 0.403 mmol), anhydrous potassium carbonate (200 mg, 1.45 mmol) and 1-(bromomethyl)isoquinoline (80 mg, 0.360 mmol) in acetonitrile (10 mL) gave analogously 213 mg of the product as a white fluffy solid (0.263 mmol, 73% yield relative to 1-(bromomethyl)isoquinoline).

¹H NMR (D$_2$O with internal dioxane reference, 95° C., 500 MHz): $\delta_H$ 3.01-3.29 (cycle, m, 8H); 3.44-3.47 (cycle, m, 4H); 3.49 (CH$_2$—COOH, s, 2H); 3.56-3.70 (cycle, m, 4H); 3.71-3.85 (CH$_2$—COOH, m, 4H); 4.26 (CH$_2$-arom, s, 2H); 8.08 (arom., ddd, 1H, ³$J_{HH}$=8 Hz, ³$J_{HH}$=6 Hz, ⁴$J_{HH}$=3 Hz); 8.22-8.31 (arom., m, 2H); 8.43 (arom., s, 1H); 8.50 (arom., dd, 1H, ³$J_{HH}$=8 Hz, ⁴$J_{HH}$=1 Hz); 9.62 (arom., s, 1H). ¹³C{¹H}NMR (D$_2$O with internal dioxane reference, 95° C., 125 MHz): $\delta_C$ 48.9 (cycle, s); 49.1 (cycle, s); 51.5 (cycle, s); 52.7 (cycle, s); 54.0 (CH$_2$—COOH, s); 54.6 (CH$_2$-arom., s); 56.2 (CH$_2$—COOH, s); 127.0 (arom., s); 127.4 (arom., s); 128.3 (arom., s); 131.4 (arom., s); 132.3 (arom., s); 138.4 (arom., s); 139.2 (arom., s); 139.6 (arom., s); 150.0 (arom., s); 169.3 (CO, s); 175.3 (CO, s).

HRMS (ESI) m/z: [(M−H)⁻] ($C_{24}H_{32}N_5O_6$) calculated: 486.2358, found: 486.2360.

Elem. analysis: M·2.6TFA·1.5H$_2$O, calculated: C (43.2), H (4.8), N (8.6), F (18.3), found: C (42.8), H (4.3), N (8.5), F (18.0).

Example 11: Preparation of 2,2',2"-(10-(quinolin-2-ylmethyl)-1,4,7,10-tetraazacyclododecane-1,4,7-triyl)triacetic acid (11)

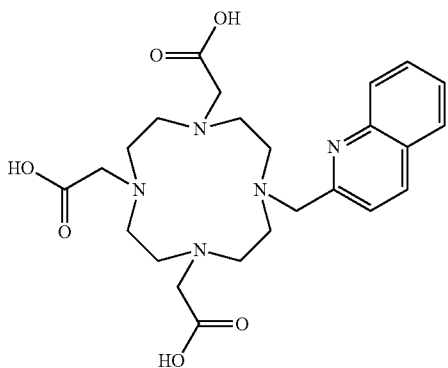 [SMILES: O=C(O)CN1CCN(CC(=O)O)CCN(Cc2ccc3ccccc3n2)CCN(CC(=O)O)CC1]

According to procedure in Example 1, reaction of starting compound B (200 mg, 0.336 mmol), anhydrous potassium carbonate (186 mg, 1.35 mmol) and 2-(chloromethyl)quinoline hydrochloride (86 mg, 0.402 mmol) in acetonitrile (10 mL) gave analogously 163 mg of the product as a white fluffy solid (0.196 mmol, 58% yield relative to B).

HRMS (ESI) m/z: [(M+H)$^+$] ($C_{24}H_{34}N_5O_6$) calculated: 488.2504, found: 488.2505.

Elem. analysis: M·2.7TFA·2.0H$_2$O, calculated: C (42.5), H (4.8), N (8.4), F (18.5), found: C (42.2), H (4.3), N (8.1), F (18.0).

Example 12: Preparation of 2,2',2"-(10-((6-carboxypyridin-2-yl)methyl)-1,4,7,10-tetraazacyclododecane-1,4,7-triyl)triacetic acid (12)

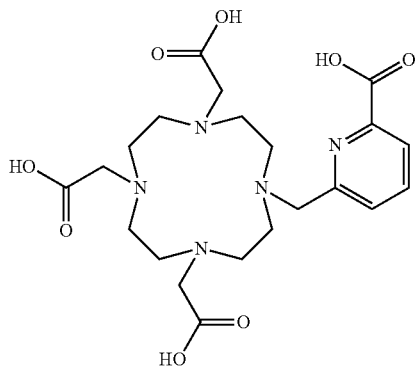 [SMILES: O=C(O)CN1CCN(CC(=O)O)CCN(Cc2cccc(C(=O)O)n2)CCN(CC(=O)O)CC1]

Starting compound B (279 mg, 0.468 mmol), methyl 6-(chloromethyl)picolinate hydrochloride (104 mg, 0.468 mmol), anhydrous potassium carbonate (233 mg, 1.68 mmol) and acetonitrile (15 mL) were placed into a 50 mL flask and the mixture was stirred under argon for 4 days at room temperature. The solids were filtered off and the filtrate was concentrated on rotary evaporator. Resulting oil was dissolved in a mixture of methanol (2 mL) and distilled water (2 mL). Hydrolysis of the methylester function followed by addition of 2 M aqueous sodium hydroxide (0.674 mL, 1.348 mmol) and stirring at room temperature. After 45 minutes the reaction was complete (followed by LC-MS). The reaction mixture was acidified with trifluoroacetic acid (0.206 mL, 2.70 mmol) and evaporated on rotary evaporator. The residue was purified on preparative HPLC (C18 column, acetonitrile/water gradient with 0.1% trifluoroacetic acid in the mobile phase). Fractions containing the intermediate with free carboxylic group on pyridine were pooled, evaporated and dried in high vacuum. The residue was dissolved in neat trifluoroacetic acid (4 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 280 mg of the product as a white fluffy solid (0.367 mmol, 78% yield relative to B).

$^1$H NMR (D$_2$O with internal dioxane reference, 25° C., 500 MHz): $\delta_H$ 3.34-3.41 (cycle, m, 4H); 3.41-3.52 (cycle, m, 12H); 3.70-3.76 (CH$_2$—COOH, m, 4H); 3.96 (CH$_2$—COOH, s, 2H); 4.56 (CH$_2$-arom., s, 2H); 8.03 (arom., dd, 1H, $^3J_{HH}$=7 Hz, $^4J_{HH}$=2 Hz). 8.28-8.35 (arom., m, 2H). $^{13}$C{$^1$H} NMR (D$_2$O with internal dioxane reference, 25° C., 125 MHz): $\delta_C$ 50.4 (cycle, s); 50.6 (cycle, s); 50.9 (cycle, s); 51.2 (cycle, s); 54.8 (CH$_2$—COOH, s); 55.3 (CH$_2$—COOH, s); 58.3 (CH$_2$-arom., s); 126.4 (arom., s); 130.0 (arom., s); 142.4 (arom., s); 148.1 (arom., s); 152.3 (arom., s); 171.5 (CO, s); 172.1 (CO, s).

HRMS (ESI) m/z: [(M+Na)$^+$] ($C_{21}H_{31}N_5NaO_8$) calculated: 504.2065, found: 504.2059.

Elem. analysis: M·2.2TFA·1.7H$_2$O, calculated: C (40.0), H (4.8), N (9.2), F (16.4), found: C (40.0), H (4.3), N (8.7), F (15.9).

Example 13: Preparation of 2,2',2"-(10-((6-methylpyrazin-2-yl)methyl)-1,4,7,10-tetraazacyclododecane-1,4,7-triyl)triacetic acid (13)

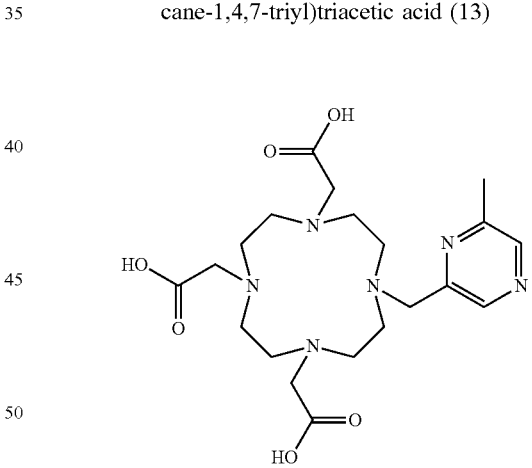

According to procedure in Example 1, reaction of starting compound B (265 mg, 0.445 mmol), anhydrous potassium carbonate (246 mg, 1.783 mmol) and 2-(bromomethyl)-6-methylpyrazine (103 mg, 0.551 mmol) acetonitrile (15 mL) gave analogously 196 mg of the product as a pale yellow solid foam (0.281 mmol, 63% yield relative to B).

$^1$H NMR (aqueous LiOD with internal dioxane reference, pD≥12, 95° C., 500 MHz): $\delta_H$ 2.56-2.86 (CH$_3$ and cycle, m, 19H); 3.03 (CH$_2$—COOH, s, 4H); 3.25 (CH$_2$—COOH, s, 2H); 3.88 (CH$_2$-arom., s, 2H); 8.48 (arom., s, 1H); 8.62 (arom., s, 1H); $^{13}$C{$^1$H} NMR (aqueous LiOD with internal dioxane reference, pD≥12, 95° C., 125 MHz): $\delta_C$ 21.1 (CH$_3$, s); 50.9 (cycle, s); 51.3 (cycle, s); 52.8 (cycle, s); 53.3 (cycle, s); 58.0 (CH$_2$-arom., s); 59.2 (CH$_2$—COOH, s); 59.4

(CH₂—COOH, s); 143.0 (arom., s); 143.6 (arom., s); 152.9 (arom., s); 154.5 (arom., s); 179.8 (CO, s); 180.5 (CO, s).

HRMS (ESI) m/z: [(M−H)⁻] ($C_{20}H_{31}N_6O_6$) calculated: 451.2311, found: 451.2309.

Elem. analysis: M·1.8TFA·2.2H₂O, calculated: C (40.6), H (5.5), N (12.1), F (14.7), found: C (40.8), H (5.6), N (11.8), F (14.7).

Example 14: Preparation of 2,2',2''-(10-(pyrazin-2-ylmethyl)-1,4,7,10-tetraazacyclododecane-1,4,7-triyl)triacetic acid (14)

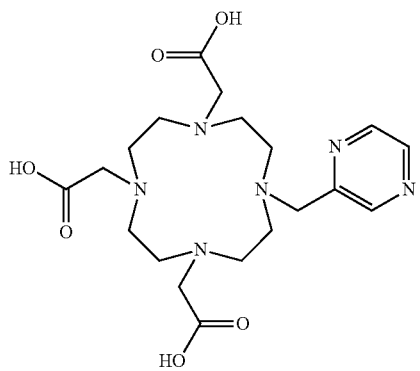 [SMILES: O=C(O)CN1CCN(CC(=O)O)CCN(Cc2cnccn2)CCN(CC(=O)O)CC1]

According to procedure in Example 1, reaction of starting compound B (238 mg, 0.400 mmol), anhydrous potassium carbonate (220 mg, 1.594 mmol) and 2-(chloromethyl) pyrazine hydrochloride (96 mg, 0.582 mmol) in acetonitrile (10 mL) gave analogously 161 mg of the product as a pale yellow solid foam (0.217 mmol, 54% yield relative to B).

¹H NMR (D₂O with internal dioxane reference, 95° C., 500 MHz): $δ_H$ 3.30-3.36 (cycle, m, 4H); 3.33-3.42 (cycle, m, 4H); 3.52-3.57 (cycle, m, 4H); 3.57-3.62 (cycle, m, 4H); 3.73 (CH₂—COOH, s, 4H); 4.15 (CH₂—COOH, s, 2H); 4.73 (CH₂-arom., s, 2H); 8.74-8.78 (arom., m, 2H); 8.81-8.85 (arom., m, 1H); ¹³C{¹H} NMR (D₂O with internal dioxane reference, 95° C., 125 MHz): $δ_C$ 49.8 (cycle, s); 50.0 (cycle, s); 51.8 (cycle, s); 51.9 (cycle, s); 54.3 (CH₂—COOH, s); 55.3 (CH₂—COOH, s); 56.3 (CH₂-arom., s); 144.9 (arom., s); 145.0 (arom., s); 145.4 (arom., s); 148.6 (arom., s); 170.3 (CO, s); 172.7 (CO, s). HRMS (ESI) m/z: [(M+H)⁺] ($C_{19}H_{31}N_6O_6$) calculated: 439.2300, found: 439.2300. Elem. analysis: M·2.5TFA·1.1H₂O, calculated: C (38.8), H (4.7), N (11.3), F (19.2), found: C (39.2), H (4.4), N (10.9), F (18.9).

Example 15: Preparation of 4-methyl-2-((4,7,10-tris(carboxymethyl)-1,4,7,10-tetraazacyclododecan-1-yl)methyl)pyridine 1-oxide (15)

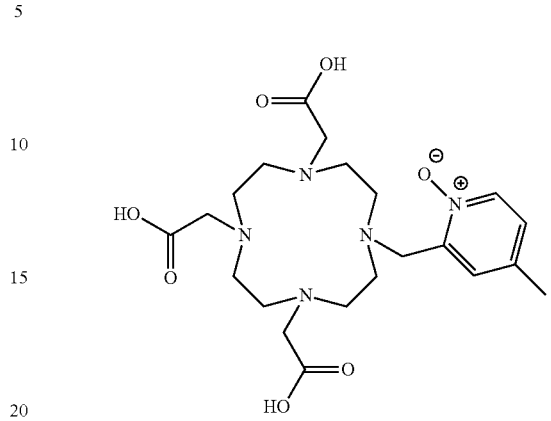

According to procedure in Example 1, reaction of starting compound B (179 mg, 0.300 mmol), 2-(chloromethyl)-4-methylpyridine 1-oxide (52 mg, 0.330 mmol), anhydrous potassium carbonate (166 mg, 1.200 mmol) in acetonitrile (10 mL) gave analogously 40 mg of the product as a white fluffy solid (0.053 mmol, 18% yield relative to B).

¹H NMR (D₂O with internal dioxane reference, 95° C., 500 MHz): $δ_H$ 2.45 (CH₃, s, 3H) 3.22-3.40 (cycle, m, 12H); 3.40-3.48 (cycle, m, 4H); 3.61 (CH₂—COOH, s, 4H); 4.00 (CH₂—COOH, s, 2H); 4.55 (CH₂-arom., s, 2H); 7.52 (arom., dd, 1H, $^3J_{HH}$=8 Hz, $^4J_{HH}$=3 Hz); 7.66 (arom., d, 1H, $^4J_{HH}$=3 Hz); 8.27 (arom., d, 1H, $^4J_{HH}$=7 Hz); ¹³C{¹H} NMR (D₂O with internal dioxane reference, 95° C., 125 MHz): 20.3 (CH₃, s); 49.9 (cycle, s); 50.1 (cycle, s); 51.5 (cycle, s); 51.8 (cycle, s); 53.9 (CH₂—COOH, s); 54.0 (CH₂-arom., s); 55.7 (CH₂—COOH, s); 129.3 (arom., s); 130.7 (arom., s); 140.0 (arom., s); 141.5 (arom., s); 146.0 (arom., s); 170.8 (CO, s); 172.3 (CO, s).

HRMS (ESI) m/z: [(M+Na)⁺] ($C_{21}H_{33}N_5NaO_7$) calculated: 490.2272, found: 490.2269.

Elem. analysis: M·1.9TFA·3.8H₂O, calculated: C (39.6), H (5.7), N (9.3), F (14.4), found: C (39.2), H (5.1), N (9.1), F (13.8).

Example 16: Preparation of 2-(chloromethyl)-6-methylpyridine 1-oxide (16a)

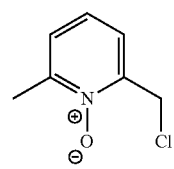

m-chloroperoxobenzoic acid (77%, 1.465 g, 6.54 mmol) was dissolved in dichloromethane (25 mL) and cooled in water-ice bath. 2-(chloromethyl)-6-methylpyridine hydrochloride (388 mg, 2.18 mmol) was dissolved in dichloromethane (4 mL) and added dropwise to the solution of m-chloroperoxobenzoic acid while stirring. The ice bath was removed and the reaction was continued while stirring for 16 h at room temperature. The volume of the solvent was reduced on rotary evaporator to 10 mL, causing m-chlorobenzoic acid to partially precipitate. The white precipitate was removed by filtration, the filtrate was evaporated and the residue loaded onto a column containing 20 g of neutral alumina. The column was washed with dichloromethane:methanol (98:2) mixture and the eluate was evaporated on rotary evaporator. The residue was purified with the same procedure on a fresh column of neutral alumina. The eluate was evaporated on rotary evaporator and the residue recrystallized from a minimum volume of dichloromethane, giving 242 mg of the product as colorless needles (1.54 mmol, 71% yield).

$^1$H NMR (CDCl$_3$, 25° C., 500 MHz): $\delta_H$ 2.54 (CH$_3$, s, 3H); 4.85 (CH$_2$, s, 2H); 7.18-7.23 (arom., m, 1H); 7.24-7.28 (arom., m, 1H); 7.47-7.51 (arom., m, 1H); $^{13}$C{$^1$H} NMR (CDCl$_3$, 25° C., 125 MHz): $\delta_C$ 18.0 (CH$_3$, s); 40.5 (CH$_2$, s); 123.3 (arom., s); 125.1 (arom., s); 125.7 (arom., s); 147.3 (arom., s); 149.4 (arom., s). HRMS (EI) m/z: [M$^+$] (C$_7$H$_8$ClNO) calculated: 157.0294, found: 157.0292.

Preparation of 2-methyl-6-((4,7,10-tris(carboxymethyl)-1,4,7,10-tetraazacyclododecan-1-yl)methyl)pyridine 1-oxide (16)

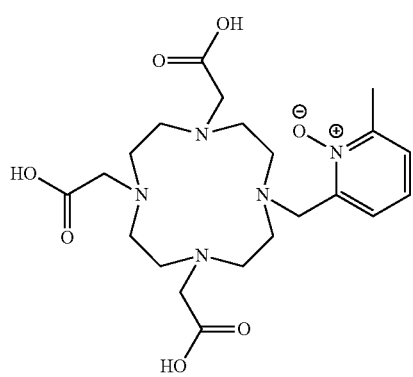 [SMILES: Cc1cccc(CN2CCN(CC(=O)O)CCN(CC(=O)O)CCN(CC(=O)O)CC2)[n+]1[O-]]

According to procedure in Example 1, reaction of starting compound B (378 mg, 0.635 mmol), 2-(chloromethyl)-6-methylpyridine 1-oxide (100 mg, 0.635 mmol), anhydrous potassium carbonate (351 mg, 2.54 mmol) in acetonitrile (20 mL) gave analogously 467 mg of the product as a white fluffy solid (0.590 mmol, 93% yield relative to B).

$^1$H NMR (D$_2$O with internal dioxane reference, 95° C., 500 MHz): $\delta_H$ 2.56 (CH$_3$, s, 3H); 3.23-3.29 (cycle, m, 4H); 3.29-3.41 (cycle, m, 8H); 3.41-3.48 (cycle, m, 4H); 3.59 (CH$_2$—COOH, s, 4H); 3.98 (CH$_2$—COOH, s, 2H); 4.59 (CH$_2$-arom., s, 2H); 7-57-7.69 (arom., m, 3H). $^{13}$C{$^1$H} NMR (D$_2$O with internal dioxane reference, 95° C., 125 MHz): $\delta_C$ 17.4 (CH$_3$, s); 49.5 (cycle, s); 49.9 (cycle, s); 51.5 (cycle, s); 51.6 (cycle, s); 54.1 (CH$_2$—COOH, s); 55.0 (CH$_2$-arom., s); 55.7 (CH$_2$—COOH, s); 127.6 (arom., s); 129.4 (arom., s); 130.6 (arom., s); 142.1 (arom., s); 151.7 (arom., s); 170.5 (CO, s); 172.2 (CO, s).

HRMS (ESI) m/z: [(M–H)$^-$] (C$_{21}$H$_{32}$N$_5$O$_7$) calculated: 466.2307, found: 466.2308. Elem. analysis: M·2.6TFA·1.5H$_2$O, calculated: C (39.8), H (4.9), N (8.9), F (18.7), found: C (39.6), H (4.7), N (8.7), F (18.7).

Example 17: Preparation of 4-carboxy-2-((4,7,10-tris(carboxymethyl)-1,4,7,10-tetraazacyclododecan-1-yl)methyl)pyridine 1-oxide (17)

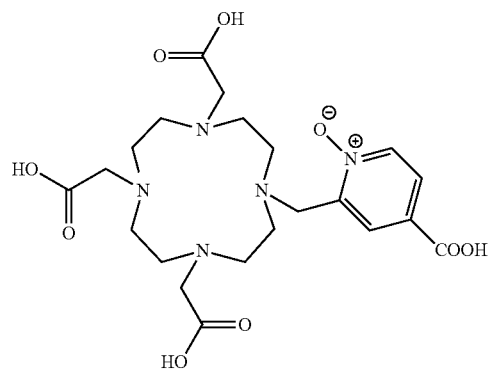 [SMILES: CCCN(CCN(CCN(CCNCC(=O)O)CC(=O)O)Cc1cc(C(=O)O)cc[n+]1[O-])CC(=O)O]

Compound was synthesized according to published procedure [Polasek M. et al. (2009), *Inorg. Chem.* 48(2), 455-465]. NMR and MS spectra agreed with those reported in literature.

Example 18: Preparation of 2-((4,7,10-tris(carboxymethyl)-1,4,7,10-tetraazacyclododecan-1-yl)methyl)pyridine 1-oxide (18)

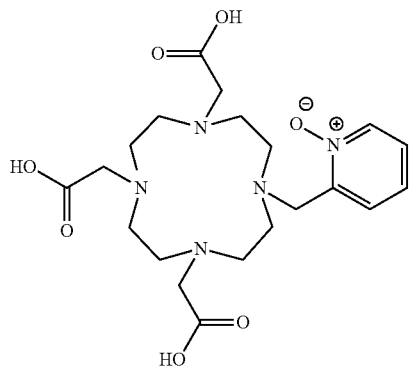 [SMILES: CCCN(CCN(CCN(CCNCC(=O)O)CC(=O)O)Cc1cccc[n+]1[O-])CC(=O)O]

Compound was synthesized according to published procedure [Polasek M. et al. (2009), *Inorg. Chem.* 48(2), 455-465]. NMR and MS spectra agreed with those reported in literature.

Example 19: Preparation of 4-chloro-2-(chloromethyl)pyridine 1-oxide (19a)

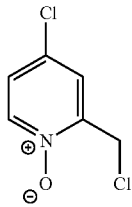

4-chloro-2-(chloromethyl)pyridine hydrochloride (200 mg, 1.02 mmol) was dissolved in chloroform (15 mL) and cooled in water/ice bath. m-chloroperoxobenzoic acid (77%, 350 mg, 1.56 mmol) was added and the reaction mixture was stirred for 24 hours while letting to warm up to room temperature. The solvent was evaporated on rotary evaporator and the residue was purified by flash chromatography on silica in 5% methanol/95% dichloromethane mixture, giving 143 mg of the product as white solid (0.803 mmol, 79% yield).

$^1$H NMR (CDCl$_3$, 25° C., 500 MHz): δ$_H$ 4.90 (CH$_2$, s, 2H); 7.26 (arom., dd, 1H, $^3$J$_{HH}$=7 Hz, $^4$J$_{HH}$=3 Hz); 7.64 (arom., d, 1H, $^4$J$_{HH}$=3 Hz); 8.20 (arom., d, 1H, $^3$J$_{HH}$=7 Hz); $^{13}$C{$^1$H} NMR (CDCl$_3$, 25° C., 125 MHz): δ$_C$ 39.6 (CH$_2$, s); 125.6 (arom., s); 125.9 (arom., s); 132.4 (arom., s); 140.2 (arom., s); 148.7 (arom., s).

HRMS (ESI) m/z: [(M+H)$^+$] (C$_6$H$_6$Cl$_2$NO) calculated: 177.9821, found: 177.9820.

Preparation of 4-chloro-2-((4,7,10-tris(carboxymethyl)-1,4,7,10-tetraazacyclododecan-1-yl)methyl)pyridine 1-oxide (19)

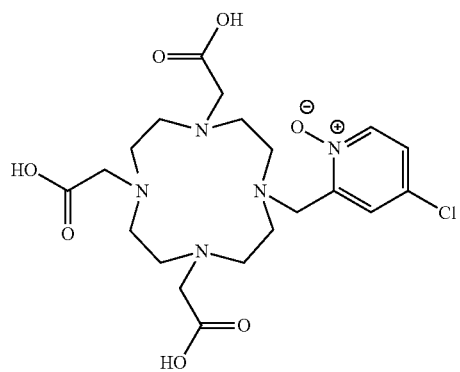 [SMILES: CCCN(CCN(CCN(CCNCC(=O)O)CC(=O)O)Cc1cc(Cl)cc[n+]1[O-])CC(=O)O]

According to procedure in Example 1, reaction of starting compound B (400 mg, 0.672 mmol), 4-chloro-2-(chloromethyl)pyridine 1-oxide (143 mg, 0.803 mmol), anhydrous potassium carbonate (370 mg, 2.68 mmol) in acetonitrile (20 mL) gave analogously 247 mg of the product as a white fluffy solid (0.332 mmol, 49% yield relative to B).

$^1$H NMR (D$_2$O with internal dioxane reference, 95° C., 500 MHz): δ$_H$ 3.25-3.39 (cycle, m, 12H); 3.39-3.45 (cycle, m, 4H); 3.72 (CH$_2$—COOH, s, 4H); 3.90 (CH$_2$—COOH, s, 2H); 4.47 (CH$_2$-arom., s, 2H); 7.70 (arom., dd, 1H, $^3$J$_{HH}$=7 Hz, $^4$J$_{HH}$=3 Hz); 7.88 (arom., d, 1H, $^4$J$_{HH}$=3 Hz); 8.34 (arom., d, 1H, $^3$J$_{HH}$=7 Hz). $^{13}$C{$^1$H} NMR (D$_2$O with internal dioxane reference, 95° C., 125 MHz): 50.4 (cycle, s); 50.5 (cycle, s); 51.0 (cycle, s); 51.1 (cycle, s); 53.3 (CH$_2$-arom., s); 54.4 (CH$_2$—COOH, s); 55.3 (CH$_2$—COOH, s); 128.7 (arom., s); 130.0 (arom., s); 137.6 (arom., s); 141.7 (arom., s); 144.4 (arom., s); 171.5 (CO, s); 171.6 (CO, s).

HRMS (ESI) m/z: [(M+H)$^+$] (C$_{20}$H$_{31}$ClN$_5$O$_7$) calculated: 488.1907, found: 488.1908.

Elem. analysis: M·1.8TFA·2.8H$_2$O, calculated: C (38.1), H (5.1), N (9.4), F (13.8), found: C (38.3), H (4.6), N (9.0), F (13.3).

Example 20: Preparation of 2-((4,7,10-tris(carboxymethyl)-1,4,7,10-tetraazacyclododecan-1-yl)methyl)quinoline 1-oxide (20)

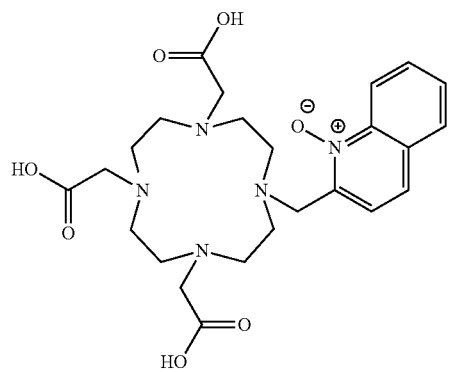 [SMILES: CCCN(CCN(CCN(CCNCC(=O)O)CC(=O)O)Cc1ccc2ccccc2[n+]1[O-])CC(=O)O]

According to procedure in Example 1, reaction of starting compound B (126 mg, 0.212 mmol), 2-(chloromethyl)quinoline 1-oxide (45 mg, 0.232 mmol), anhydrous potassium carbonate (117 mg, 0.847 mmol) in acetonitrile (10 mL) gave analogously 111 mg of the product as a white fluffy solid (0.150 mmol, 71% yield relative to B).

HRMS (ESI) m/z: [(M+Na)$^+$] (C$_{24}$H$_{33}$N$_5$NaO$_7$) calculated: 526.2283, found: 526.2280.

Elem. analysis: M·1.7TFA·2.4H$_2$O, calculated: C (44.4), H (5.4), N (9.5), F (13.1), found: C (44.2), H (4.9), N (9.0), F (12.9).

Example 21: Preparation of 1-(bromomethyl)isoquinoline 2-oxide (21a)

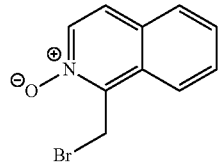 [SMILES: [O-][n+]1ccc2ccccc2c1CBr]

1-(bromomethyl)isoquinoline (150 mg, 0.675 mmol) was dissolved in chloroform (15 mL) and cooled in water-ice bath. m-chloroperoxobenzoic acid (77%, 0.230 g, 1.03 mmol) was added while stirring. The reaction mixture was let to gradually warm up to room temperature and stirred for 24 hours. The solvent was evaporated and the residue was purified by column chromatography on silica in methanol/ethyl acetate mixture. Fractions containing the product were evaporated to give 102 mg of product as pale yellow solid (0.430 mmol, 64% yield relative to 1-(bromomethyl)isoquinoline).

$^1$H NMR (CDCl$_3$, 25° C., 500 MHz): δ$_H$ 5.17 (CH$_2$-arom., s, 2H); 7.61 (arom., ddd, 1H, $^3$J$_{HH}$=8 Hz, $^3$J$_{HH}$=7 Hz, $^4$J$_{HH}$=1 Hz); 7.64 (arom., d, 1H, $^3$J$_{HH}$=7 Hz); 7.73 (arom., ddd, 1H, $^3$J$_{HH}$=9 Hz, $^3$J$_{HH}$=7 Hz, $^4$J$_{HH}$=1 Hz); 7.80-7.83 (arom., m, 1H); 7.95 (arom., ddd, 1H, $^3$J$_{HH}$=9 Hz, $^4$J$_{HH}$=2 Hz, $^4$J$_{HH}$=1 Hz); 8.19 (arom., d, 1H, $^3$J$_{HH}$=7 Hz); $^{13}$C{$^1$H}NMR (CDCl$_3$, 25° C., 125 MHz): δ$_C$ 20.9 (CH$_2$-arom., s); 122.9 (arom., s); 124.0 (arom., s); 127.6 (arom., s); 127.8 (arom., s); 128.6 (arom., s); 128.8 (arom., s); 129.9 (arom., s); 136.9 (arom., s); 143.1 (arom., s).

HRMS (ESI) m/z: [(M+H)⁺] ($C_{10}H_9BrNO$) calculated: 237.9862, found: 237.9863.

Preparation of 1-((4,7,10-tris(carboxymethyl)-1,4,7,10-tetraazacyclododecan-1-yl)methyl)isoquinoline 2-oxide (21)

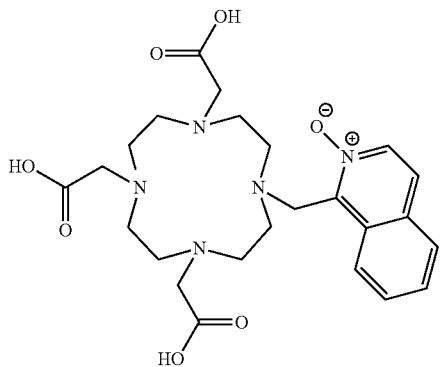 [SMILES: CCCN(CCN(CCN(CCNCC(=O)O)CC(=O)O)Cc1c2ccccc2cc[n+]1[O-])CC(=O)O]

According to procedure in Example 1, reaction of starting compound B (159 mg, 0.267 mmol), anhydrous potassium carbonate (150 mg, 1.09 mmol) and 1-(bromomethyl)isoquinoline 2-oxide (76 mg, 0.321 mmol) gave analogously 39 mg of the product as a white fluffy solid (47 mmol, 17% yield relative to B).

¹H NMR (D₂O with internal dioxane reference, 95° C., 500 MHz): $\delta_H$ 3.21-3.28 (cycle, m, 4H); 3.28-3.36 (cycle, m, 4H); 3.38-3.51 (cycle and CH₂—COOH, m, 12H); 3.98 (CH₂—COOH, s, 2H); 5.09 (CH₂-arom., s, 2H); 7.90 (arom., ddd, 1H, $^3J_{HH}$=8 Hz, $^3J_{HH}$=7 Hz, $^4J_{HH}$=1 Hz); 7.96 (arom., ddd, 1H, $^3J_{HH}$=9 Hz, $^3J_{HH}$=7 Hz, $^4J_{HH}$=1 Hz); 8.13 (arom., dd, 1H, $^3J_{HH}$=8 Hz, $^4J_{HH}$=1 Hz); 8.17 (arom., d, 1H, $^3J_{HH}$=7 Hz); 8.24 (arom., dd, 1H, $^3J_{HH}$=9 Hz, $^4J_{HH}$=1 Hz); 8.30 (arom., d, 1H, $^3J_{HH}$=7 Hz). ¹³C{¹H} NMR (D₂O with internal dioxane reference, 95° C., 125 MHz): 49.3 (cycle, s); 49.8 (cycle, s); 50.8 (CH₂-arom., s); 51.9 (cycle, s); 52.0 (cycle, s); 54.4 (CH₂—COOH, s); 56.4 (CH₂—COOH, s); 123.5 (arom., s); 127.6 (arom., s); 129.1 (arom., s); 129.2 (arom., s); 131.5 (arom., s); 131.7 (arom., s); 132.2 (arom., s); 136.0 (arom., s); 139.0 (arom., s); 170.5 (CO, s); 172.7 (CO, s).

HRMS (ESI) m/z: [(M+H)⁺] ($C_{24}H_{34}N_5O_7$) calculated: 504.2453, found: 504.2454.

Elem. analysis: M·2.3TFA·3.2H₂O, calculated: C (41.7), H (5.1), N (8.5), F (15.9), found: C (41.4), H (4.7), N (8.4), F (15.7).

Example 22: Preparation of 3-(bromomethyl)isoquinoline 2-oxide (22a)

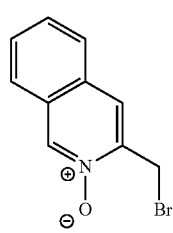 [SMILES: [O-][n+]1cc2ccccc2cc1CBr]

3-(bromomethyl)isoquinoline (211 mg, 0.950 mmol) was dissolved in dichloromethane (20 mL) and cooled in water-ice bath. m-chloroperoxobenzoic acid (77%, 0.320 g, 1.43 mmol) was added while stirring. The reaction mixture was let to gradually warm up to room temperature and stirred for 4 hours. The reaction mixture was extracted with saturated sol. of NaHCO₃ (2×20 mL) and the organic phase was dried with anhydrous NaSO₄. The solvent was evaporated to give 220 mg of product as pale yellow solid (0.924 mmol, 97% yield relative to 3-(bromomethyl)isoquinoline).

¹H NMR (CDCl₃, 25° C., 500 MHz): $\delta_H$ 4.85 (CH₂-arom., s, 2H); 7.54-7.67 (arom., m, 2H); 7.67-7.83 (arom., m, 2H); 7.94 (arom., s, 1H); 8.87 (arom., s, 1H). ¹³C{¹H} NMR (CDCl₃, 25° C., 125 MHz): $\delta_C$ 26.0 (CH₂-arom., s); 124.9 (arom., s); 125.0 (arom., s); 126.8 (arom., s); 129.0 (arom., s); 129.3 (arom., s); 129.4 (arom., s); 129.8 (arom., s); 137.1 (arom., s); 144.4 (arom., s). HRMS (ESI) m/z: [(M+H)⁺] ($C_{10}H_9BrNO$) calculated: 237.9862, found: 237.9863.

Preparation of 3-((4,7,10-tris(carboxymethyl)-1,4,7,10-tetraazacyclododecan-1-yl)methyl)isoquinoline 2-oxide (22)

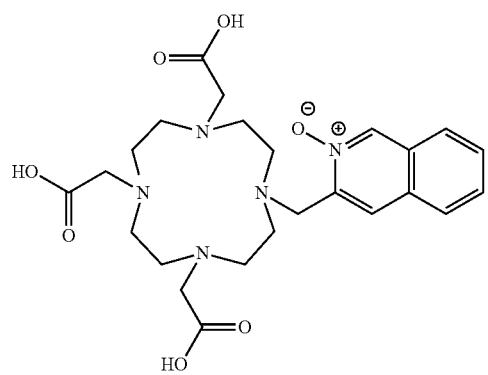 [SMILES: CCCN(CCN(CCN(CCNCC(=O)O)CC(=O)O)Cc1cc2ccccc2c[n+]1[O-])CC(=O)O]

According to procedure in Example 1, reaction of starting compound B (200 mg, 0.336 mmol), anhydrous potassium carbonate (186 mg, 1.35 mmol) and 3-(bromomethyl)isoquinoline 2-oxide (80 mg, 0.336 mmol) in acetonitrile (10 mL) gave analogously 63 mg of the product as a white fluffy solid (83 mmol, 25% yield relative to B).

HRMS (ESI) m/z: [(M+H)⁺] ($C_{24}H_{34}N_5O_7$) calculated: 504.2453, found: 504.2455.

Elem. analysis: M·2.1TFA·1.1H₂O, calculated: C (44.4), H (4.9), N (9.2), F (15.7), found: C (44.1), H (4.6), N (8.9), F (15.4).

Example 23: Preparation of 2,2',2"-(10-(2-hydroxybenzyl)-1,4,7,10-tetraazacyclododecane-1,4,7-triyl)triacetic acid (23)

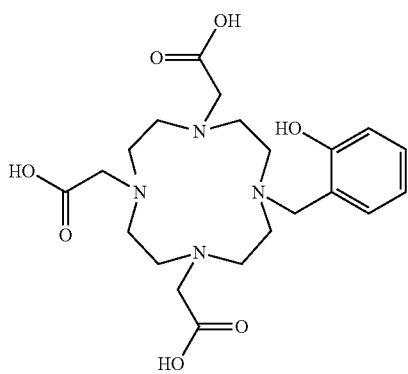 [SMILES: CCCN(CCN(CCN(CCNCC(=O)O)CC(=O)O)Cc1ccccc1O)CC(=O)O]

Starting compound B (400 mg, 0.672 mmol) and anhydrous potassium carbonate (371 mg, 2.69 mmol) were placed into a 50 mL flask under argon atmosphere and acetonitrile (20 mL) was added. 2-(chloromethyl)phenyl acetate (136 mg, 0.739 mmol) was dissolved in acetonitrile (1 mL) and added to the mixture. The reaction mixture was stirred under argon for 24 hours at room temperature. The solids were filtered off and distilled water (20 mL) was added to the filtrate. Removal of the acetate protective group followed by adding 2 M sodium hydroxide (0.668 mL, 1.34 mmol) and stirring at RT for 3 hours. After completion (followed by LC-MS), the reaction mixture was acidified with trifluoroacetic acid (0.200 mL, 2.59 mmol) and evaporated on rotary evaporator. The residue was purified on preparative HPLC (C18 column, acetonitrile/water gradient with 0.1% trifluoroacetic acid in the mobile phase). Fractions containing the intermediate with deprotected phenolic group were pooled, evaporated and dried in high vacuum. The residue was dissolved in neat trifluoroacetic acid (5 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 366 mg of the product as a white fluffy solid (0.537 mmol, 80% yield relative to B).

$^1$H NMR (D$_2$O with internal dioxane reference, 95° C., 500 MHz): $\delta_H$ 2.98-3.36 (cycle, m, 8H); 3.38 (CH$_2$—COOH, s, 4H); 3.40-3.64 (cycle, m, 8H); 4.19 (CH$_2$—COOH, s, 2H); 4.52 (CH$_2$-arom., s, 2H); 7.02 (arom., dd, 1H, $^3J_{HH}$=8 Hz, $^4J_{HH}$=1 Hz); 7.09 (arom., td, 1H, $^3J_{HH}$=8 Hz, $^4J_{HH}$=1 Hz); 7.42-7.48 (arom., m, 2H); $^{13}$C{$^1$H} NMR (D$_2$O with internal dioxane reference, 95° C., 125 MHz): $\delta_C$ 47.9 (cycle, s); 48.9 (cycle, s); 51.2 (cycle, s); 52.8 (cycle, s); 53.4 (CH$_2$—COOH, s); 55.6 (CH$_2$-arom., s); 56.1 (CH$_2$—COOH, s); 116.4 (arom., s); 116.8 (arom., s); 121.9 (arom., s); 133.2 (arom., s); 133.5 (arom., s); 155.8 (arom., s); 169.1 (CO, s); 174.0 (CO, s).

HRMS (ESI) m/z: [(M–H)$^-$] (C$_{21}$H$_{31}$N$_4$O$_7$) calculated: 451.2198, found: 451.2192.

Elem. analysis: M·1.6TFA·2.6H$_2$O, calculated: C (39.4), H (4.7), N (8.4), F (21.3), found: C (39.3), H (4.5), N (8.2), F (21.1).

Example 24: Preparation of 2-(bromomethyl)-6-methylphenyl acetate (24a)

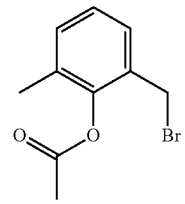

2,6-dimethylphenyl acetate (1.98 g, 12.1 mmol), N-bromosuccinimide (2.4 g, 13.5 mmol) and 2,2'-Azobis(2-methylpropionitrile) (100 mg, 0.609 mmol) were dissolved in tetrachloromethane (40 mL) in a 100 mL flask. The reaction mixture was heated under reflux for 1 hour. The solvent was evaporated on rotary evaporator. The residue was chromatographed on a 50 g silica column with petroleum ether as the mobile phase. Fraction containing the product were concentrated on rotary evaporator, giving 2.1 g of product as a colorless oil (8.6 mmol, 71% yield).

$^1$H NMR (CDCl$_3$, 25° C., 500 MHz): $\delta_H$ 2.20 (CH$_3$-arom., s, 3H); 2.42 (CH$_3$—CO, s, 3H); 4.42 (CH$_2$-arom., s, 2H); 7.12-7.19 (arom., m, 1H); 7.21-7.30 (arom., m, 2H). $^{13}$C{$^1$H} NMR (CDCl$_3$, 25° C., 125 MHz): $\delta_C$ 16.4 (CH$_3$-arom., s); 20.7 (CH$_3$—CO, s); 28.1 (CH$_2$— arom., s); 126.4 (arom., s); 128.6 (arom., s); 129.9 (arom., s); 131.6 (arom., s); 131.8 (arom., s); 148.0 (arom., s); 168.5 (CO, s).

HRMS (EI) m/z: [M$^+$] (C$_{10}$H$_{11}$BrO$_2$) calculated: 241.9942, found: 241.9944.

Preparation of 2,2',2"-(10-(2-hydroxy-3-methylbenzyl)-1,4,7,10-tetraazacyclododecane-1,4,7-triyl)triacetic acid (24)

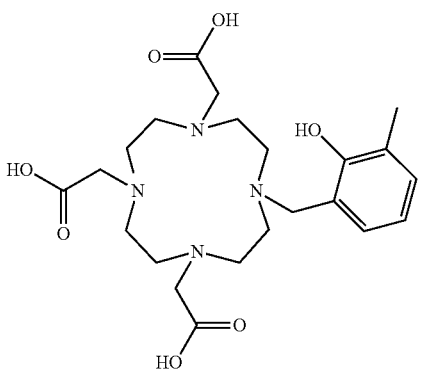 [SMILES: CCCN(CCN(CCN(CCNCC(=O)O)CC(=O)O)Cc1cccc(C)c1O)CC(=O)O]

According to procedure in Example 23, reaction of starting compound B (400 mg, 0.672 mmol), anhydrous potassium carbonate (371 mg, 2.69 mmol) and 2-(bromomethyl)-6-methylphenyl acetate (196 mg, 0.807 mmol) in acetonitrile (20 mL) was carried out, followed by treatment with 2 M sodium hydroxide (1.11 mL, 2.22 mmol) for 4 hours, neutralization with trifluoroacetic acid (0.230 mL, 2.98 mmol) and further processing as in Example 23, giving analogously 293 mg of the product as a white fluffy solid (427 mmol, 64% yield relative to B).

$^1$H NMR (D$_2$O with internal dioxane reference, 95° C., 500 MHz): $\delta_H$ 2.32 (CH$_3$, s, 3H); 3.05-3.30 (cycle, m, 8H);

3.39 (CH$_2$—COOH, s, 4H); 3.44-3.52 (cycle, m, 4H); 3.52-3.59 (cycle, m, 4H); 4.08 (CH$_2$—COOH, s, 2H); 4.55 (CH$_2$-arom., s, 2H); 7.06 (arom., t, 1H, $^3J_{HH}$=8 Hz); 7.31 (arom., dd, 1H, $^3J_{HH}$=8 Hz, $^3J_{HH}$=2 Hz); 7.39 (arom., dd, 1H, $^3J_{HH}$=8 Hz, $^3J_{HH}$=2 Hz); $^{13}$C{$^1$H} NMR (D$_2$O with internal dioxane reference, 95° C., 125 MHz): δ$_C$ 25.7 (CH$_3$, s); 47.8 (cycle, s); 48.7 (cycle, s); 51.4 (cycle, s); 52.6 (cycle, s); 53.3 (CH$_2$—COOH, s); 56.0 (CH$_2$-arom., s); 57.1 (CH$_2$—COOH, s); 117.1 (arom., s); 122.2 (arom., s); 126.5 (arom., s); 131.1 (arom., s); 134.5 (arom., s); 153.6 (arom., s); 169.7 (CO, s); 173.7 (CO, s). HRMS (ESI) m/z: [(M−H)$^-$] (C$_{22}$H$_{33}$N$_4$O$_7$) calculated: 465.2355, found: 465.2349. Elem. analysis: M·1.9TFA·0.2H$_2$O, calculated: C (45.1), H (5.3), N (8.2), F (15.8), found: C (45.1), H (5.8), N (8.0), F (16.2).

Example 25: Preparation of 2-(bromomethyl)-5-methylphenyl acetate (25a)

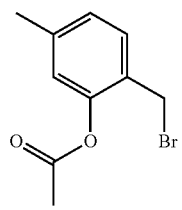

According to procedure for preparation of 2-(bromomethyl)-6-methylphenyl acetate in Example 24, reaction of 2,5-dimethylphenyl acetate (1.98 g, 12.1 mmol) gave analogously 0.882 g of product as a colorless oil (3.63 mmol, 30% yield).

$^1$H NMR (CDCl$_3$, 25° C., 500 MHz): δ$_H$ 2.33-2.39 (CH$_3$-arom. and CH$_3$—CO, m, 6H); 4.40 (CH$_2$-arom., s, 2H); 6.94 (arom., s, 1H); 7.03 (arom., d, 1H, $^3J_{HH}$=8 Hz). 7.29 (arom., d, 1H, $^3J_{HH}$=8 Hz). $^{13}$C{$^1$H} NMR (CDCl$_3$, 25° C., 125 MHz): 21.1 (CH$_3$—CO, s); 21.4 (CH$_3$-arom., s); 28.0 (CH$_2$-arom., s); 123.8 (arom., s); 126.7 (arom., s); 127.3 (arom., s); 130.7 (arom., s); 140.6 (arom., s); 149.0 (arom., s); 169.2 (CO, s).

HRMS (EI) m/z: [M$^+$] (C$_{10}$H$_{11}$BrO$_2$) calculated: 241.9942, found: 241.9941.

Preparation of 2,2',2''-(10-(2-hydroxy-4-methylbenzyl)-1,4,7,10-tetraazacyclododecane-1,4,7-triyl)triacetic acid (25)

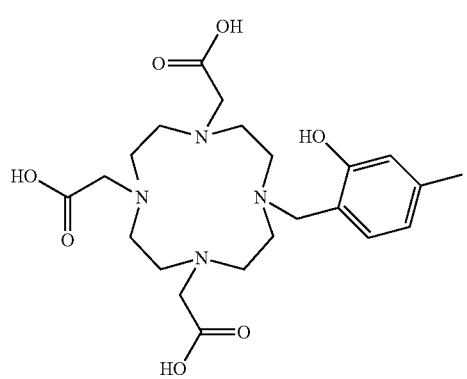 [SMILES: CCCN(CCN(CCN(CCNCC(=O)O)CC(=O)O)Cc1ccc(C)cc1O)CC(=O)O]

According to procedure in Example 23, reaction of starting compound B (400 mg, 0.672 mmol), anhydrous potassium carbonate (371 mg, 2.69 mmol) and 2-(bromomethyl)-5-methylphenyl acetate (196 mg, 0.807 mmol) in acetonitrile (20 mL) was carried out, followed by treatment with 2 M sodium hydroxide (1.11 mL, 2.22 mmol) for 4 hours, neutralization with trifluoroacetic acid (0.230 mL, 2.98 mmol) and further processing as in Example 23, giving analogously 325 mg of the product as a white fluffy solid (0.464 mmol, 69% yield relative to B).

$^1$H NMR (DMSO, 25° C., 500 MHz): 2.24 (CH$_3$, 3H, s); 2.94-3.15 (cycle, m, 8H); 3.17-3.51 (cycle+CH$_2$—COOH, m, 12H); 4.08 (CH$_2$—COOH, bs, 2H); 4.39 (CH$_2$-arom, bs, 2H); 6.07-6.72 (arom., m, 1H); 6.78 (arom., bs, 1H); 7.31 (arom., d, 1H, $^3J_{HH}$=8 Hz); $^{13}$C{$^1$H} NMR (DMSO, 25° C., 125 MHz): δ$_C$ 21.5 (CH$_3$, s); 48.0 (cycle, bs); 48.3 (cycle, bs); 49.7 (cycle, bs); 51.7 (cycle, bs); 52.0 (CH$_2$-arom., s); 53.0 (CH$_2$—COOH, s); 54.9 (CH$_2$—COOH, s); 113.0 (arom., s); 116.9 (arom., s); 121.0 (arom., s); 133.3 (arom., s); 141.8 (arom., s); 157.1 (arom., s); 168.7 (CO, s); 172.9 (CO, s). HRMS (ESI) m/z: [(M–H)$^-$] (C$_{22}$H$_{33}$N$_4$O$_7$) calculated: 465.2355, found: 465.2350. Elem. analysis: M·1.7TFA·2.2H$_2$O, calculated: C (43.6), H (5.8), N (8.0), F (13.8), found: C (43.5), H (5.4), N (7.8), F (13.5).

Example 26: Preparation of 2,2',2''-(10-(2-hydroxy-5-(methoxycarbonyl)benzyl)-1,4,7,10-tetraazacyclododecane-1,4,7-triyl)triacetic acid (26)

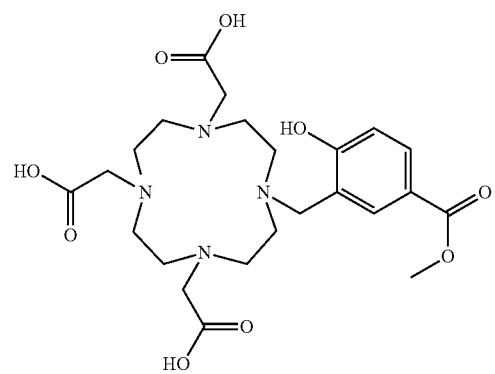 [SMILES: CCCN(CCN(CCN(CCNCC(=O)O)CC(=O)O)Cc1cc(C(=O)OC)ccc1O)CC(=O)O]

According to procedure in Example 23, reaction of starting compound B (207 mg, 0.348 mmol), anhydrous potassium carbonate (193 mg, 1.40 mmol) and methyl 4-acetoxy-3-(bromomethyl)benzoate (120 mg, 0.418 mmol) in acetonitrile (15 mL) was carried out, followed by treatment with 2 M sodium hydroxide (0.627 mL, 1.25 mmol) for 3 hours, neutralization with trifluoroacetic acid (0.193 mL, 2.51 mmol) and further processing as in Example 23, giving analogously 115 mg of the product as a white fluffy solid (0.155 mmol, 45% yield relative to B).

HRMS (ESI) m/z: [(M–H)$^-$] (C$_{23}$H$_{33}$N$_4$O$_9$) calculated: 509.2253, found: 509.2254. Elem. analysis: M·1.7TFA·2.2H$_2$O, calculated: C (42.6), H (5.4), N (7.5), F (13.0), found: C (42.3), H (5.1), N (7.2), F (13.0).

Example 27: Preparation of 2,2',2''-(10-(2-hydroxy-5-nitrobenzyl)-1,4,7,10-tetraazacyclododecane-1,4,7-triyl)triacetic acid (27)

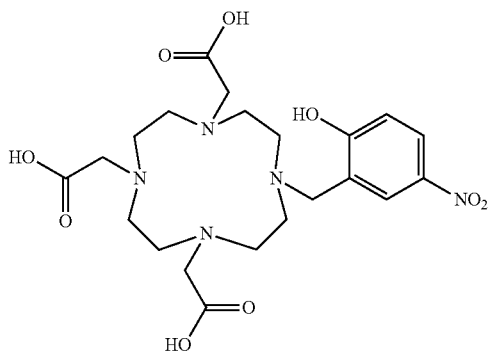 [SMILES: O=C(O)CN1CCN(CC(=O)O)CCN(Cc2cc([N+](=O)[O-])ccc2O)CCN(CC(=O)O)CC1]

According to procedure in Example 1, reaction of starting compound B (400 mg, 0.672 mmol), 2-(bromomethyl)-4-nitrophenol (203 mg, 0.874 mmol) and anhydrous potassium carbonate (371 mg, 2.69 mmol) in acetonitrile (20 mL) extended to 4 days at room temperature gave analogously 123 mg of the product as a white fluffy solid (0.171 mmol, 25% yield relative to B).

$^1$H NMR (DMSO, 25° C., 500 MHz): 2.91-3.41 (cycle, m, 16H); 3.51 (CH$_2$—COOH, bs, 4H); 4.00 (CH$_2$—COOH, bs, 2H); 4.42 (CH$_2$-arom, bs, 2H); 7.11 (arom., d, 1H, $^3J_{HH}$=9 Hz); 8.21 (arom., dd, 1H, $^3J_{HH}$=9 Hz, $^4J_{HH}$=3 Hz); 8.45 (arom., d, 1H, $^4J_{HH}$=3 Hz); $^{13}$C{$^1$H} NMR (DMSO, 25° C., 125 MHz): δ$_C$ 48.8 (cycle, bs); 48.9 (cycle, bs); 49.7 (cycle, bs); 51.4 (cycle, bs); 51.6 (CH$_2$-arom., s); 53.1 (CH$_2$—COOH, s); 54.7 (CH$_2$—COOH, s); 116.9 (arom., s); 118.0 (arom., s); 127.7 (arom., s); 130.2 (arom., s); 139.7 (arom., s); 164.4 (arom., s); 169.3 (CO, s); 172.6 (CO, s). HRMS (ESI) m/z: [(M−H)$^-$] (C$_{21}$H$_{30}$N$_5$O$_9$) calculated: 496.2049, found: 496.2044. Elem. analysis: M·2.3TFA·2.8H$_2$O, calculated: C (40.0), H (5.4), N (9.7), F (11.9), found: C (39.5), H (4.8), N (9.3), F (11.3).

Example 28: Preparation of 2,2',2''-(10-(2-methoxybenzyl)-1,4,7,10-tetraazacyclododecane-1,4,7-triyl)triacetic acid (28)

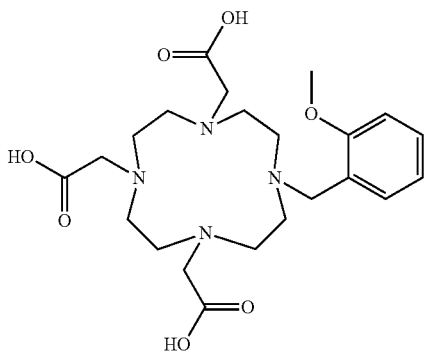 [SMILES: COc1ccccc1CN1CCN(CC(=O)O)CCN(CC(=O)O)CCN(CC(=O)O)CC1]

According to procedure in Example 1, reaction of starting compound B (400 mg, 0.672 mmol), 1-(chloromethyl)-2-methoxybenzene (116 mg, 0.739 mmol) and anhydrous potassium carbonate (371 mg, 2.69 mmol) in acetonitrile (20 mL) gave analogously 356 mg of the product as a white fluffy solid (0.504 mmol, 75% yield relative to B).

$^1$H NMR (D$_2$O with internal dioxane reference, 95° C., 500 MHz): δ$_H$ 3.01-3.34 (cycle, m, 8H); 3.34-3.48 (cycle, m, 8H); 3.48-3.65 (CH$_2$—COOH, m, 4H); 3.93 (CH$_3$, s, 3H); 4.18 (CH$_2$—COOH, s, 2H); 4.55 (CH$_2$-arom., s, 2H); 7.15 (arom., td, 1H, $^3J_{HH}$=8 Hz, $^4J_{HH}$=1 Hz); 7.20 (arom., dd, 1H, $^3J_{HH}$=8 Hz, $^4J_{HH}$=1 Hz); 7.48 (arom., dd, 1H, $^3J_{HH}$=8 Hz, $^4J_{HH}$=2 Hz); 7.60 (arom., ddd, 1H, $^3J_{HH}$=8 Hz, $^3J_{HH}$=8 Hz, $^4J_{HH}$=2 Hz); $^{13}$C{$^1$H} NMR (D$_2$O with internal dioxane reference, 95° C., 125 MHz): δ$_C$ 48.3 (cycle, s); 49.1 (cycle, s); 51.2 (cycle, s); 52.8 (cycle, s); 53.7 (CH$_2$—COOH, s); 55.1 (CH$_2$-arom., s); 56.1 (CH$_2$—COOH, s); 57.1 (CH$_3$, s); 113.3 (arom., s); 117.5 (arom., s); 122.4 (arom., s); 133.6 (arom., s); 133.9 (arom., s); 158.9 (arom., s); 168.8 (CO, s); 173.9 (CO, s).

HRMS (ESI) m/z: [(M−H)$^-$] (C$_{22}$H$_{33}$N$_4$O$_7$) calculated: 465.2355, found: 465.2349.

Elem. analysis: M·1.8TFA·1.9H$_2$O, calculated: C (43.6), H (5.7), N (7.9), F (14.5), found: C (43.2), H (5.1), N (7.4), F (14.4).

Example 29: Preparation of 2,2',2''-(10-((3-methoxynaphthalen-2-yl)methyl)-1,4,7,10-tetraazacyclododecane-1,4,7-triyl)triacetic acid (29)

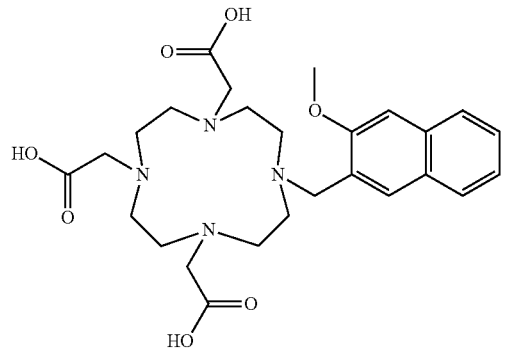 [SMILES: COc1cc2ccccc2cc1CN1CCN(CC(=O)O)CCN(CC(=O)O)CCN(CC(=O)O)CC1]

According to procedure in Example 1, reaction of starting compound B (288 mg, 0.484 mmol), 2-(chloromethyl)-3-methoxynaphthalene (100 mg, 0.484 mmol) and anhydrous potassium carbonate (267 mg, 1.93 mmol) in acetonitrile (20 mL) gave analogously 265 mg of the product as a white fluffy solid (0.344 mmol, 71% yield relative to B).

HRMS (ESI) m/z: [(M+H)$^+$] (C$_{26}$H$_{37}$N$_4$O$_7$) calculated: 517.2657, found: 517.2657.

Elem. analysis: M·1.9TFA·2.1H$_2$O, calculated: C (46.4), H (5.5), N (7.3), F (14.0), found: C (47.0), H (5.1), N (6.7), F (14.0).

Example 30: Preparation of 2,2',2''-(10-((1-methoxynaphthalen-2-yl)methyl)-1,4,7,10-tetraazacyclododecane-1,4,7-triyl)triacetic acid (30)

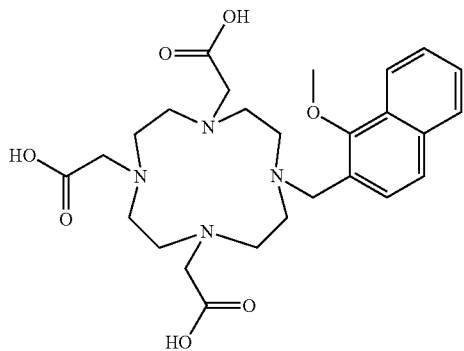 [SMILES: COc1c(CN2CCN(CC(=O)O)CCN(CC(=O)O)CCN(CC(=O)O)CC2)ccc2ccccc12]

According to procedure in Example 1, reaction of starting compound B (432 mg, 0.726 mmol), 2-(chloromethyl)-1-methoxynaphthalene (150 mg, 0.726 mmol) and anhydrous potassium carbonate (401 mg, 2.90 mmol) in acetonitrile (20 mL) gave analogously 375 mg of the product as a white fluffy solid (0.495 mmol, 68% yield relative to B).

$^1$H NMR (D$_2$O with internal dioxane reference, 95° C., 500 MHz): δ$_H$ 3.11-3.19 (cycle, m, 4H); 3.19-3.29 (cycle, m, 4H); 3.34-3.42 (CH$_2$—COOH, m, 4H); 3.42-3.48 (cycle, m, 4H); 3.50-3.56 (cycle, m, 4H); 4.05 (CH$_3$, S, 3H); 4.09 (CH$_2$—COOH, s, 2H); 4.69 (CH$_2$-arom., 2H); 7.59 (arom., d, 1H, $^3$J$_{HH}$=9 Hz); 7.65-7.75 (arom., m, 2H); 7.84 (arom., d, 1H, $^3$J$_{HH}$=9 Hz); 8.01-8.06 (arom., m, 1H); 8.16-8.21 (arom., m, 1H); $^{13}$C{$^1$H} NMR (D$_2$O with internal dioxane reference, 95° C., 125 MHz): δ$_C$ 49.1 (cycle, s); 49.5 (cycle, s); 51.2 (cycle, s); 52.4 (cycle, s); 54.1 (CH$_2$—COOH, s); 54.4 (CH$_2$-arom., s); 55.9 (CH$_2$—COOH, s); 64.0 (CH$_3$, s); 118.7 (arom., s); 123.1 (arom., s); 126.6 (arom., s); 127.7 (arom., s); 128.0 (arom., s); 128.1 (arom., s); 128.8 (arom., s); 129.2 (arom., s); 136.6 (arom., s); 156.8 (arom., s); 169.5 (CO, s); 173.6 (CO, s).

HRMS (ESI) m/z: [(M−H)$^−$] (C$_{26}$H$_{35}$N$_4$O$_7$) calculated: 515.2511, found: 515.2505.

Elem. analysis: M·1.8TFA·2.0H$_2$O, calculated: C (46.9), H (5.6), N (7.4), F (13.5), found: C (47.2), H (5.4), N (7.0), F (13.6).

Example 31: Preparation of 2,2',2''-(10-(2-carboxybenzyl)-1,4,7,10-tetraazacyclododecane-1,4,7-triyl)triacetic acid (31)

Starting compound B (400 mg, 0.672 mmol) and anhydrous potassium carbonate (371 mg, 2.68 mmol) were placed into a 50 mL flask under argon atmosphere and acetonitrile (17 mL) was added. Methyl 2-(bromomethyl)benzoate (182 mg, 0.795 mmol) was dissolved in anhydrous acetonitrile (3 mL) and added to the mixture. The reaction mixture was stirred under argon for 3 days at room temperature. The solids were filtered off and distilled water (20 mL) was added to the filtrate. Hydrolysis of methyl ester moiety followed by adding 2 M sodium hydroxide (2 mL, 4.00 mmol) and stirring at RT for 2 hours. After completion (followed by LC-MS), the reaction mixture was acidified with trifluoroacetic acid (0.3 mL, 3.92 mmol) and evaporated on rotary evaporator. The residue was purified on preparative HPLC (C18 column, acetonitrile/water gradient with 0.1% trifluoroacetic acid in the mobile phase). Fractions containing the intermediate with free benzoate group (mass 648 Da) were pooled, evaporated and dried in high vacuum. The residue was dissolved in neat trifluoroacetic acid (4 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 192 mg of the product as a white fluffy solid (0.259 mmol, 39% yield relative to B).

$^1$H NMR (DMSO, 100° C., 500 MHz): δ$_H$ 3.01-3.34 (cycle, m, 8H); 3.18-3.27 (cycle, m, 4H); 3.27-3.36 (cycle and CH$_2$—COOH, m, 8H); 4.01 (CH$_2$—COOH, s, 2H); 4.60 (CH$_2$-arom., s, 2H); 7.52-7.58 (arom., m, 1H); 7.58-7.63 (arom., m, 2H); 7.97-8.02 (arom., m, 1H); $^{13}$C{$^1$H} NMR (DMSO, 100° C., 125 MHz): δ$_C$ 48.8 (cycle, s); 49.3 (cycle, s); 50.9 (cycle, s); 51.6 (cycle, s); 52.0 (CH$_2$—COOH, s); 54.8 (CH$_2$—COOH, s); 56.8 (CH$_2$-arom., s); 129.3 (arom., s); 131.0 (arom., s); 131.6 (arom., s); 131.9 (arom., s); 132.9 (arom., s); 133.4 (arom., s); 168.5 (CO, s); 169.0 (CO, s); 170.9 (CO, s).

HRMS (ESI) m/z: [(M+Na)$^+$] (C$_{22}$H$_{32}$N$_4$NaO$_8$) calculated: 503.2112, found: 503.2113.

Elem. analysis: M·2.0TFA·1.9H$_2$O, calculated: C (42.0), H (5.1), N (7.5), F (15.3), found: C (42.3), H (4.7), N (7.1), F (15.0).

Example 32: Preparation of 2,2',2''-(10-(3-carboxybenzyl)-1,4,7,10-tetraazacyclododecane-1,4,7-triyl)triacetic acid (32)

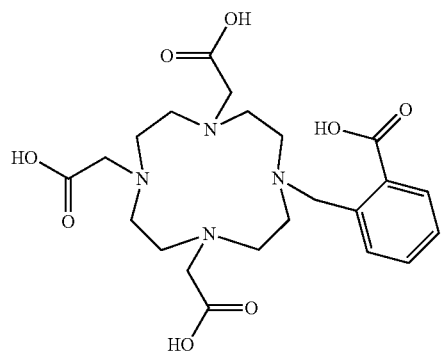 [SMILES: O=C(O)CN1CCN(CC(=O)O)CCN(Cc2ccccc2C(=O)O)CCN(CC(=O)O)CC1]

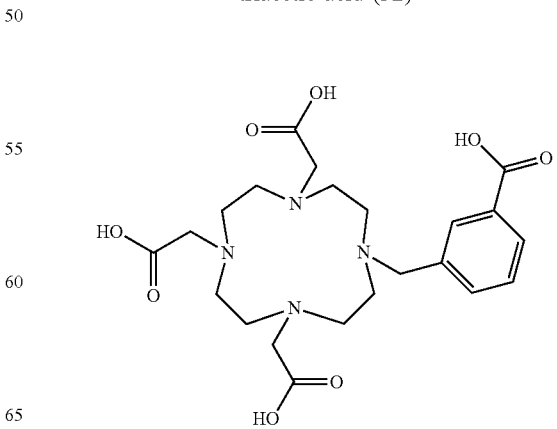

According to procedure in Example 31, reaction of starting compound B (400 mg, 0.672 mmol), anhydrous potassium carbonate (371 mg, 2.68 mmol) and methyl 3-(bromomethyl)benzoate (182 mg, 0.795 mmol) gave analogously 319 mg of the product as a white fluffy solid (0.507 mmol, 75% yield relative to B).

HRMS (ESI) m/z: [(M+Na)$^+$] ($C_{22}H_{32}N_4NaO_8$) calculated: 503.2112, found: 503.2114.

Elem. analysis: M·1.9TFA·1.9H$_2$O, calculated: C (42.4), H (5.2), N (7.7), F (14.8), found: C (42.6), H (5.6), N (7.3), F (15.2).

Example 33: Preparation of 2,2',2"-(10-(4-carboxybenzyl)-1,4,7,10-tetraazacyclododecane-1,4,7-triyl) triacetic acid (33)

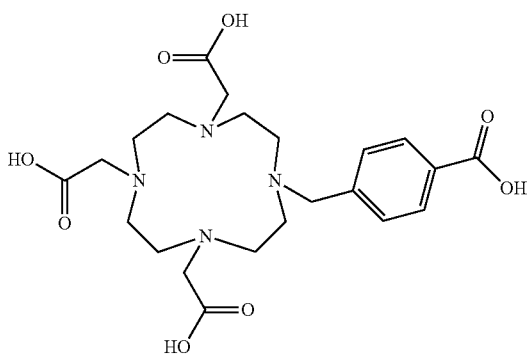 [SMILES: O=C(O)CN1CCN(CC(=O)O)CCN(Cc2ccc(C(=O)O)cc2)CCN(CC(=O)O)CC1]

According to procedure in Example 31, reaction of starting compound B (400 mg, 0.672 mmol), anhydrous potassium carbonate (371 mg, 2.68 mmol) and methyl 3-(bromomethyl)benzoate (182 mg, 0.795 mmol) gave analogously 264 mg of the product as a white fluffy solid (0.345 mmol, 51% yield relative to B).

HRMS (ESI) m/z: [(M+H)$^+$] ($C_{22}H_{33}N_4NaO_8$) calculated: 481.2293, found: 481.2293.

Elem. analysis: M·2.1TFA·2.5H$_2$O, calculated: C (41.1), H (5.2), N (7.3), F (15.6), found: C (40.8), H (4.8), N (7.6), F (15.4).

Example 34: Preparation of 2,2',2"-(10-benzyl-1,4,7,10-tetraazacyclododecane-1,4,7-triyl)triacetic acid (34)

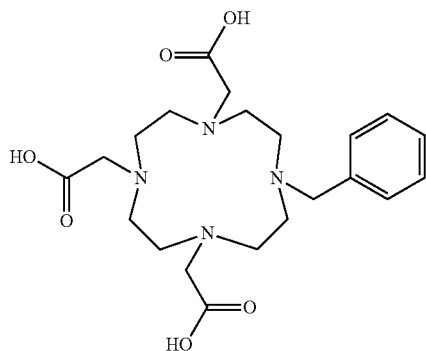 [SMILES: O=C(O)CN1CCN(CC(=O)O)CCN(Cc2ccccc2)CCN(CC(=O)O)CC1]

According to procedure in Example 1, reaction of starting compound B (400 mg, 0.671 mmol), benzyl bromide (115 mg, 0.676 mmol) and anhydrous potassium carbonate (371 mg, 2.69 mmol) in acetonitrile (20 mL) gave analogously 373 mg of the product as a white fluffy solid (0.553 mmol, 82% yield relative to B).

$^1$H NMR (D$_2$O with internal dioxane reference, 95° C., 500 MHz): $\delta_H$ 3.06-3.23 (cycle, m, 8H); 3.23-3.50 (cycle and CH$_2$—COOH, m, 8H); 3.50-3.57 (cycle, m, 4H); 4.13 (CH$_2$—COOH, s, 2H); 4.49 (CH$_2$-arom., s, 2H); 7.43-7.69 (arom., m, 5H); $^{13}$C{$^1$H} NMR (D$_2$O with internal dioxane reference, 95° C., 125 MHz): $\delta_C$ 49.2 (cycle, s); $\delta_C$ 49.3 (cycle, s); $\delta_C$ 50.8 (cycle, s); $\delta_C$ 52.5 (cycle, s); 54.1 (CH$_2$—COOH, s); 55.6 (CH$_2$—COOH, s); 59.1 (CH$_2$-arom., s); 130.0 (arom., s); 130.5 (arom., s); 131.2 (arom., s); 131.6 (arom., s); 169.3 (CO, s); 173.7 (CO, s).

HRMS (ESI) m/z: [(M−H)$^-$] ($C_{21}H_{31}N_4O_6$) calculated: 435.2249, found: 435.2251.

Elem. analysis: M·1.9TFA·1.2H$_2$O, calculated: C (44.1), H (5.4), N (8.3), F (16.0), found: C (44.4), H (5.2), N (7.9), F (16.1).

Example 35: Preparation of 2,2',2"-(10-(4-methylbenzyl)-1,4,7,10-tetraazacyclododecane-1,4,7-triyl) triacetic acid (35)

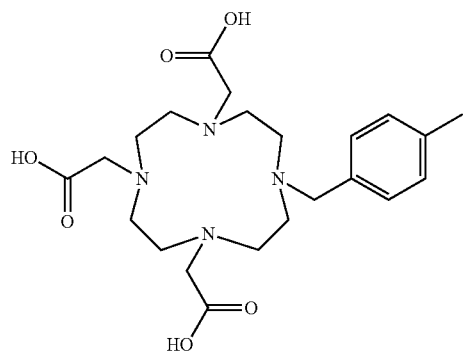 [SMILES: Cc1ccc(CN2CCN(CC(=O)O)CCN(CC(=O)O)CCN(CC(=O)O)CC2)cc1]

According to procedure in Example 1, reaction of starting compound B (400 mg, 0.671 mmol), 1-(bromomethyl)-4-methylbenzene (137 mg, 0.740 mmol) and anhydrous potassium carbonate (371 mg, 2.69 mmol) in acetonitrile (20 mL) gave analogously 262 mg of the product as a white fluffy solid (0.373 mmol, 56% yield relative to B).

HRMS (ESI) m/z: [(M−H)$^-$] ($C_{22}H_{33}N_4O_6$) calculated: 449.2406, found: 449.2400.

Elem. analysis: M·1.8TFA·2.6H$_2$O, calculated: C (43.8), H (5.9), N (8.0), F (14.6), found: C (44.1), H (5.7), N (7.7), F (14.3).

Example 36: Preparation of 2,2',2''-(10-(2-methylbenzyl)-1,4,7,10-tetraazacyclododecane-1,4,7-triyl)triacetic acid (36)

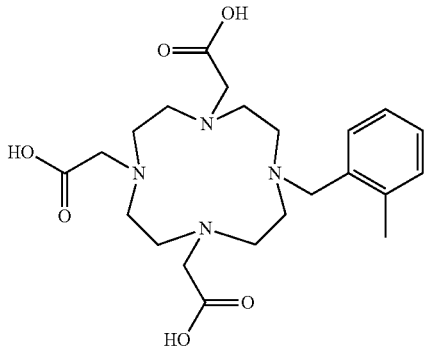 [SMILES: Cc1ccccc1CN1CCN(CC(=O)O)CCN(CC(=O)O)CCN(CC(=O)O)CC1]

According to procedure in Example 1, reaction of starting compound B (400 mg, 0.671 mmol), 1-(bromomethyl)-2-methylbenzene (140 mg, 0.757 mmol) and anhydrous potassium carbonate (371 mg, 2.69 mmol) in acetonitrile (20 mL) gave analogously 312 mg of the product as a white fluffy solid (0.466 mmol, 69% yield relative to B).

HRMS (ESI) m/z: [(M+H)$^+$] ($C_{22}H_{35}N_4O_6$) calculated: 451.2551, found: 451.2551.

Elem. analysis: M·1.6TFA·2.0H$_2$O, calculated: C (45.2), H (6.0), N (8.4), F (13.6), found: C (45.0), H (5.7), N (8.3), F (13.5).

Example 37: Preparation of 2,2',2''-(10-(4-nitrobenzyl)-1,4,7,10-tetraazacyclododecane-1,4,7-triyl)triacetic acid (37)

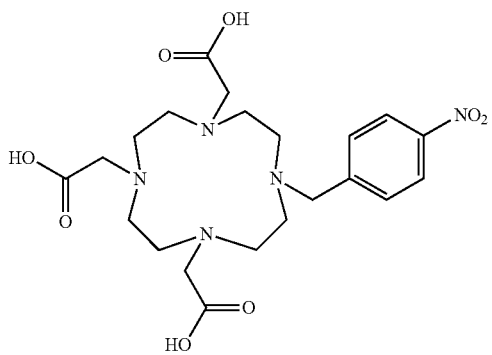 [SMILES: O=C(O)CN1CCN(CC(=O)O)CCN(Cc2ccc([N+](=O)[O-])cc2)CCN(CC(=O)O)CC1]

According to procedure in Example 1, reaction of starting compound B (400 mg, 0.671 mmol), 1-(bromomethyl)-4-nitrobenzene (158 mg, 0.731 mmol) and anhydrous potassium carbonate (371 mg, 2.69 mmol) in acetonitrile (20 mL) gave analogously 357 mg of the product as a white fluffy solid (0.494 mmol, 74% yield relative to B).

HRMS (ESI) m/z: [(M−H)$^−$] ($C_{21}H_{30}N_5O_8$) calculated: 480.2100, found: 480.2094.

Elem. analysis: M·1.8TFA·2.0H$_2$O, calculated: C (40.9), H (5.1), N (9.7), F (14.2), found: C (41.1), H (5.1), N (9.4), F (14.5).

Example 38: Preparation of 2,2',2''-(10-(2-nitrobenzyl)-1,4,7,10-tetraazacyclododecane-1,4,7-triyl)triacetic acid (38)

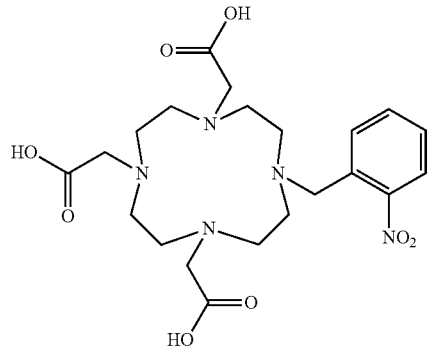 [SMILES: O=C(O)CN1CCN(CC(=O)O)CCN(Cc2ccccc2[N+](=O)[O-])CCN(CC(=O)O)CC1]

According to procedure in Example 1, reaction of starting compound B (200° C. mg, 0.336 mmol), 1-(bromomethyl)-2-nitrobenzene (84 mg, 0.389 mmol) and anhydrous potassium carbonate (139 mg, 1.01 mmol) in acetonitrile (20 mL) gave analogously 223 mg of the product as a white fluffy solid (0.310 mmol, 92% yield relative to B).

HRMS (ESI) m/z: [(M−H)$^−$] ($C_{21}H_{30}N_5O_8$) calculated: 480.2100, found: 480.2101.

Elem. analysis: M·1.9TFA·1.2H$_2$O, calculated: C (41.4), H (4.9), N (9.7), F (15.0), found: C (41.3), H (4.5), N (9.3), F (14.8).

Example 39: Preparation of 2,2',2''-(10-((perfluorophenyl)methyl)-1,4,7,10-tetraazacyclododecane-1,4,7-triyl)triacetic acid (39)

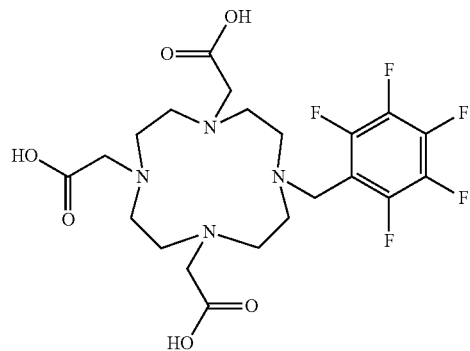 [SMILES: O=C(O)CN1CCN(CC(=O)O)CCN(Cc2c(F)c(F)c(F)c(F)c2F)CCN(CC(=O)O)CC1]

According to procedure in Example 1, reaction of starting compound B (400 mg, 0.671 mmol), 1-(bromomethyl)-2,3,4,5,6-pentafluorobenzene (193 mg, 0.739 mmol) and anhydrous potassium carbonate (371 mg, 2.69 mmol) in acetonitrile (20 mL) gave analogously 345 mg of the product as a white fluffy solid (0.454 mmol, 68% yield relative to B).

$^1$H NMR (DMSO, 100° C., 500 MHz): $\delta_H$ 2.69-2.80 (cycle, m, 4H); 2.95-3.00 (cycle, m, 4H); 3.09-3.24 (cycle, m, 8H); 3.62 (CH$_2$—COOH, s, 2H); 3.72 (CH$_2$—COOH, s, 4H); 4.03 (CH$_2$-arom., s, 2H); $^{13}$C{$^1$H} NMR (DMSO, 100° C., 125 MHz): $\delta_C$ 44.9 (CH$_2$-arom., s); 48.4 (cycle, s); 49.3 (cycle, s); 51.7 (cycle, s); 51.8 (cycle, s); 53.7 (CH$_2$—COOH, s); 54.3 (CH$_2$—COOH, s); 109.7 (arom., t, $^2J_{CF}$=20

Hz); 137.0 (arom., dm, $^1J_{CF}$=249 Hz); 140.1 (arom., dm, $^1J_{CF}$=251); 145.2 (arom., dm, $^1J_{CF}$=245); 169.7 (CO, s); 171.0 (CO, s).

HRMS (ESI) m/z: [(M+H)$^+$] ($C_{21}H_{28}F_5N_4O_6$) calculated: 527.1924, found: 527.1924.

Elem. analysis: M·1.8TFA·1.6H$_2$O, calculated: C (38.9), H (4.2), N (7.4), F (26.0), found: C (39.2), H (3.9), N (7.0), F (26.0).

Example 40: Preparation of 2,2',2"-(10-(2-fluorobenzyl)-1,4,7,10-tetraazacyclododecane-1,4,7-triyl)triacetic acid (40)

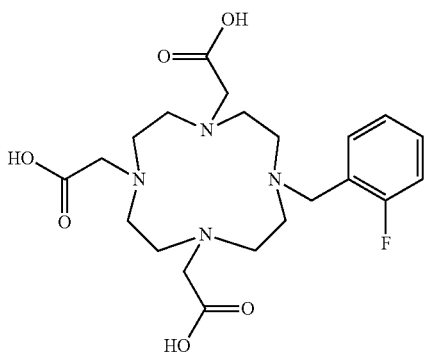 [SMILES: O=C(O)CN1CCN(CC(=O)O)CCN(Cc2ccccc2F)CCN(CC(=O)O)CC1]

According to procedure in Example 1, reaction of starting compound B (200 mg, 0.336 mmol), 1-(bromomethyl)-2-fluorobenzene (71 mg, 0.373 mmol) and anhydrous potassium carbonate (185 mg, 1.34 mmol) in acetonitrile (20 mL) gave analogously 173 mg of the product as a white fluffy solid (0.253 mmol, 75% yield relative to B).

$^1$H NMR (D$_2$O with internal dioxane reference, 95° C., 500 MHz): $\delta_H$ 3.09-3.22 (cycle, m, 4H); 3.22-3.32 (cycle, m, 4H); 3.32-3.43 (cycle, m, 4H); 3.43-3.61 (cycle, CH$_2$—COOH, m, 8H); 4.03 (CH$_2$—COOH, s, 2H); 4.54 (CH$_2$-arom., s, 2H); 7.23-7.42 (arom., m, 2H); 7.51-7.56 (arom., m, 2H); $^{13}$C{$^1$H} NMR (D$_2$O with internal dioxane reference, 95° C., 125 MHz): $\delta_C$ 49.2 (cycle, s); 49.5 (cycle, s); 50.7 (cycle, s); 52.0 (cycle, s); 52.2 (CH$_2$-arom., d, $^3J_{CF}$=3 Hz); 54.1 (CH$_2$—COOH, s); 55.9 (CH$_2$—COOH, s); 116.9 (arom., d, $^2J_{CF}$=22 Hz); 117.2 (arom., d, $^2J_{CF}$=14 Hz); 126.3 (arom., d, $^3J_{CF}$=4 Hz); 133.6 (arom., d, $^4J_{CF}$=3 Hz); 133.7 (arom., d, $^3J_{CF}$=9 Hz); 162.1 (arom., d, $^1J_{CF}$=247 Hz); 169.8 (CO, s); 173.4 (CO, s); $^{19}$F{$^1$H} NMR (D$_2$O with external hexafluorobenzene reference, 95° C., 470 MHz): −122.0 (s).

HRMS (ESI) m/z: [(M+H)$^+$] ($C_{21}H_{32}FN_4O_6$) calculated: 455.2300, found: 455.2301.

Elem. analysis: M·2TFA, calculated: C (44.0), H (4.9), N (8.2), F (19.5), found: C (43.5), H (5.0), N (8.0), F (19.3).

Example 41: Preparation of 2,2',2"-(10-(2,6-difluorobenzyl)-1,4,7,10-tetraazacyclododecane-1,4,7-triyl)triacetic acid (41)

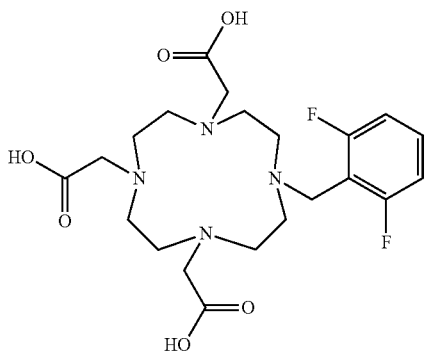 [SMILES: O=C(O)CN1CCN(CC(=O)O)CCN(Cc2c(F)cccc2F)CCN(CC(=O)O)CC1]

According to procedure in Example 1, reaction of starting compound B (200 mg, 0.336 mmol), 2-(bromomethyl)-1,3-difluorobenzene (77 mg, 0.372 mmol) and anhydrous potassium carbonate (185 mg, 1.34 mmol) in acetonitrile (20 mL) gave analogously 171 mg of the product as a white fluffy solid (0.244 mmol, 73% yield relative to B).

$^1$H NMR (D$_2$O with internal dioxane reference, 95° C., 500 MHz): $\delta_H$ 3.20-3.25 (cycle, m, 4H); 3.29-3.34 (cycle, m, 4H); 3.34-3.39 (cycle, m, 4H); 3.42-3.48 (cycle, m, 4H); 3.62 (CH$_2$—COOH, s, 4H); 3.98 (CH$_2$—COOH, s, 2H); 4.57 (CH$_2$-arom., s, 2H); 7.21 (arom., dm, 2H, $^3J_{HH}$=9 Hz); 7.63 (arom., tt, 1H, $^3J_{HH}$=9 Hz, $^4J_{HF}$=7 Hz); $^{13}$C{$^1$H} NMR (D$_2$O with internal dioxane reference, 95° C., 125 MHz): 46.3 (CH$_2$-arom., t, $^3J_{CF}$=3 Hz); 49.6 (cycle, s); 49.9 (cycle, s); 50.6 (cycle, s); 51.9 (cycle, s); 54.5 (CH$_2$—COOH, s); 55.9 (CH$_2$—COOH, s); 106.3 (arom., t, $^2J_{CF}$=19 Hz); 113.0 (arom., dm, $^2J_{CF}$=26 Hz); 134.3 (arom., t, $^3J_{CF}$=11 Hz); 162.3 (arom., dd, $^1J_{CF}$=249 Hz, $^3J_{CF}$=7 Hz); 170.1 (CO, s); 173.3 (CO, s); $^{19}$F{$^1$H} NMR (D$_2$O with external hexafluorobenzene reference, 95° C., 470 MHz): −108.1 (s).

HRMS (ESI) m/z: [(M+H)$^+$] ($C_{21}H_{31}F_2N_4O_6$) calculated: 473.2206, found: 473.2208.

Elem. analysis: M·2TFA, calculated: C (42.9), H (4.6), N (8.0), F (21.7), found: C (42.9), H (4.8), N (7.9), F (21.6).

Example 42: Preparation of 2,2',2"-(10-(naphthalen-2-ylmethyl)-1,4,7,10-tetraazacyclododecane-1,4,7-triyl)triacetic acid (42)

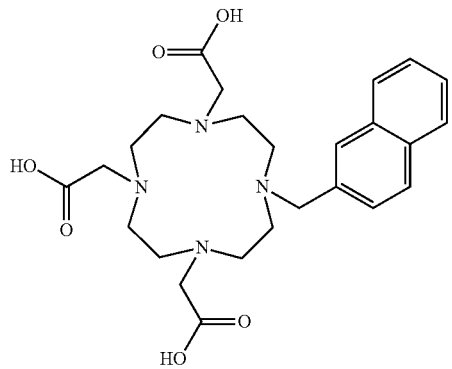 [SMILES: O=C(O)CN1CCN(CC(=O)O)CCN(Cc2ccc3ccccc3c2)CCN(CC(=O)O)CC1]

According to procedure in Example 1, reaction of starting compound B (400 mg, 0.671 mmol), 2-(bromomethyl)naphthalene (164 mg, 0.742 mmol) and anhydrous potassium carbonate (371 mg, 2.69 mmol) in acetonitrile (20 mL) gave analogously 298 mg of the product as a white fluffy solid (0.421 mmol, 63% yield relative to B).

HRMS (ESI) m/z: [(M−H)$^-$] ($C_{25}H_{33}N_4O_6$) calculated: 485.2406, found: 485.2403.

Elem. analysis: M·1.6TFA·2.2H$_2$O, calculated: C (47.8), H (5.7), N (7.9), F (12.9), found: C (47.6), H (5.1), N (7.7), F (12.8).

Example 43: Preparation of 2,2',2''-(10-(furan-2-ylmethyl)-1,4,7,10-tetraazacyclododecane-1,4,7-triyl)triacetic acid (43)

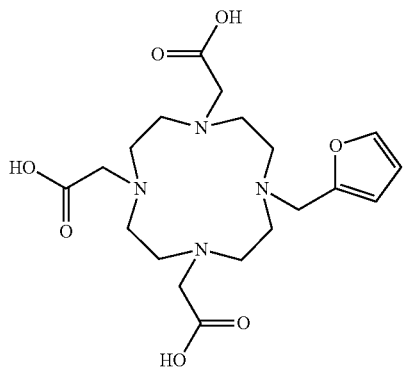 [SMILES: O=C(O)CN1CCN(CC(=O)O)CCN(Cc2ccco2)CCN(CC(=O)O)CC1]

According to procedure in Example 1, reaction of starting compound B (250 mg, 0.420 mmol), 2-(chloromethyl)furan (238 mg, 2.04 mmol) and anhydrous potassium carbonate (255 mg, 1.85 mmol) in acetonitrile (20 mL) shortened to 90 minutes at room temperature gave analogously 88 mg of the product as a white fluffy solid (0.134 mmol, 32% yield relative to B).

HRMS (ESI) m/z: [(M+H)$^+$] ($C_{19}H_{31}N_4O_7$) calculated: 427.2187, found: 427.2187.

Elem. analysis: M·2.0TFA·0.2H$_2$O, calculated: C (42.0), H (5.0), N (8.5), F (17.3), found: C (41.9), H (5.1), N (8.4), F (17.5).

Example 44: Preparation of 2,2',2''-(10-(2-oxo-2-phenylethyl)-1,4,7,10-tetraazacyclododecane-1,4,7-triyl)triacetic acid (44)

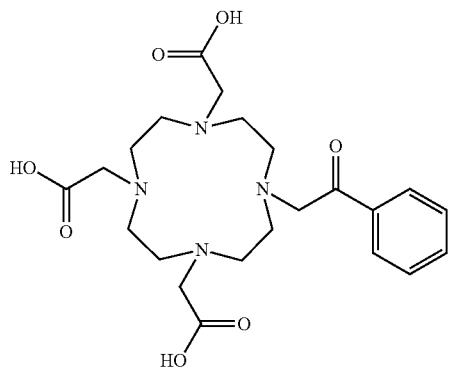 [SMILES: O=C(O)CN1CCN(CC(=O)O)CCN(CC(=O)c2ccccc2)CCN(CC(=O)O)CC1]

According to procedure in Example 1, reaction of starting compound B (200 mg, 0.336 mmol), phenacyl bromide (74 mg, 0.369 mmol) and anhydrous potassium carbonate (185 mg, 1.34 mmol) in acetonitrile (20 mL) gave analogously 104 mg of the product as a white fluffy solid (0.146 mmol, 43% yield relative to B).

HRMS (ESI) m/z: [(M+Na)$^+$] ($C_{22}H_{32}N_4NaO_7$) calculated: 487.2164, found: 487.2163.

Elem. analysis: M·2.0TFA·1.0H$_2$O, calculated: C (44.0), H (5.1), N (7.9), found: C (43.7), H (4.9), N (7.8).

Example 45: Preparation of 2,2'-(4-(2-hydroxy-5-nitrobenzyl)-1,4,7,10-tetraazacyclododecane-1,7-diyl)diacetic acid (45)

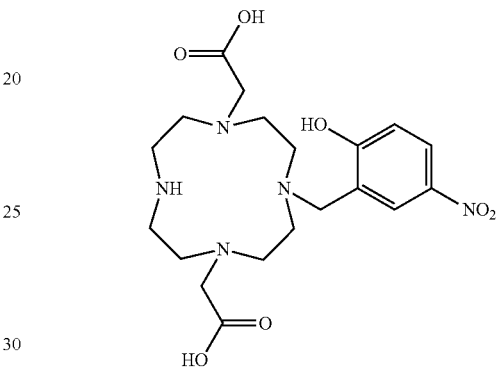

Starting compound A (400 mg, 1.00 mmol) and anhydrous potassium carbonate (414 mg, 3.00 mmol) were placed into a 50 mL flask under argon atmosphere and anhydrous acetonitrile (20 mL) was added. 2-(bromomethyl)-4-nitrophenol (232 mg, 1.00 mmol) was dissolved in anhydrous acetonitrile (5 mL) and during 5 minutes dropwise added to the mixture while stirring. The reaction mixture was stirred under argon for 24 hours at room temperature. The solids were filtered off and the filtrate was concentrated on rotary evaporator. Resulting oil was purified on preparative HPLC (C18 column, acetonitrile/water gradient with 0.1% trifluoroacetic acid in the mobile phase). At this point, the doubly alkylated byproduct was also collected and processed separately. Fractions containing pure product in the form of tert.butyl ester were pooled, evaporated and dried in high vacuum. The residue was dissolved in neat trifluoroacetic acid (4 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 460 mg of the product as a white fluffy solid (0.643 mmol, 64% yield relative to A).

$^1$H NMR (D$_2$O with internal dioxane reference, 25° C., 500 MHz): δ$_H$ 2.94-3.09 (cycle, m, 4H); 3.09-3.22 (cycle, m, 4H); 3.24 (CH$_2$—COOH, d, 2H, $^2J_{HH}$=18 Hz); 3.28-3.39 (cycle, m, 4H); 3.41 (CH$_2$—COOH, d, 2H, $^2J_{HH}$=18 Hz); 3.42-3.56 (cycle, m, 4H); 4.61 (CH$_2$-arom., s, 2H); 7.09 (arom., d, 1H, $^3J_{HH}$=9 Hz); 8.30 (arom., dd, 1H, $^3J_{HH}$=9 Hz, $^4J_{HH}$=3 Hz); 8.41 (arom., d, 1H, $^4J_{HH}$=3 Hz). $^{13}$C{$^1$H} NMR (D$_2$O with internal dioxane reference, 25° C., 125 MHz): δ$_C$ 42.2 (cycle, s); 47.9 (cycle, s); 48.3 (cycle, s); 50.8 (cycle, s); 52.9 (CH$_2$—COOH, s); 53.7 (CH$_2$-arom., s); 116.0

(arom., s); 116.3 (arom., s); 128.5 (arom., s); 129.2 (arom., s); 140.5 (arom., s); 161.5 (arom., s); 173.9 (CO, s).

HRMS (ESI) m/z: [(M+H)$^+$] ($C_{19}H_{30}N_5O_7$) calculated: 440.2140, found: 440.2142.

Elem. analysis: M·2.1TFA·2.0H$_2$O, calculated: C (39.0), H (4.9), N (9.8), F (16.7), found: C (38.6), H (4.5), N (9.6), F (16.3).

Example 46: Preparation of 2,2'-(4,10-bis(2-hydroxy-5-nitrobenzyl)-1,4,7,10-tetraazacyclododecane-1,7-diyl)diacetic acid (46)

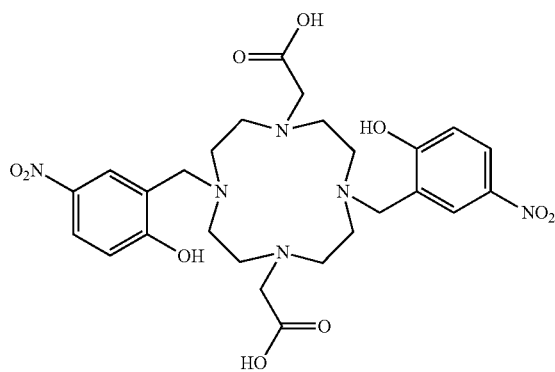 [SMILES: O=C(O)CN1CCN(Cc2cc([N+](=O)[O-])ccc2O)CCN(CC(=O)O)CCN(Cc2cc([N+](=O)[O-])ccc2O)CC1]

The compound was synthesized according to the procedure in Example 45 as the doubly alkylated byproduct, giving analogously 74 mg of the product as a pale yellow fluffy solid (0.084 mmol, 8% yield relative to A).

HRMS (ESI) m/z: [(M−H)$^−$] ($C_{26}H_{33}N_6O_{10}$) calculated: 589.2264, found: 589.2266.

Elem. analysis: M·2.1TFA·2.6H$_2$O, calculated: C (41.4), H (4.7), N (9.6), F (13.6), found: C (41.8), H (4.8), N (9.0), F (13.4).

Example 47: Preparation of 2,2'-(4-((6-carboxypyridin-2-yl)methyl)-1,4,7,10-tetraazacyclododecane-1,7-diyl)diacetic acid (47)

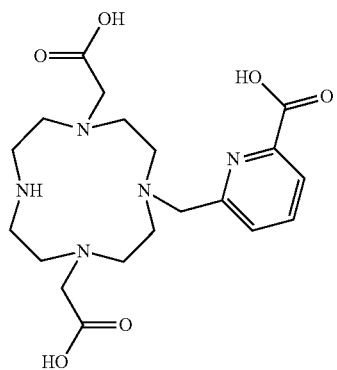 [SMILES: O=C(O)CN1CCNCCN(CC(=O)O)CCN(Cc2cccc(C(=O)O)n2)CC1]

Starting compound A (400 mg, 1.00 mmol) and anhydrous potassium carbonate (414 mg, 3.00 mmol) were placed into a 50 mL flask under argon atmosphere and anhydrous acetonitrile (20 mL) was added. Methyl 6-(chloromethyl)picolinate hydrochloride (111 mg, 0.50 mmol) was dissolved in anhydrous acetonitrile (5 mL) and during 5 minutes dropwise added to the mixture while stirring. The reaction mixture was stirred under argon for 24 hours at room temperature. The solids were filtered off and the filtrate was concentrated on rotary evaporator. Resulting oil was purified on preparative HPLC (C18 column, acetonitrile/water gradient with 0.1% trifluoroacetic acid in the mobile phase). At this point, the doubly alkylated byproduct was also collected and processed separately. Fractions containing pure product in the form of tert.butyl ester were pooled, evaporated and dried in high vacuum. The residue was dissolved in a mixture of acetonitrile (3 mL) and distilled water (3 mL). Hydrolysis of the methylester function followed by addition of LiOH·H$_2$O (92 mg, 2.2 mmol) and stirring at room temperature. After 45 minutes the reaction was complete (followed by LC-MS). The reaction mixture was acidified with trifluoroacetic acid (0.190 mL, 2.48 mmol) and evaporated on rotary evaporator. The residue was purified on preparative HPLC (C18 column, acetonitrile/water gradient with 0.1% trifluoroacetic acid in the mobile phase). Fractions containing pure intermediate with free carboxylate on pyridine were pooled, evaporated and dried in high vacuum. The residue was dissolved in neat trifluoroacetic acid (4 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 229 mg of the product as a white fluffy solid (0.310 mmol, 62% yield relative to methyl 6-(chloromethyl)picolinate hydrochloride).

HRMS (ESI) m/z: [(M+H)$^+$] ($C_{19}H_{30}N_5O_6$) calculated: 424.2191, found: 424.2191.

Elem. analysis: M·2.4TFA·2.4H$_2$O, calculated: C (38.6), H (4.9), N (9.5), F (18.5), found: C (38.8), H (4.8), N (9.4), F (18.3).

Example 48: The preparation of 6,6'-((4,10-bis(carboxymethyl)-1,4,7,10-tetraazacyclododecane-1,7-diyl)bis(methylene))dipicolinic acid (48)

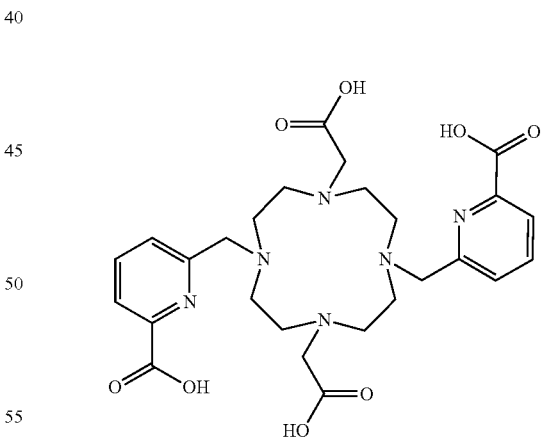

The compound was synthesized according to the procedure in Example 47 as the doubly alkylated byproduct, giving analogously 61 mg of the product as a white fluffy solid (0.075 mmol, 30% yield relative to methyl 6-(chloromethyl)picolinate hydrochloride).

$^1$H NMR (D$_2$O with internal dioxane reference, 95° C., 500 MHz): $\delta_H$ 3.25-3.37 (cycle, m, 8H); 3.42 (CH$_2$—COOH, s, 4H); 3.55-3.67 (cycle, m, 8H); 4.71 (CH$_2$-arom., s, 4H); 7.92 (arom., dd, 1H, $^3J_{HH}$=8 Hz, $^4J_{HH}$=1 Hz); 8.15 (arom., t, 1H, $^3J_{HH}$=8 Hz); 8.31 (arom., dd, 1H, $^3J_{HH}$=8 Hz, $^4J_{HH}$=1 Hz); $^{13}C\{^1H\}$ NMR (D$_2$O with internal dioxane reference, 95° C., 125 MHz): δ$_C$ 49.4 (cycle, s); 52.1 (cycle, s); 54.1 (CH$_2$—COOH, s); 58.8 (CH$_2$-arom., s); 126.7 (arom., s); 130.0 (arom., s); 141.2 (arom., s); 148.3 (arom., s); 150.3 (arom., s); 167.5 (CO, s); 173.8 (CO, s).

HRMS (ESI) m/z: [(M+H)$^+$] (C$_{26}$H$_{35}$N$_6$O$_8$) calculated: 559.2511, found: 559.2514.

Elem. analysis: M·2.1TFA·0.9H$_2$O, calculated: C (44.6), H (4.7), N (10.3), F (14.7), found: C (45.0), H (4.7), N (10.3), F (14.2).

Example 49: Preparation of 2,2'-(4-((6-methylpyridin-2-yl)methyl)-1,4,7,10-tetraazacyclododecane-1,7-diyl)diacetic acid (49)

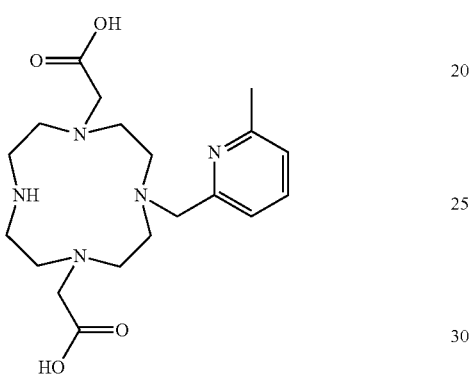

According to procedure in Example 45, reaction of starting compound A (400 mg, 1.00 mmol), anhydrous potassium carbonate (500 mg, 3.62 mmol) and 2-(chloromethyl)-6-methylpyridine hydrochloride (178 mg, 1.00 mmol) gave analogously 339 mg of the product as a white fluffy solid (0.461 mmol, 46% yield relative to A).

HRMS (ESI) m/z: [(M+H)$^+$] (C$_{19}$H$_{32}$N$_5$O$_4$) calculated: 394.2449, found: 394.2450.

Elem. analysis: M·3TFA, calculated: C (40.8), H (4.7), N (9.5), F (23.2), found: C (41.1), H (4.9), N (9.3), F (23.7).

Example 50: Preparation of 2,2'-(4,10-bis((6-methylpyridin-2-yl)methyl)-1,4,7,10-tetraazacyclododecane-1,7-diyl)diacetic acid (50)

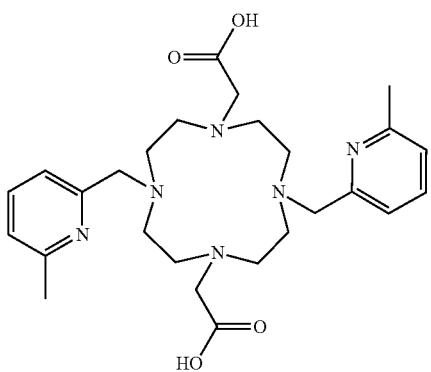 [SMILES: Cc1cccc(CN2CCN(CC(=O)O)CCN(Cc3cccc(C)n3)CCN(CC(=O)O)CC2)n1]

The compound was synthesized according to the procedure in Example 49 as the doubly alkylated byproduct, giving analogously 92 mg of the product as a white fluffy solid (0.091 mmol, 9% yield relative to A).

$^1$H NMR (D$_2$O with internal dioxane reference, 95° C., 500 MHz): δ$_H$ 2.97 (CH$_3$, s, 6H); 3.00-3.18 (cycle, m, 8H); 3.53 (CH$_2$—COOH, s, 4H); 3.54-3.66 (cycle, m, 8H); 4.04 (CH$_2$-arom., s, 4H); 7.92 (arom., d, 2H, $^3J_{HH}$=8 Hz); 8.04 (arom., d, 2H, $^3J_{HH}$=8 Hz); 8.48 (arom., t, 2H, $^3J_{HH}$=8 Hz). $^{13}C\{^1H\}$ NMR (D$_2$O with internal dioxane reference, 95° C., 125 MHz): δ$_C$ 20.4 (CH$_3$, s); 48.2 (cycle, s); 52.1 (cycle, s); 55.1 (CH$_2$—COOH, s); 56.6 (CH$_2$-arom., s); 127.1 (arom., s); 128.7 (arom., s); 147.6 (arom., s); 149.4 (arom., s); 157.0 (arom., s); 168.5 (CO, s).

HRMS (ESI) m/z: [(M+H)$^+$] (C$_{26}$H$_{39}$N$_6$O$_4$) calculated: 499.3027, found: 499.3028.

Elem. analysis: M·4.2TFA·1.9H$_2$O, calculated: C (40.8), H (4.6), N (8.3), F (23.7), found: C (40.4), H (4.1), N (8.0), F (23.4).

Example 51: Preparation of 2-((4,10-bis(carboxymethyl)-1,4,7,10-tetraazacyclododecan-1-yl)methyl)pyridine 1-oxide (51)

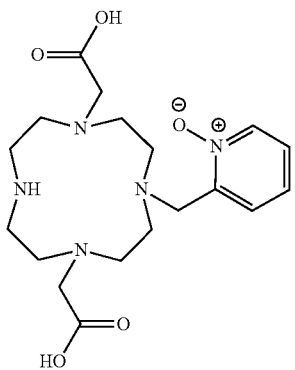 [SMILES: O=C(O)CN1CCNCCN(CC(=O)O)CCN(Cc2cccc[n+]2[O-])CC1]

According to procedure in Example 45, reaction of starting compound A (800 mg, 2.00 mmol), anhydrous potassium carbonate (828 mg, 6.00 mmol) and 2-(chloromethyl)pyridine 1-oxide (143 mg, 1.00 mmol) gave analogously 312 mg of the product as a white fluffy solid (407 mmol, 41% yield relative to 2-(chloromethyl)pyridine 1-oxide).

HRMS (ESI) m/z: [(M+H)$^+$] (C$_{18}$H$_{30}$N$_5$O$_5$) calculated: 396.2242, found: 396.2242.

Elem. analysis: M·2.9TFA·2.2H$_2$O, calculated: C (37.3), H (4.8), N (9.1), F (21.6), found: C (37.7), H (4.5), N (8.7), F (21.2).

Example 52: Preparation of 2,2'-((4,10-bis(carboxymethyl)-1,4,7,10-tetraazacyclododecane-1,7-diyl)bis(methylene))bis(pyridine 1-oxide) (52)

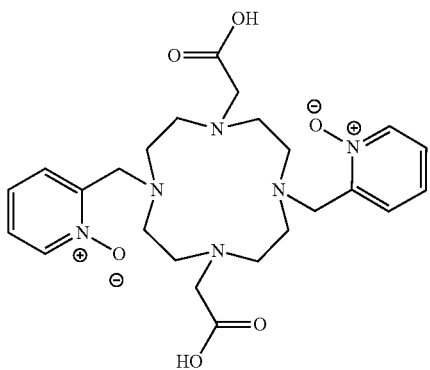 [SMILES: O=C(O)CN1CCN(Cc2cccc[n+]2[O-])CCN(CC(=O)O)CCN(Cc2cccc[n+]2[O-])CC1]

According to procedure in Example 45, reaction of starting compound A (80 mg, 0.200 mmol), anhydrous potassium carbonate (110 mg, 0.800 mmol) and 2-(chloromethyl)pyridine 1-oxide (63 mg, 0.440 mmol) gave analogously 107 mg of the product as a white fluffy solid (0.134 mmol, 67% yield relative to A).

$^1$H NMR (D$_2$O with internal dioxane reference, 95° C., 500 MHz): $\delta_H$ 3.28-3.34 (cycle, m, 8H); 3.41 (CH$_2$—COOH, s, 4H); 3.42-3.48 (cycle, m, 8H); 4.74 (CH$_2$-arom., s, 4H); 7.76 (arom., ddd, 2H, $^3J_{HH}$=8 Hz, $^3J_{HH}$=6 Hz, $^4J_{HH}$=2 Hz); 7.81 (arom., td, 2H, $^3J_{HH}$=8 Hz, $^3J_{HH}$=6 Hz); 7.86-7.92 (arom., m, 2H); 8.49-8.56 (arom., m, 2H). $^{13}$C{$^1$H} NMR (D$_2$O with internal dioxane reference, 95° C., 125 MHz): $\delta_C$ 49.7 (cycle, s); 52.5 (cycle, s); 54.0 (CH$_2$—COOH, s); 55.0 (CH$_2$-arom., s); 129.4 (arom., s); 130.8 (arom., s); 131.8 (arom., s); 140.9 (arom., s); 141.0 (arom., s); 173.2 (CO, s).

HRMS (ESI) m/z: [(M+H)$^+$] (C$_{24}$H$_{35}$N$_6$O$_6$) calculated: 503.2613, found: 503.2611.

Elem. analysis: M·2.4TFA·1.4H$_2$O, calculated: C (43.2), H (4.9), N (10.5), F (17.1), found: C (43.7), H (5.1), N (9.9), F (16.9).

Example 53: Preparation of 2,2'-(4-((5-carboxyfuran-2-yl)methyl)-1,4,7,10-tetraazacyclododecane-1,7-diyl)diacetic acid (53) on According to procedure in Example 47, reaction of starting compound A (200 mg, 0.500 mmol), anhydrous potassium carbonate (212 mg, 1.53 mmol) and methyl 5-(chloromethyl)furan-2-carboxylate (87 mg, 0.500 mmol) followed by methyl ester hydrolysis with LiOH·H$_2$O (44 mg, 1.05 mmol) and further processed as in Example 47 gave analogously 66 mg of the product as a white fluffy solid (0.099 mmol, 20% yield relative to A).

HRMS (ESI) m/z: [(M+H)$^+$] (C$_{18}$H$_{29}$N$_4$O$_7$) calculated: 413.2031, found: 413.2036.

Elem. analysis: M·2.0TFA·1.5H$_2$O, calculated: C (39.6), H (5.0), N (8.4), F (17.1), found: C (39.4), H (4.6), N (8.0), F (17.0).

Example 54: Preparation of 5,5'-((4,10-bis(carboxymethyl)-1,4,7,10-tetraazacyclododecane-1,7-diyl)bis(methylene))bis(furan-2-carboxylic acid) (54)

The compound was synthesized according to the procedure in Example 53 as the doubly alkylated byproduct, giving analogously 87 mg of the product as a white fluffy solid (0.115 mmol, 23% yield relative to A).

HRMS (ESI) m/z: [(M+H)$^+$] (C$_{24}$H$_{33}$N$_4$O$_{10}$) calculated: 537.2191, found: 537.2192.

Elem. analysis: M·1.8TFA·0.9H$_2$O, calculated: C (43.7), H (4.7), N (7.4), F (13.5), found: C (43.9), H (4.7), N (7.2), F (13.5).

Example 55

Preparation of di-tert-butyl 2,2'-(4-benzyl-1,4,7,10-tetraazacyclododecane-1,7-diyl)diacetate (55a)

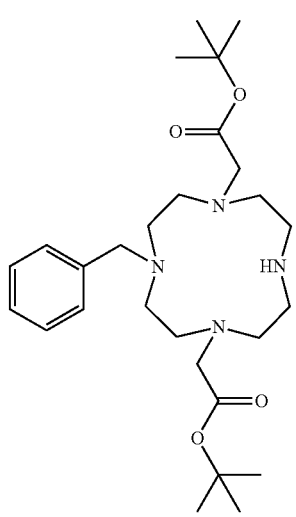 [SMILES: CC(C)(C)OC(=O)CN1CCNCCN(CC(=O)OC(C)(C)C)CCN(Cc2ccccc2)CC1]

Starting compound A (800 mg, 2.00 mmol) was placed into a 50 mL flask under argon atmosphere and anhydrous acetonitrile (20 mL) was added. Benzyl bromide (341 mg, 2.00 mmol) was dissolved in anhydrous acetonitrile (5 mL) and during 5 minutes dropwise added to the mixture while stirring. The reaction mixture was stirred under argon for 24 hours at room temperature. The solvent was evaporated on rotary evaporator. Resulting oil was purified on preparative HPLC (C18 column, acetonitrile/water gradient with 0.1% trifluoroacetic acid in the mobile phase). At this point, the doubly alkylated byproduct was also collected and processed separately. Fractions containing pure product were pooled, evaporated and dried in high vacuum to give 602 mg of the product as a pale yellow thick oil (0.691 mmol, 35% yield relative to A).

$^1$H NMR (CDCl$_3$, 25° C., 500 MHz): $\delta_H$ 1.45 (CH$_3$, s, 18H); 2.57-3.84 (cycle and CH$_2$—CO, m, 20H); 4.52 (CH$_2$-arom., s, 2H); 7.36-7.69 (arom., m, 5H); $^{13}$C{$^1$H} NMR (CDCl$_3$, 25° C., 125 MHz): 28.0 (CH$_3$, s); 42.5 (cycle, s); 48.0 (cycle, s); 49.8 (cycle, s); 50.9 (cycle, s); 54.4 (CH$_2$—COOH, s); 58.8 (CH$_2$-arom., s); 83.2 (C—CH$_3$, s); 128.4 (arom., s); 129.8 (arom., s); 130.8 (arom., s); 131.1 (arom., s); 170.5 (CO, s).

HRMS (ESI) m/z: [(M+H)$^+$] (C$_{27}$H$_{47}$N$_4$O$_4$) calculated: 491.3592, found: 491.3590.

Elem. analysis: M·2.8TFA·3.4H$_2$O, calculated: C (44.9), H (6.4), N (6.4), F (18.3), found: C (44.9), H (6.0), N (6.4), F (17.9).

Example 56: Preparation of 2,2'-(4,10-dibenzyl-1,4,7,10-tetraazacyclododecane-1,7-diyl)diacetic acid (56)

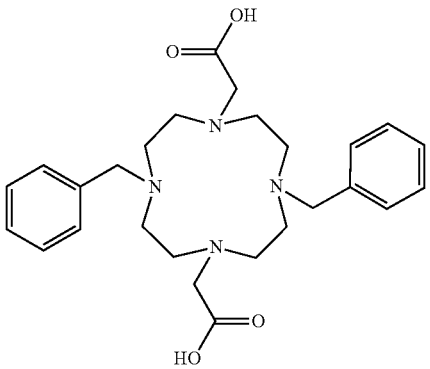 [SMILES: O=C(O)CN1CCN(Cc2ccccc2)CCN(CC(=O)O)CCN(Cc2ccccc2)CC1]

The compound was prepared according to procedure in Example 45 with a minor modification that no potassium carbonate was used. Reaction of starting compound A (800 mg, 2.00 mmol), and benzyl bromide (341 mg, 2.00 mmol) gave analogously 122 mg of the product as a white fluffy solid (166 mmol, 8% yield relative to A).

HRMS (ESI) m/z: [(M−H)$^-$] (C$_{26}$H$_{35}$N$_4$O$_4$) calculated: 467.2664, found: 467.2653.

Elem. analysis: M·2.0TFA·2.2H$_2$O, calculated: C (48.9), H (5.8), N (7.6), F (15.5), found: C (49.2), H (5.6), N (7.3), F (15.5).

Example 57: Preparation of 2,2'-(4-((perfluorophenyl)methyl)-1,4,7,10-tetraazacyclododecane-1,7-diyl)diacetic acid (57)

Compound was prepared according to procedure in Example 45 with a minor modification that no potassium carbonate was used. Reaction of starting compound A (400 mg, 1.00 mmol) and 1-(bromomethyl)-2,3,4,5,6-pentafluorobenzene (261 mg, 1.00 mmol) gave analogously 451 mg of the product as a white fluffy solid (0.576 mmol, 58% yield relative to A).

$^1$H NMR (D$_2$O with internal dioxane reference, 95° C., 500 MHz): $\delta_H$ 2.99-3.10 (cycle, m, 4H); 3.18-3.31 (cycle, m, 8H); 3.36-3.47 (cycle, m, 4H); 3.54 (CH$_2$—COOH, s, 4H); 4.72 (CH$_2$-arom., t, 2H, $^4J_{HF}$=2 Hz). $^{13}$C{$^1$H} NMR (D$_2$O with internal dioxane reference, 95° C., 125 MHz): 43.8 (cycle, s); 46.3 (CH$_2$-arom., s); 49.9 (cycle, s); 50.8 (cycle, s); 52.1 (cycle, s); 55.2 ($CH_2$—COOH, s); 103.6 (arom., tm, $^2J_{CF}$=17 Hz); 138.6 (arom., dm, $^1J_{CF}$=252 Hz); 143.9 (arom., dm, $^1J_{CF}$=258 Hz); 147.0 (arom., dm, $^1J_{CF}$=248 Hz); 175.3 (CO, s). $^{19}F\{^1H\}$ NMR ($D_2O$ with external $C_6F_6$ reference, 95° C., 470 MHz): −156.3 (t, 2F, $^3J_{FF}$=21 Hz); −144.6 (t, 1F, $^3J_{FF}$=21 Hz); −134.0 (d, 2F, $^3J_{FF}$=21 Hz).

HRMS (ESI) m/z: [(M−H)$^−$] ($C_{19}H_{24}F_5N_4O_4$) calculated: 467.1723, found: 467.1716.

Elem. analysis: M·2.4TFA·2.3$H_2O$, calculated: C (36.5), H (4.1), N (7.2), F (29.6), found: C (37.1), H (3.8), N (6.5), F (29.1).

Example 58: Preparation of 2,2'-(4,10-bis((perfluorophenyl)methyl)-1,4,7,10-tetraazacyclododecane-1,7-diyl)diacetic acid (58) F

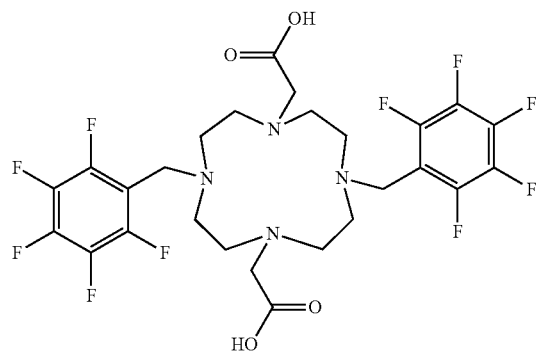 [SMILES: O=C(O)CN1CCN(Cc2c(F)c(F)c(F)c(F)c2F)CCN(CC(=O)O)CCN(Cc2c(F)c(F)c(F)c(F)c2F)CC1]

The compound was synthesized according to the procedure in Example 57 as the doubly alkylated byproduct, giving analogously 115 mg of the product as a white fluffy solid (0.136 mmol, 14% yield relative to A).

HRMS (ESI) m/z: [(M−H)$^−$] ($C_{26}H_{25}F_{10}N_4O_4$) calculated: 647.1722, Ho found: 647.1709.

Elem. analysis: M·1.5TFA·1.5$H_2O$, calculated: C (41.2), H (3.6), N (6.6), F (32.5), found: C (41.4), H (3.6), N (6.4), F (32.3).

Example 59: Preparation of 2,2'-(4-((1-methoxynaphthalen-2-yl)methyl)-1,4,7,10-tetraazacyclododecane-1,7-diyl)diacetic acid (59)

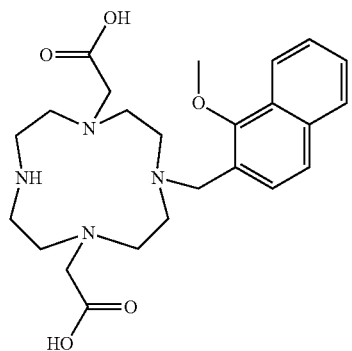 [SMILES: COc1c(CN2CCN(CC(=O)O)CCNCCN(CC(=O)O)CC2)ccc2ccccc12]

According to procedure in Example 45, reaction of starting compound A (775 mg, 1.94 mmol), anhydrous potassium carbonate (401 mg, 2.90 mmol) and 2-(chloromethyl)-1-methoxynaphthalene (200 mg, 0.968 mmol) gave analogously 325 mg of the product as a white fluffy solid (422 mmol, 44% yield relative to 2-(chloromethyl)-1-methoxynaphthalene).

$^1H$ NMR (DMSO, 100° C., 500 MHz): $\delta_H$ 2.92-3.03 (cycle, m, 4H); 3.03-3.12 (cycle, m, 4H); 3.12-3.24 (cycle, m, 8H); 3.37 ($CH_2$—COOH, s, 4H); 3.98 ($CH_3$, s, 3H); 4.53 ($CH_2$-arom., s, 2H); 7.59-7.66 (arom., m, 3H); 7.76 (arom., d, 1H, $^3J_{HH}$=8 Hz); 7.95-8.01 (arom., m, 1H); 8.10-8.15 (arom., m, 1H); $^{13}C\{^1H\}$NMR (DMSO, 100° C., 125 MHz): $\delta_C$ 43.1 (cycle, s); 49.7 (cycle, s); 49.2 (cycle, s); 51.2 (cycle, s); 51.5 ($CH_2$-arom., s); 53.9 ($CH_2$—COOH, s); 62.6 ($CH_3$, s); 118.9 (arom., s); 122.1 (arom., s); 124.2 (arom., s); 126.3 (arom., s); 126.9 (arom., s); 127.0 (arom., s); 127.9 (arom., s); 128.2 (arom., s); 135.2 (arom., s); 155.8 (arom., s); 172.4 (CO, s).

HRMS (ESI) m/z: [(M+H)$^+$] ($C_{24}H_{35}N_4O_5$) calculated: 459.2602, found: 459.2602.

Elem. analysis: M·2.3TFA·2.7$H_2O$, calculated: C (44.6), H (5.5), N (7.3), F (17.0), found: C (44.8), H (5.2), N (7.0), F (17.3).

Example 60: Preparation of 2,2'-(4-((3-methoxynaphthalen-2-yl)methyl)-1,4,7,10-tetraazacyclododecane-1,7-diyl)diacetic acid (60) on

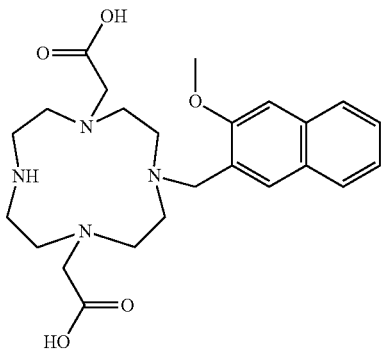 [SMILES: COc1cc2ccccc2cc1CN1CCN(CC(=O)O)CCNCCN(CC(=O)O)CC1]

According to procedure in Example 45, reaction of starting compound A (388 mg, 0.968 mmol), anhydrous potassium carbonate (200 mg, 1.45 mmol) and 2-(chloromethyl)-3-methoxynaphthalene (100 mg, 0.484 mmol) gave analogously 171 mg of the product as a white fluffy solid (236 mmol, 49% yield relative to 2-(chloromethyl)-3-methoxynaphthalene).

$^1H$ NMR (DMSO, 100° C., 500 MHz): $\delta_H$ 2.95-3.03 (cycle, m, 4H); 3.07-3.13 (cycle, m, 4H); 3.13-3.25 (cycle, m, 8H); 3.38 ($CH_2$—COOH, s, 4H); 3.98 ($CH_3$, s, 3H); 4.53 ($CH_2$-arom., s, 2H); 7.42 (arom., ddd, 1H, $^3J_{HH}$=8 Hz, $^3J_{HH}$=7 Hz, $^3J_{HH}$=1 Hz); 7.45 (arom., s, 1H); 7.53 (arom., ddd, 1H, $^3J_{HH}$=8 Hz, $^3J_{HH}$=7 Hz, $^3J_{HH}$=1 Hz); 7.83-7.92 (arom., m, 2H); 8.05 (arom., s, 1H); $^{13}C\{^1H\}$ NMR (DMSO, 100° C., 125 MHz): $\delta_C$ 43.1 (cycle, s); 48.7 (cycle, s); 49.2 (cycle, s); 51.3 (cycle, s); 52.0 ($CH_2$-arom., s); 53.9 ($CH_2$—COOH, s); 55.6 ($CH_3$, s); 106.5 (arom., s); 120.0 (arom., s); 124.0 (arom., s); 126.2 (arom., s); 127.0 (arom., s); 127.5 (arom., s); 127.7 (arom., s); 133.0 (arom., s); 134.6 (arom., s); 155.3 (arom., s); 172.2 (CO, s).

HRMS (ESI) m/z: [(M+H)$^+$] ($C_{24}H_{35}N_4O_5$) calculated: 459.2602, found: 459.2603.

Elem. analysis: M·2.0TFA·2.1$H_2O$, calculated: C (46.4), H (5.6), N (7.7), F (15.7), found: C (46.5), H (5.5), N (7.6), F (15.6).

Example 61: Preparation of 2,2'-(4-(2-carboxybenzyl)-1,4,7,10-tetraazacyclododecane-1,7-diyl)diacetic acid (61)

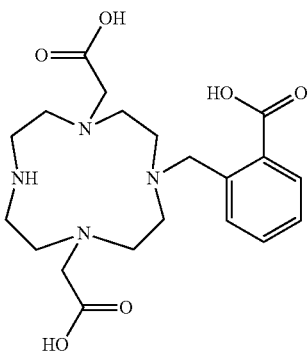 [SMILES: O=C(O)CN1CCNCCN(CC(=O)O)CCN(Cc2ccccc2C(=O)O)CC1]

Compound was synthesized according to procedure in Example 47 with minor modifications. Reaction of starting compound A (800 mg, 2.00 mmol), anhydrous potassium carbonate (552 mg, 4.00 mmol) and methyl 2-(bromomethyl)benzoate (275 mg, 1.20 mmol) was performed, followed by separation of the mono-alkylated intermediate by preparative HPLC as in Example 47. Hydrolysis of the methyl ester function followed in a mixture of acetonitrile (4 mL) and distilled water (3 mL) by addition of 2 M aqueous NaOH (2.1 mL, 4.2 mmol) and stirring for 16 h at room temperature. The intermediate with free benzoic acid moiety was isolated by preparative HPLC and subjected to treatment with trifluoroacetic acid and further processing analogously to Example 47, giving 303 mg of the product as a white fluffy solid (0.438 mmol, 37% yield relative to 2-(bromomethyl)benzoate).

HRMS (ESI) m/z: [(M–H)$^-$] ($C_{20}H_{29}N_4O_6$) calculated: 421.2093, found: 421.2082.

Elem. analysis: M·2.3TFA·0.4H$_2$O, calculated: C (42.7), H (4.8), N (8.1), F (18.9), found: C (42.7), H (5.3), N (7.7), F (19.4).

Example 62: Preparation of 2,2'-(4-(3-carboxybenzyl)-1,4,7,10-tetraazacyclododecane-1,7-diyl)diacetic acid (62)

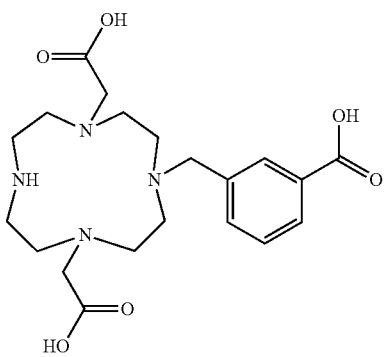 [SMILES: O=C(O)CN1CCNCCN(CC(=O)O)CCN(Cc2cccc(C(=O)O)c2)CC1]

According to procedure in Example 61, reaction of starting compound A (800 mg, 2.00 mmol), anhydrous potassium carbonate (552 mg, 4.00 mmol) and methyl 3-(bromomethyl)benzoate (275 mg, 1.20 mmol) gave analogously 343 mg of the product as a white fluffy solid (501 mmol, 42% yield relative to methyl 3-(bromomethyl)benzoate).

HRMS (ESI) m/z: [(M–H)$^-$] ($C_{20}H_{29}N_4O_6$) calculated: 421.2093, found: 421.2091. Elem. analysis: M·2.0TFA·1.9H$_2$O, calculated: C (42.1), H (5.3), N (8.2), F (16.6), found: C (42.5), H (5.5), N (7.8), F (16.5).

Example 63: Preparation of 2,2'-(4-(4-carboxybenzyl)-1,4,7,10-tetraazacyclododecane-1,7-diyl)diacetic acid (63

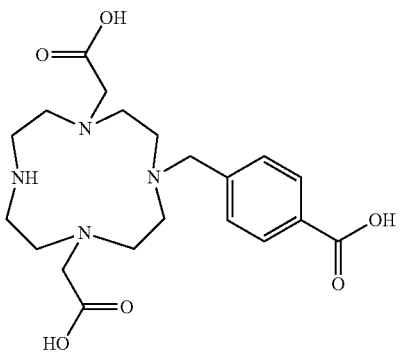 [SMILES: O=C(O)CN1CCNCCN(CC(=O)O)CCN(Cc2ccc(C(=O)O)cc2)CC1]

According to procedure in Example 61, reaction of starting compound A (800 mg, 2.00 mmol), anhydrous potassium carbonate (552 mg, 4.00 mmol) and methyl 4-(bromomethyl)benzoate (275 mg, 1.20 mmol) gave analogously 207 mg of the product as a white fluffy solid (283 mmol, 24% yield relative to methyl 4-(bromomethyl)benzoate).

$^1$H NMR (D$_2$O with internal dioxane reference, 95° C., 500 MHz): $\delta_H$ 2.89-3.43 (cycle and CH$_2$—COOH, m, 16H); 3.43-3.50 (cycle, m, 4H); 4.62 (CH$_2$-arom., s, 2H); 7.68 (arom., d, 2H, $^3J_{HH}$=8 Hz); 8.13 (arom., d, 2H, $^3J_{HH}$=8 Hz). $^{13}$C{$^1$H} NMR (D$_2$O with internal dioxane reference, 95° C., 125 MHz): $\delta_C$ 43.7 (cycle, s); 49.4 (cycle, s); 50.5 (cycle, s); 52.0 (cycle, s); 55.0 (CH$_2$—COOH, s); 58.5 (CH$_2$-arom., s); 131.4 (arom., s); 132.2 (arom., s); 132.7 (arom., s); 134.1 (arom., s); 169.8 (CO, s); 175.2 (CO, s).

HRMS (ESI) m/z: [(M–H)$^-$] ($C_{20}H_{29}N_4O_6$) calculated: 421.2093, found: 421.2090.

Elem. analysis: M·2.4TFA·1.9H$_2$O, calculated: C (40.8), H (5.0), N (7.7), F (18.7), found: C (41.1), H (5.3), N (7.3), F (18.4).

Example 64: Preparation of di-tert-butyl 2,2'-(4-(tert-butoxycarbonyl)-1,4,7,10-tetraazacyclododecane-1,7-diyl)diacetate (64a)

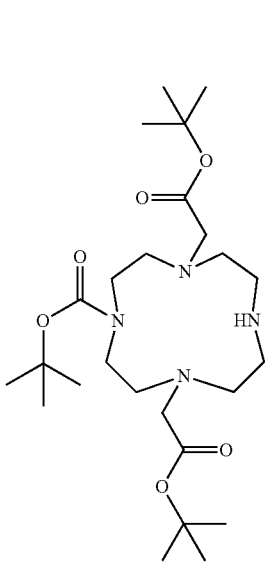 [SMILES: CC(C)(C)OC(=O)CN1CCNCCN(CC(=O)OC(C)(C)C)CCN(C(=O)OC(C)(C)C)CC1]

Starting compound A (2.00 g, 5.00 mmol) was placed into a 50 mL flask under argon atmosphere and anhydrous acetonitrile (20 mL) was added. Di-tert-butyl dicarbonate (563 mg, 2.58 mmol) was dissolved in anhydrous acetonitrile (1 mL) and added to the mixture. The reaction mixture was stirred under argon for 24 hours at room temperature. The solvent was evaporated on rotary evaporator and the residue was purified on preparative HPLC (C18 column, acetonitrile/water gradient with 0.1% trifluoroacetic acid in the mobile phase). Fractions containing the product were pooled, evaporated and dried in high vacuum to give 1.05 g of pale yellow thick oil (1.22 mmol, 47% yield relative to di-tert-butyl dicarbonate).

$^1$H NMR (CDCl$_3$, 25° C., 500 MHz): $\delta_H$ 1.45 (CH$_3$, S, 18H); 1.47 (CH$_3$, S, 9H); 2.80-3.33 (cycle, m, 16H); 3.42 (CH$_2$—COOH, s, 4H); $^{13}$C{$^1$H} NMR (CDCl$_3$, 25° C., 125 MHz): $\delta_C$ 28.0 (CH$_3$, s); 28.4 (CH$_3$, s); 45.0 (cycle, s); 51.4 (cycle, s); 53.3 (cycle, s); 53.4 (cycle, s); 55.3 (CH$_2$—COOH, s); 81.4 (C—CH$_3$, s); 82.5 (C—CH$_3$, s); 157.5 (CO, s); 170.1 (CO, s).

HRMS (ESI) m/z: [(M+H)$^{+}$] (C$_{25}$H$_{49}$N$_4$O$_6$) calculated: 501.3647, found: 501.3648.

Elem. analysis: M·3.0TFA·1.3H$_2$O, calculated: C (43.4), H (6.2), N (6.5), F (19.9), found: C (43.1), H (5.9), N (6.8), F (19.8).

Preparation of 2,2'-(4-(2-hydroxybenzyl)-1,4,7,10-tetraazacyclododecane-1,7-diyl)diacetic acid (64)

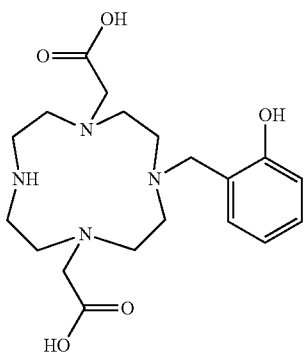 [SMILES: O=C(O)CN1CCNCCN(CC(=O)O)CCN(Cc2ccccc2O)CC1]

Starting compound 64a (225 mg, 0.262 mmol) and anhydrous potassium carbonate (256 mg, 1.85 mmol) were placed into a 50 mL flask under argon atmosphere and anhydrous acetonitrile (20 mL) was added. 2-(bromomethyl)phenyl acetate (85 mg, 0.370 mmol) was dissolved in anhydrous acetonitrile (1 mL) and added to the mixture. The reaction mixture was stirred under argon for 24 hours at room temperature. The solids were filtered off and distilled water (20 mL) was added to the filtrate. Removal of the acetate protective group followed by adding 2 M sodium hydroxide (0.5 mL, 1.00 mmol) and stirring at RT for 3 hours. After completion (followed by LC-MS), the reaction mixture was acidified with trifluoroacetic acid (0.200 mL, 2.59 mmol) and evaporated on rotary evaporator. The residue was purified on preparative HPLC (C18 column, acetonitrile/water gradient with 0.1% trifluoroacetic acid in the mobile phase). Fractions containing the intermediate with deprotected phenolic group were pooled, evaporated and dried in high vacuum. The residue was dissolved in neat trifluoroacetic acid (5 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 46 mg of the product as a white fluffy solid (0.073 mmol, 28% yield relative to 64a).

HRMS (ESI) m/z: [(M−H)$^{-}$] (C$_{19}$H$_{29}$N$_4$O$_5$) calculated: 393.2143, found: 393.2136.

Elem. analysis: M·1.7TFA·2.5H$_2$O, calculated: C (42.5), H (5.8), N (8.8), F (15.3), found: C (41.9), H (5.2), N (8.5), F (15.0).

Example 65: Preparation of 2,2'-(4-(2-hydroxy-3-methylbenzyl)-1,4,7,10-tetraazacyclododecane-1,7-diyl)diacetic acid (65)

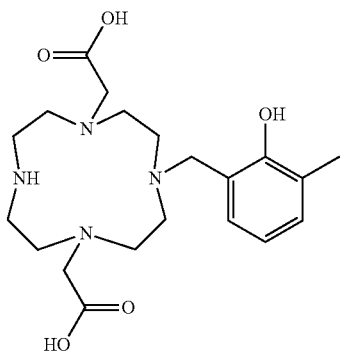 [SMILES: Cc1cccc(CN2CCN(CC(=O)O)CCNCCN(CC(=O)O)CC2)c1O]

According to procedure in Example 64, reaction of starting compound 64a (225 mg, 0.262 mmol), anhydrous potassium carbonate (256 mg, 1.85 mmol) and 2-(bromomethyl)-6-methylphenyl acetate (90 mg, 0.370 mmol) was performed. For hydrolysis of the acetate protective group 2 M sodium hydroxide (1.0 mL, 2.00 mmol) was used. Further processing was analogous to Example 64, giving 73 mg of the product as a white fluffy solid (112 mmol, 43% yield relative to 64a).

HRMS (ESI) m/z: [(M−H)⁻] ($C_{20}H_{31}N_4O_5$) calculated: 407.2300, found: 407.2292.

Elem. analysis: M·1.8TFA·2.1H$_2$O, calculated: C (43.5), H (5.9), N (8.6), F (15.7), found: C (43.2), H (5.4), N (8.3), F (15.3).

Example 66: Preparation of 2-((4,10-bis(carboxymethyl)-1,4,7,10-tetraazacyclododecan-1-yl)methyl)-6-methylpyridine 1-oxide (66)

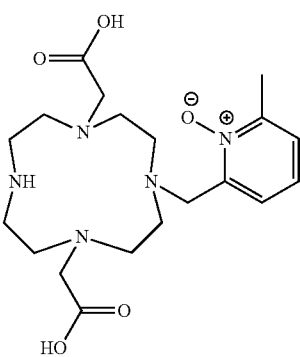 [SMILES: Cc1cccc(CN2CCN(CC(=O)O)CCNCCN(CC(=O)O)CC2)[n+]1[O-]]

Starting compound 64a (163 mg, 0.190 mmol) and anhydrous potassium carbonate (238 mg, 1.72 mmol) were placed into a 50 mL flask under argon atmosphere and anhydrous acetonitrile (20 mL) was added. 2-(chloromethyl)-6-methylpyridine 1-oxide (57 mg, 0.362 mmol) was dissolved in anhydrous acetonitrile (1 mL) and added to the mixture. The reaction mixture was stirred under argon for 24 hours at room temperature. The solids were filtered off and the filtrate was concentrated on rotary evaporator. Resulting oil was purified on preparative HPLC (C18 column, acetonitrile/water gradient with 0.1% trifluoroacetic acid in the mobile phase). Fractions containing pure product in the form of tert.butyl ester were pooled, evaporated and dried in high vacuum. The residue was dissolved in neat trifluoroacetic acid (4 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 98 mg of the product as a white fluffy solid (0.141 mmol, 74% yield relative to 64a).

HRMS (ESI) m/z: [(M+H)⁺] ($C_{19}H_{32}N_5O_5$) calculated: 410.2398, found: 410.2398.

Elem. analysis: M·2.1TFA·2.6H$_2$O, calculated: C (40.1), H (5.5), N (10.1), F (17.2), found: C (39.7), H (5.1), N (9.8), F (17.1).

Example 67: Preparation of 2,2'-(4-(3-carboxy-2-hydroxybenzyl)-1,4,7,10-tetraazacyclododecane-1,7-diyl)diacetic acid (67)

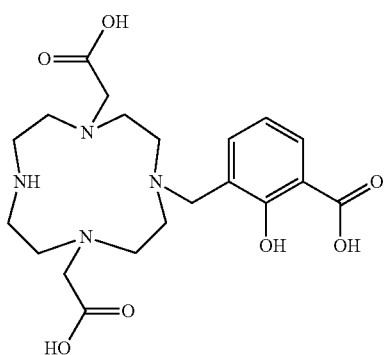 [SMILES: O=C(O)CN1CCNCCN(CC(=O)O)CCN(Cc2cccc(C(=O)O)c2O)CC1]

According to procedure in Example 64, reaction of starting compound 64a (200 mg, 0.233 mmol), anhydrous potassium carbonate (152 mg, 1.10 mmol) and methyl 2-acetoxy-3-(bromomethyl)benzoate (72 mg, 0.251 mmol) was performed. Simultaneous hydrolysis of the acetate and methyl ester protective groups followed in a mixture of methanol (3 mL) and distilled water (3 mL) with addition of LiOH·H$_2$O (28 mg, 0.667 mmol). The reaction was stirred for 24 h at room temperature. Then, the reaction was acidified with trifluoroacetic acid (0.065 mL, 0.850 mmol). Further processing was analogous to Example 64, giving 41 mg of the product as a white fluffy solid (0.070 mmol, 30% yield relative to 64a).

HRMS (ESI) m/z: [(M+H)⁺] ($C_{20}H_{31}N_4O_7$) calculated: 439.2187, found: 439.2188.

Elem. analysis: M·1.3TFA, calculated: C (46.3), H (5.4), N (9.6), F (12.6), found: C (46.8), H (5.5), N (9.8), F (13.3).

Example 68: Preparation of 2,2'-(4-((8-hydroxyquinolin-2-yl)methyl)-1,4,7,10-tetraazacyclododecane-1,7-diyl)diacetic acid (68)

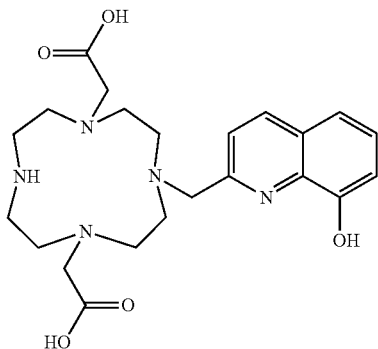 [SMILES: O=C(O)CN1CCNCCN(CC(=O)O)CCN(Cc2ccc3cccc(O)c3n2)CC1]

According to procedure in Example 64, reaction of starting compound 64a (200 mg, 0.233 mmol), anhydrous potassium carbonate (152 mg, 1.10 mmol) and 2-(bromomethyl)quinolin-8-yl acetate (92 mg, 0.329 mmol) was performed. Hydrolysis of the acetate protective group followed in a mixture of methanol (3 mL) and distilled water (3 mL) with addition of LiOH·H$_2$O (17 mg, 0.405 mmol). The reaction was stirred for 3 h at room temperature. Then, the reaction was acidified with trifluoroacetic acid (0.039 mL, 0.510 mmol). Further processing was analogous to Example 64, giving 41 mg of the product as a white fluffy solid (59 mmol, 25% yield relative to 64a).

$^1$H NMR (D$_2$O with internal dioxane reference, 95° C., 500 MHz): $\delta_H$ 3.10-3.16 (cycle, m, 4H); 3.23-3.27 (cycle, m, 4H); 3.28-3.33 (cycle, m, 4H); 3.34 (CH$_2$—COOH, s, 4H); 3.55-3.60 (cycle, m, 4H); 4.81 (CH$_2$-arom., s, 2H); 7.36 (arom., dd, 1H, $^3J_{HH}$=7 Hz, $^4J_{HH}$=2 Hz); 7.57-7.65 (arom., m, 2H); 7.67 (arom., d, 1H, $^3J_{HH}$=9 Hz); 8.50 (arom., d, 1H, $^3J_{HH}$=9 Hz). $^{13}$C{$^1$H} NMR (D$_2$O with internal dioxane reference, 95° C., 125 MHz): $\delta_C$ 44.0 (cycle, s); 49.4 (cycle, s); 50.3 (cycle, s); 53.2 (cycle, s); 55.0 (CH$_2$—COOH, s); 59.5 (CH$_2$-arom., s); 114.2 (arom., s); 120.1 (arom., s); 122.8 (arom., s); 129.6 (arom., s); 129.8 (arom., s); 138.4 (arom., s); 140.1 (arom., s); 149.2 (arom., s); 152.1 (arom., s); 175.2 (CO, s).

HRMS (ESI) m/z: [(M+H)$^+$] (C$_{22}$H$_{32}$N$_5$O$_5$) calculated: 446.2398, found: 446.2399.

Elem. analysis: M·1.7TFA·3.0H$_2$O, calculated: C (44.0), H (5.6), N (10.1), F (14.0), found: C (44.1), H (5.4), N (9.4), F (14.8).

Example 69: Preparation of 2,2'-(4-benzyl-10-(2-hydroxy-5-nitrobenzyl)-1,4,7,10-tetraazacyclododecane-1,7-diyl)diacetic acid (69)

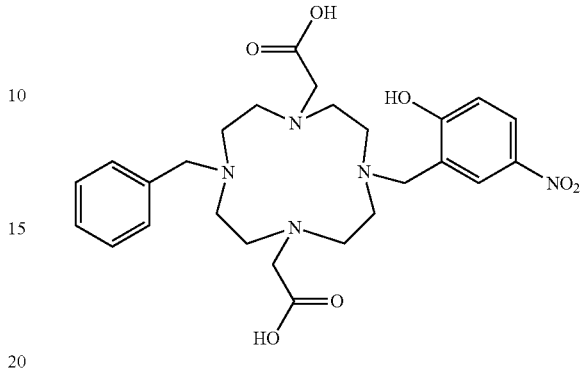

According to procedure in Example 1, reaction of starting compound 55a (304 mg, 0.349 mmol), 2-(bromomethyl)-4-nitrophenol (131 mg, 0.565 mmol) and anhydrous potassium carbonate (292 mg, 2.11 mmol) in acetonitrile (20 mL) gave analogously 193 mg of the product as a pale yellow fluffy solid (0.248 mmol, 71% yield relative to 55a).

$^1$H NMR (DMSO, 25° C., 500 MHz): $\delta_H$ 2.91-3.37 (cycle, m, 16H); 3.45 (CH$_2$—COOH, s, 4H); 4.36-4.77 (CH$_2$-arom., m, 4H); 7.16 (arom., d, 1H, $^3J_{HH}$=9 Hz); 7.41-7.69 (arom., m, 5H); 8.23 (arom., dd, 1H, $^3J_{HH}$=9 Hz, $^4J_{HH}$=3 Hz); 8.57 (arom., d, 1H, $^4J_{HH}$=3 Hz); $^{13}$C{$^1$H} NMR (DMSO, 25° C., 125 MHz): $\delta_C$ 47.3 (cycle, s); 47.8 (cycle, s); 49.3 (cycle, s); 49.6 (cycle, s); 51.0 (CH$_2$-arom., s); 52.8 (CH$_2$—COOH, s); 56.2 (CH$_2$-arom., s); 116.2 (arom., s); 116.7 (arom., s); 127.9 (arom., s); 128.8 (arom., s); 129.2 (arom., s); 130.2 (arom., s); 130.8 (arom., s); 132.4 (arom., s); 139.7 (arom., s); 164.2 (arom., s); 173.0 (CO, s).

HRMS (ESI) m/z: [(M+H)$^+$] (C$_{26}$H$_{36}$N$_5$O$_7$) calculated: 530.2609, found: 530.2610.

Elem. analysis: M·1.8TFA·2.4H$_2$O, calculated: C (45.7), H (5.4), N (9.0), F (13.2), found: C (45.2), H (4.9), N (8.6), F (13.1).

Example 70: Preparation of 2-((7-benzyl-4,10-bis(carboxymethyl)-1,4,7,10-tetraazacyclododecan-1-yl)methyl)pyridine 1-oxide (70)

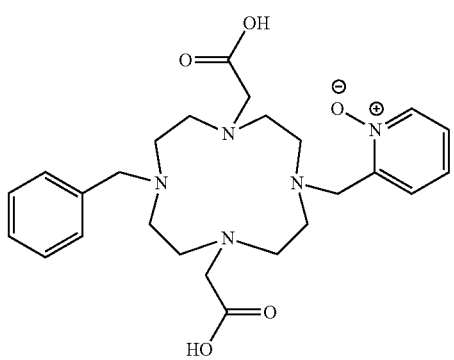 [SMILES: O=C(O)CN1CCN(Cc2ccccc2)CCN(CC(=O)O)CCN(Cc2cccc[n+]2[O-])CC1]

According to procedure in Example 1, reaction of starting compound 55a (301 mg, 0.346 mmol), 2-(chloromethyl)pyridine 1-oxide (78 mg, 0.543 mmol) and anhydrous potas-

Example 71: Preparation of 2,2'-(4-benzyl-10-((6-carboxypyridin-2-yl)methyl)-1,4,7,10-tetraazacyclododecane-1,7-diyl)diacetic acid (71)

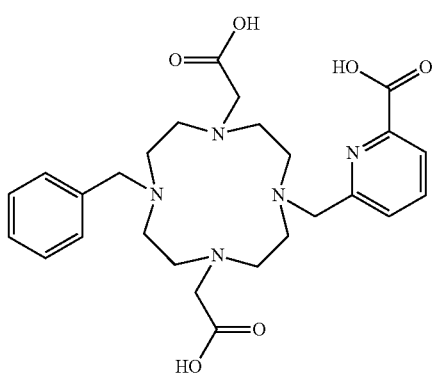 [SMILES: O=C(O)CN1CCN(Cc2ccccc2)CCN(CC(=O)O)CCN(Cc2cccc(C(=O)O)n2)CC1]

According to procedure in Example 12, reaction of starting compound 55a (301 mg, 0.346 mmol), anhydrous potassium carbonate (346 mg, 2.50 mmol) and methyl 6-(chloromethyl)picolinate hydrochloride (101 mg, 0.455 mmol) in anhydrous acetonitrile (20 mL) was carried out. Hydrolysis of the methyl ester group followed in a mixture of acetonitrile (4 mL) and distilled water (2 mL) with addition of 2 M aqueous NaOH (1 mL, 2 mmol). The reaction was stirred for 16 h at room temperature. Then, the reaction was acidified with trifluoroacetic acid (0.191 mL, 2.5 mmol). Further processing was analogous to Example 12, giving 186 mg of the product as a white fluffy solid (0.240 mmol, 69% yield relative to 55a).

HRMS (ESI) m/z: [(M−H)$^-$] ($C_{26}H_{34}N_5O_6$) calculated: 512.2515, found: 512.2510.

Elem. analysis: M·2.0TFA·1.8H$_2$O, calculated: C (46.6), H (5.3), N (9.0), F (14.7), found: C (46.9), H (5.7), N (8.7), F (14.3).

sium carbonate (346 mg, 2.50 mmol) in acetonitrile (20 mL) gave analogously 252 mg of the product as a white fluffy solid (326 mmol, 94% yield relative to 55a).

HRMS (ESI) m/z: [(M−H)$^-$] ($C_{25}H_{34}N_5O_5$) calculated: 484.2565, found: 484.2555.

Elem. analysis: M·2.1TFA·2.7H$_2$O, calculated: C (45.3), H (5.5), N (9.1), F (15.5), found: C (45.6), H (5.3), N (8.7), F (15.6).

Example 72

Preparation of di-tert-butyl 2,2'-(4-(3-(tert-butoxy)-3-oxopropyl)-1,4,7,10-tetraazacyclododecane-1,7-diyl)diacetate (72a)

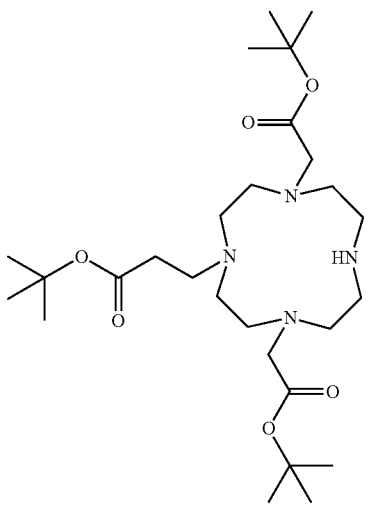 [SMILES: CC(C)(C)OC(=O)CCN1CCN(CC(=O)OC(C)(C)C)CCNCCN(CC(=O)OC(C)(C)C)CC1]

Starting compound A (1.20 g, 3.00 mmol) and anhydrous potassium carbonate (509 mg, 3.68 mmol) were placed into a 100 mL flask under argon atmosphere and anhydrous acetonitrile (30 mL) was added. t-butyl acrylate (500 mg, 3.89 mmol) was dissolved in anhydrous acetonitrile (3 mL) and during 5 minutes dropwise added to the mixture while stirring at room temperature. The reaction mixture was then heated to 50° C. and stirred under argon for 24 hours. The solids were filtered off and the filtrate was evaporated on rotary evaporator. Resulting oil was purified on preparative HPLC (C18 column, acetonitrile/water gradient with 0.1% trifluoroacetic acid in the mobile phase). Fractions containing pure product were pooled, evaporated and dried in high vacuum to give 867 mg of the product as a white powder (1.05 mmol, 35% yield relative to A).

$^1$H NMR (CD$_3$OD, 25° C., 500 MHz): δ$_H$ 1.47 (CH$_3$, s, 9H); 1.50 (CH$_3$, s, 18H); 2.77-2.89 (cycle, m, 2H); 2.89-2.96 (CH$_2$—CH$_2$—COOH, m, 2H); 2.96-3.38 (cycle, m, 10H); 3.39-3.59 (cycle and CH$_2$—COOH, m, 10H); $^{13}$C{$^1$H} NMR (CD$_3$OD, 25° C., 125 MHz): 28.3 (CH$_3$, s); 28.5 (CH$_3$, s); 30.6 (CH$_2$—CH$_2$—COOH, s); 43.8 (cycle, s); 49.5 (cycle, s); 51.0 (cycle, s); 51.3 (CH$_2$—COOH, s); 52.1 (cycle, s); 55.5 (CH$_2$—COOH, s); 83.3 (C—CH$_3$, s); 84.1 (C—CH$_3$, s); 170.4 (CO, s); 173.1 (CO, s).

HRMS (ESI) m/z: [(M+H)$^+$] ($C_{27}H_{53}N_4O_6$) calculated: 529.3960, found: 529.3960.

Elem. analysis: M·2.4TFA·1.3H$_2$O, calculated: C (46.3), H (7.0), N (6.8), F (16.6), found: C (46.0), H (6.7), N (6.6), F (16.6).

Preparation of 2,2'-(4-(2-carboxyethyl)-10-((6-methylpyridin-2-yl)methyl)-1,4,7,10-tetraazacyclododecane-1,7-diyl)diacetic acid (72)

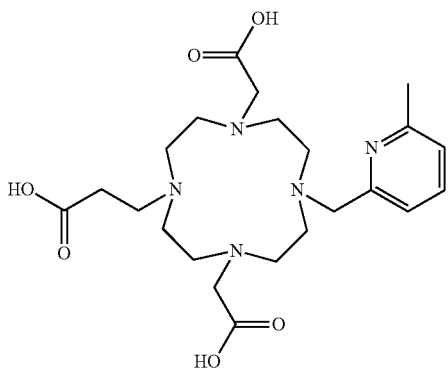 [SMILES: Cc1cccc(CN2CCN(CC(=O)O)CCN(CCC(=O)O)CCN(CC(=O)O)CC2)n1]

According to procedure in Example 1, reaction of starting compound 72a (182 mg, 0.220 mmol), 2-(chloromethyl)-6-methylpyridine hydrochloride (86 mg, 0.483 mmol) and anhydrous potassium carbonate (266 mg, 1.92 mmol) in acetonitrile (10 mL) gave analogously 101 mg of the product as a white fluffy solid (0.123 mmol, 56% yield relative to 72a).

HRMS (ESI) m/z: [(M+H)$^+$] ($C_{22}H_{36}N_5O_6$) calculated: 466.2660, found: 466.2661.

Elem. analysis: M·2.8TFA·1.9H$_2$O, calculated: C (40.5), H (5.1), N (8.6), F (19.5), found: C (40.7), H (4.8), N (8.3), F (19.2).

Example 73: Preparation of 2,2'-(4-((6-bromopyridin-2-yl)methyl)-10-(2-carboxyethyl)-1,4,7,10-tetraazacyclododecane-1,7-diyl)diacetic acid (73)

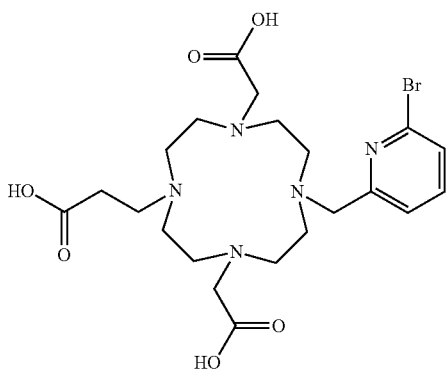 [SMILES: O=C(O)CCN1CCN(CC(=O)O)CCN(Cc2cccc(Br)n2)CCN(CC(=O)O)CC1]

According to procedure in Example 1, reaction of starting compound 72a (120 mg, 0.145 mmol), 2-bromo-6-(chloromethyl)pyridine hydrochloride (39 mg, 0.160 mmol) and anhydrous potassium carbonate (175 mg, 1.27 mmol) in acetonitrile (5 mL) extended for 4 days at 50° C. gave analogously 75 mg of the product as a white fluffy solid (0.093 mmol, 64% yield relative to 72a).

$^1$H NMR (D$_2$O with internal dioxane reference, 95° C., 500 MHz): δ$_H$ 2.97 (CH$_2$—CH$_2$—COOH, t, 2H, $^3J_{HH}$=7 Hz); 3.14-3.29 (cycle, m, 8H); 3.39-3.47 (cycle, m, 4H); 3.51 (CH$_2$—COOH, s, 4H); 3.54-3.60 (cycle, m, 4H); 3.63 (CH$_2$—CH$_2$—COOH, t, 2H, $^3J_{HH}$=7 Hz); 4.60 (CH$_2$-arom., s, 2H); 7.59 (arom., dd, 1H, $^3J_{HH}$=8 Hz, $^4J_{HH}$=1 Hz); 7.75 (arom., d, 1H, $^3J_{HH}$=8 Hz, $^4J_{HH}$=1 Hz); 7.85 (arom., dd, 1H, $^3J_{HH}$=8 Hz, $^3J_{HH}$=8 Hz). $^{13}$C{$^1$H} NMR (D$_2$O with internal dioxane reference, 95° C., 125 MHz): δ$_C$ 28.8 (CH$_2$—CH$_2$—COOH, s); 49.4 (cycle, s); 49.5 (cycle, s); 50.9 (CH$_2$—CH$_2$—COOH, s); 51.4 (cycle, s); 52.5 (cycle, s); 54.5 (CH$_2$—COOH, s); 58.7 (CH$_2$-arom., s); 125.0 (arom., s); 130.4 (arom., s); 141.7 (arom., s); 142.5 (arom., s); 150.9 (arom., s); 173.9 (CO, s); 174.4 (CO, s).

HRMS (ESI) m/z: [(M+H)$^+$] ($C_{21}H_{33}BrN_5O_6$) calculated: 530.1609, found: 530.1609.

Elem. analysis: M·2.2TFA·1.3H$_2$O, calculated: C (37.9), H (4.6), N (8.7), F (15.6), Br (9.9) found: C (38.3), H (4.4), N (8.4), F (15.7), Br (9.5).

Example 74: Preparation of 2,2'-(4-(2-carboxyethyl)-10-((6-chloropyridin-2-yl)methyl)-1,4,7,10-tetraazacyclododecane-1,7-diyl)diacetic acid (74)

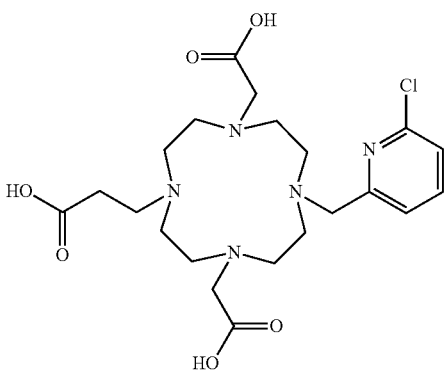 [SMILES: O=C(O)CCN1CCN(CC(=O)O)CCN(Cc2cccc(Cl)n2)CCN(CC(=O)O)CC1]

According to procedure in Example 1, reaction of starting compound 72a (100 mg, 0.121 mmol), 2-chloro-6-(chloromethyl)pyridine hydrochloride (26 mg, 0.132 mmol) and anhydrous potassium carbonate (146 mg, 1.06 mmol) in acetonitrile (5 mL) carried out at 40° C. gave analogously 83 mg of the product as a white fluffy solid (0.108 mmol, 89% yield relative to 72a).

$^1$H NMR (D$_2$O with internal dioxane reference, 95° C., 500 MHz): δ$_H$ 2.97 (CH$_2$—CH$_2$—COOH, t, 2H, $^3J_{HH}$=7 Hz); 3.12-3.30 (cycle, m, 8H); 3.40-3.48 (cycle, m, 4H); 3.52 (CH$_2$—COOH, s, 4H); 3.56-3.62 (cycle, m, 4H); 3.64 (CH$_2$—CH$_2$—COOH, t, 2H, $^3J_{HH}$=7 Hz); 4.63 (CH$_2$-arom., s, 2H); 7.56 (arom., d, 1H, $^3J_{HH}$=8 Hz); 7.60 (arom., d, 1H, $^3J_{HH}$=8 Hz); 7.97 (arom., t, 1H, $^3J_{HH}$=8 Hz). $^{13}$C{$^1$H} NMR (D$_2$O with internal dioxane reference, 95° C., 125 MHz): δ$_C$ 28.7 (CH$_2$—CH$_2$—COOH, s); 49.3 (cycle, s); 49.4 (cycle, s); 50.9 (CH$_2$—CH$_2$—COOH, s); 51.4 (cycle, s); 52.6 (cycle, s); 54.5 (CH$_2$—COOH, s); 58.6 (CH$_2$-arom., s); 124.5 (arom., s); 126.5 (arom., s); 142.1 (arom., s); 150.3 (arom., s); 151.9 (arom., s); 173.8 (CO, s); 174.3 (CO, s).

HRMS (ESI) m/z: [(M+Na)$^+$] ($C_{21}H_{32}ClN_5NaO_6$) calculated: 508.1933, found: 508.1935.

Elem. analysis: M·2.3TFA·1.3H$_2$O, calculated: C (39.9), H (4.8), N (9.1), F (17.0), Cl (4.6) found: C (40.3), H (4.4), N (8.6), F (16.8), Cl (4.6).

Example 75: Preparation of 2,2'-(4-(2-carboxyethyl)-10-((6-fluoropyridin-2-yl)methyl)-1,4,7,10-tetraazacyclododecane-1,7-diyl)diacetic acid (75)

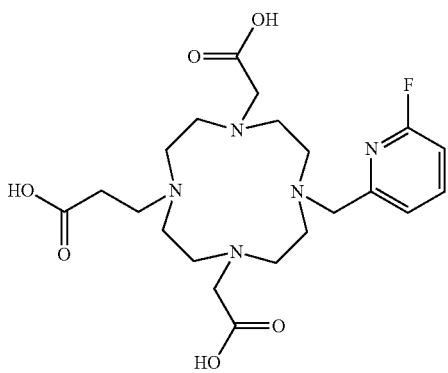 [SMILES: O=C(O)CCN1CCN(CC(=O)O)CCN(Cc2cccc(F)n2)CCN(CC(=O)O)CC1]

According to procedure in Example 1, reaction of starting compound 72a (100 mg, 0.121 mmol), 2-(chloromethyl)-6-fluoropyridine hydrochloride (36 mg, 0.197 mmol) and anhydrous potassium carbonate (128 mg, 0.926 mmol) in acetonitrile (5 mL) extended for 2 days at 50° C. gave analogously 22 mg of the product as a white fluffy solid (0.030 mmol, 25% yield relative to 72a).

HRMS (ESI) m/z: [(M+H)$^+$] ($C_{21}H_{33}FN_5O_6$) calculated: 470.2410, found: 470.2408.

Elem. analysis: M·1.9TFA·2.7H$_2$O, calculated: C (40.5), H (5.4), N (9.5), F (17.3), found: C (40.1), H (4.9), N (9.1), F (17.2).

Example 76: Preparation of 2,2'-(4-(2-carboxyethyl)-10-(pyridin-2-ylmethyl)-1,4,7,10-tetraazacyclododecane-1,7-diyl)diacetic acid (76)

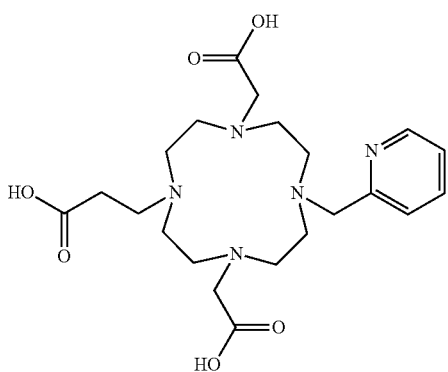 [SMILES: O=C(O)CCN1CCN(CC(=O)O)CCN(Cc2ccccn2)CCN(CC(=O)O)CC1]

According to procedure in Example 1, reaction of starting compound 72a (100 mg, 0.121 mmol), 2-(chloromethyl)pyridine hydrochloride (30 mg, 0.183 mmol) and anhydrous potassium carbonate (146 mg, 1.06 mmol) in acetonitrile (5 mL) extended for 2 days at 40° C. gave analogously 32 mg of the product as a white fluffy solid (0.045 mmol, 37% yield relative to 72a).

$^1$H NMR (D$_2$O with internal dioxane reference, 95° C., 500 MHz): δ$_H$ 2.84 (CH$_2$—CH$_2$—COOH, t, 2H, $^3$J$_{HH}$=7 Hz); 3.21-3.41 (cycle and CH$_2$—CH$_2$—COOH, m, 18H); 3.59 (N—CH$_2$—COOH, s, 4H); 4.40 (CH$_2$-arom., s, 2H); 7.76-7.88 (arom., m, 2H); 8.26-8.35 (arom., m, 1H); 8.73-8.78 (arom., m, 1H); $^{13}$C{$^1$H}NMR (D$_2$O with internal dioxane reference, 95° C., 125 MHz): δ$_C$ 29.5 (CH$_2$—CH$_2$—COOH, s); 49.7 (cycle, s); 49.9 (CH$_2$—CH$_2$—COOH, s); 50.7 (cycle, s); 50.8 (cycle, s); 50.9 (cycle, s); 55.6 (CH$_2$—COOH, s); 57.1 (CH$_2$-arom., s); 126.7 (arom., s); 127.3 (arom., s); 143.7 (arom., s); 147.3 (arom., s); 149.5 (arom., s); 172.2 (CO, s); 175.2 (CO, s).

HRMS (ESI) m/z: [(M−H)$^-$] ($C_{21}H_{32}N_5O_6$) calculated: 450.2358, found: 450.2357.

Elem. analysis: M·2.1TFA·1.5H$_2$O, calculated: C (42.2), H (5.3), N (9.8), F (16.7), found: C (42.1), H (5.0), N (9.4), F (16.4).

Example 77: Preparation of 2-((7-(2-carboxyethyl)-4,10-bis(carboxymethyl)-1,4,7,10-tetraazacyclododecan-1-yl)methyl)pyridine 1-oxide (77)

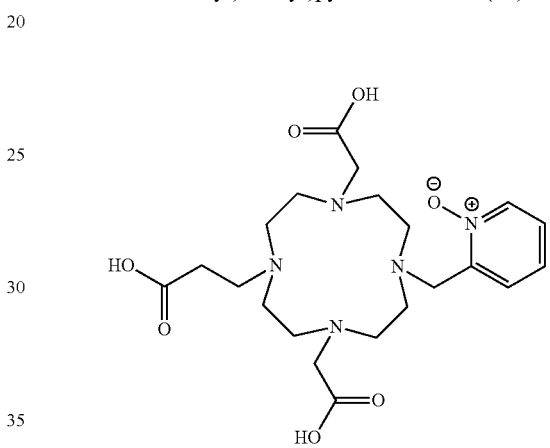

According to procedure in Example 1, reaction of starting compound 72a (100 mg, 0.121 mmol), 2-(chloromethyl)pyridine 1-oxide (38 mg, 0.265 mmol) and anhydrous potassium carbonate (146 mg, 1.06 mmol) in acetonitrile (5 mL) extended for 4 days at 40° C. gave analogously 65 mg of the product as a white fluffy solid (0.085 mmol, 70% yield relative to 72a).

$^1$H NMR (D$_2$O with internal dioxane reference, 95° C., 500 MHz): δ$_H$ 3.05 (CH$_2$—CH$_2$—COOH, t, 2H, $^3$J$_{HH}$=7 Hz); 3.15-3.30 (cycle, m, 8H); 3.39 (CH$_2$—COOH, s, 4H); 3.40-3.55 (cycle, m, 8H); 3.69 (CH$_2$—CH$_2$—COOH, t, 2H, $^3$J$_{HH}$=7 Hz); 4.77 (CH$_2$-arom., s, 2H); 7.76 (arom., ddd, 1H, $^3$J$_{HH}$=8 Hz, $^3$J$_{HH}$=6 Hz, $^4$J$_{HH}$=2 Hz); 7.82 (arom., td, 1H, $^3$J$_{HH}$=8 Hz, $^4$J$_{HH}$=1 Hz); 7.86 (arom., dd, 1H, $^3$J$_{HH}$=8 Hz, $^4$J$_{HH}$=2 Hz); 8.44 (arom., dd, 1H, $^3$J$_{HH}$=6 Hz, $^4$J$_{HH}$=1 Hz). $^{13}$C{$^1$H} NMR (D$_2$O with internal dioxane reference, 95° C., 125 MHz): δ$_C$ 29.0 (CH$_2$—CH$_2$—COOH, s); 49.4 (cycle, s); 49.5 (cycle, s); 51.2 (CH$_2$—CH$_2$—COOH, s); 51.9 (cycle, s); 53.0 (cycle, s); 53.4 (CH$_2$—COOH, s); 55.5 (CH$_2$-arom., s); 129.5 (arom., s); 130.7 (arom., s); 140.0 (arom., s); 140.8 (arom., s); 173.8 (CO, s); 173.9 (CO, s).

HRMS (ESI) m/z: [(M+H)$^+$] ($C_{21}H_{34}N_5O_7$) calculated: 468.2453, found: 468.2454.

Elem. analysis: M·2.4TFA·1.5H$_2$O, calculated: C (40.3), H (5.0), N (9.1), F (17.8), found: C (40.3), H (4.8), N (8.9), F (17.6).

Example 78: Preparation of 2-((4,10-bis(carboxymethyl)-7-(2-hydroxy-5-nitrobenzyl)-1,4,7,10-tetraazacyclododecan-1-yl)methyl)pyridine 1-oxide (78)

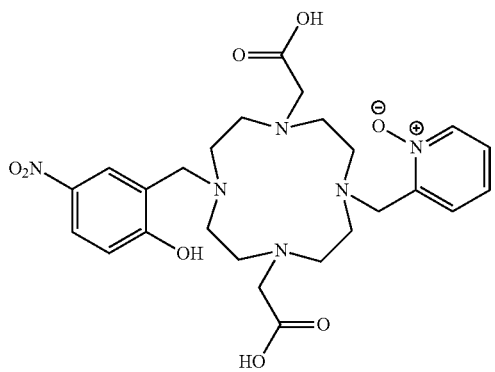 [SMILES: O=C(O)CN1CCN(Cc2cc([N+](=O)[O-])ccc2O)CCN(CC(=O)O)CCN(Cc2cccc[n+]2[O-])CC1]

Starting compound A (400 mg, 1.00 mmol) was placed into a 25 mL flask under argon atmosphere and anhydrous acetonitrile (10 mL) was added. 2-(chloromethyl)pyridine 1-oxide (72 mg, 0.500 mmol) was dissolved in anhydrous acetonitrile (1 mL) and during 5 minutes dropwise added to the mixture while stirring. The reaction mixture was stirred under argon for 4 days at room temperature. Then, DIPEA (0.174 mL, 1.00 mmol) was added, followed by a solution of 2-(bromomethyl)-4-nitrophenol (185 mg, 0.800 mmol) in anhydrous acetonitrile (1 mL). The reaction mixture was stirred under argon for 24 hours at room temperature. The solvent was evaporated on rotary evaporator. Resulting oil was purified on preparative HPLC (C18 column, acetonitrile/water gradient with 0.1% trifluoroacetic acid in the mobile phase). Fractions containing pure product protected on acetate arms with tert.butyl ester groups were pooled, evaporated and dried in high vacuum. The residue was dissolved in neat trifluoroacetic acid (3 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 191 mg of the product as a pale yellow fluffy solid (0.221 mmol, 22% yield relative to A).

HRMS (ESI) m/z: [(M–H)$^-$] ($C_{25}H_{33}N_6O_8$) calculated: 545.2365, found: 545.2363.

Elem. analysis: M·2.3TFA·3.0$H_2O$, calculated: C (41.2), H (4.9), N (9.7), F (15.2), found: C (41.5), H (4.5), N (9.3), F (14.8).

Example 79: Preparation of 2-((4,10-bis(carboxymethyl)-7-((6-carboxypyridin-2-yl)methyl)-1,4,7,10-tetraazacyclododecan-1-yl)methyl)pyridine 1-oxide (79)

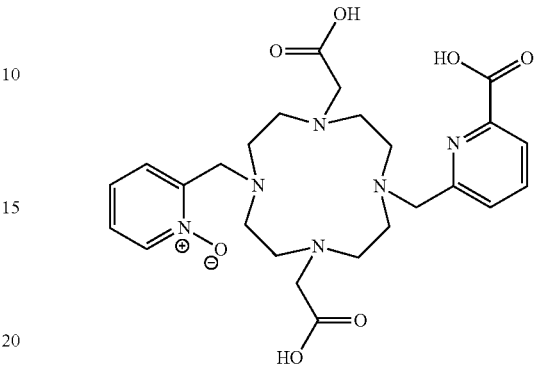

Starting compound A (300 mg, 0.750 mmol) and anhydrous potassium carbonate (414 mg, 3.00 mmol) were placed into a 50 mL flask under argon atmosphere and anhydrous acetonitrile (10 mL) was added. 2-(chloromethyl)pyridine 1-oxide (65 mg, 0.450 mmol) was dissolved in anhydrous acetonitrile (1 mL) and during 5 minutes dropwise added to the mixture while stirring. The reaction mixture was stirred under argon for 24 hours at 40° C. Then, a solution of methyl 6-(chloromethyl)picolinate hydrochloride (266 mg, 1.20 mmol) in anhydrous acetonitrile (1 mL) was added. The reaction mixture was stirred under argon for 24 hours at 40° C. The solids were filtered off and distilled water (10 mL) was added, followed by LiOH·$H_2O$ (94 mg, 2.25 mmol). The mixture was stirred for 1 hour at room temperature. Then, trifluoroacetic acid (0.435 mL, 5.7 mmol) was added and the solvents were evaporated on rotary evaporator. Resulting oil was purified on preparative HPLC (C18 column, acetonitrile/water gradient with 0.1% trifluoroacetic acid in the mobile phase). Fractions containing intermediate with free carboxylic group on pyridine were pooled, evaporated and dried in high vacuum. The residue was dissolved in neat trifluoroacetic acid (3 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 108 mg of the product as a white fluffy solid (0.134 mmol, 18% yield relative to A).

$^1$H NMR ($D_2O$ with internal dioxane reference, 95° C., 500 MHz): $\delta_H$ 3.10-3.18 (cycle, m, 8H); 3.21 ($CH_2$—COOH, s, 4H); 3.28-3.36 (cycle, m, 4H); 3.40-3.47 (cycle, m, 4H); 4.61 ($CH_2$-arom., s, 2H); 4.63 ($CH_2$-arom., s, 2H); 7.61 (arom., ddd, 1H, $^3J_{HH}$=8 Hz, $^3J_{HH}$=6 Hz, $^4J_{HH}$=2 Hz); 7.69 (arom., td, 1H, $^3J_{HH}$=8 Hz, $^4J_{HH}$=1 Hz); 7.74 (arom., ddd, 1H, $^3J_{HH}$=8 Hz, $^4J_{HH}$=2 Hz, $^4J_{HH}$=2 Hz); 7.81 (arom., dd, 1H, $^3J_{HH}$=8 Hz, $^4J_{HH}$=1 Hz); 8.11 (arom., t, 1H, $^3J_{HH}$=8 Hz); 8.16 (arom., dd, 1H, $^3J_{HH}$=8 Hz, $^4J_{HH}$=1 Hz); 8.27 (arom., ddd, 1H, $^3J_{HH}$=6 Hz, $^4J_{HH}$=1 Hz, $^4J_{HH}$=1 Hz). $^{13}$C{$^1$H} NMR ($D_2O$ with internal dioxane reference, 95° C., 125 MHz): $\delta_C$ 49.3 (cycle, s); 49.5 (cycle, s); 52.5 (cycle, s); 52.6 (cycle, s); 53.6 ($CH_2$—COOH, s); 55.0 ($CH_2$-arom., s); 59.0 ($CH_2$-arom., s); 126.6 (arom., s); 129.4 (arom., s); 130.1 (arom., s); 130.7 (arom., s); 132.3 (arom., s); 140.6

(arom., s); 140.9 (arom., s); 141.2 (arom., s); 148.2 (arom., s); 150.5 (arom., s); 167.7 (CO, s); 173.4 (CO, s).

HRMS (ESI) m/z: [(M+H)$^+$] ($C_{25}H_{35}N_6O_7$) calculated: 531.2562, found: 531.2564.

Elem. analysis: M·2.2TFA·1.5H$_2$O, calculated: C (43.7), H (4.9), N (10.4), F (15.5), found: C (44.1), H (4.9), N (9.9), F (15.5).

Example 80: Preparation of 2,2'-(4-((6-carboxypyridin-2-yl)methyl)-10-(2-hydroxy-5-nitrobenzyl)-1,4,7,10-tetraazacyclododecane-1,7-diyl)diacetic acid (80)

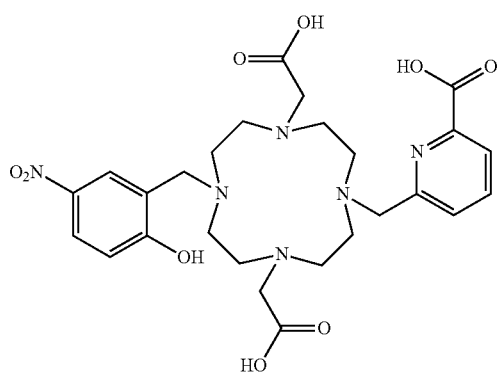 [SMILES: O=C(O)CN1CCN(Cc2cccc(C(=O)O)n2)CCN(CC(=O)O)CCN(Cc2cc([N+](=O)[O-])ccc2O)CC1]

Starting compound A (200 mg, 0.500 mmol) was placed into a 50 mL flask under argon atmosphere and anhydrous acetonitrile (20 mL) was added. 2-(bromomethyl)-4-nitrophenol (81 mg, 0.349 mmol) was dissolved in anhydrous acetonitrile (1 mL) and during 5 minutes dropwise added to the mixture while stirring. The reaction mixture was stirred under argon for 24 hours at room temperature. Then, DIPEA (0.900 mL, 5.17 mmol) and a solution of methyl 6-(chloromethyl)picolinate hydrochloride (180 mg, 0.811 mmol) in anhydrous acetonitrile (2 mL) was added. The reaction mixture was stirred under argon for 24 hours at 40° C. The solvents were evaporated on rotary evaporator and the resulting oil was purified on preparative HPLC (C18 column, acetonitrile/water gradient with 0.1% trifluoroacetic acid in the mobile phase). Fractions containing pure intermediate with all three carboxylic groups protected were pooled, evaporated and dried in high vacuum. The residue was dissolved in a mixture of acetonitrile (2.5 mL) and distilled water (2.5 mL) and LiOH·H$_2$O (39 mg, 0.929 mmol) was added. The mixture was stirred for 3 hours at room temperature. Trifluoroacetic acid (0.070 mL, 0.915 mmol) was added and the solvents were evaporated on rotary evaporator. Resulting oil was purified on preparative HPLC (C18 column, acetonitrile/water gradient with 0.1% trifluoroacetic acid in the mobile phase). Fractions containing intermediate with free carboxylic group on pyridine were pooled, evaporated and dried in high vacuum. The residue was dissolved in neat trifluoroacetic acid (2 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 79 mg of the product as a white fluffy solid (0.094 mmol, 19% yield relative to A).

$^1$H NMR (D$_2$O with internal dioxane reference, 95° C., 500 MHz): δ$_H$ 3.15-3.35 (cycle and CH$_2$—COOH, m, 12H); 3.45-3.54 (cycle, m, 4H); 3.54-3.62 (cycle, m, 4H); 4.61 (CH$_2$-arom., s, 2H); 4.73 (CH$_2$-arom., s, 2H); 7.19 (arom., d, 1H, $^3J_{HH}$=9 Hz); 7.85 (arom., dd, 1H, $^3J_{HH}$=8 Hz, $^4J_{HH}$=1 Hz); 8.20 (arom., t, 1H, $^3J_{HH}$=8 Hz); 8.28 (arom., dd, 1H, $^3J_{HH}$=8 Hz, $^4J_{HH}$=1 Hz); 8.31 (arom., dd, 1H, $^3J_{HH}$=9 Hz, $^4J_{HH}$=3 Hz); 8.42 (arom., d, 1H, $^4J_{HH}$=3 Hz); $^{13}C\{^1H\}$ NMR (D$_2$O with internal dioxane reference, 95° C., 125 MHz): δ$_C$ 48.8 (cycle, s); 49.2 (cycle, s); 51.7 (cycle, s); 52.3 (cycle, s); 54.0 (CH$_2$—COOH, s); 54.4 (CH$_2$-arom., s); 59.0 (CH$_2$-arom., s); 117.1 (arom., s); 117.5 (arom., s); 126.6 (arom., s); 129.0 (arom., s); 129.6 (arom., s); 129.8 (arom., s); 140.9 (arom., s); 141.5 (arom., s); 149.0 (arom., s); 150.1 (arom., s); 162.5 (arom., s); 168.3 (CO, s); 173.8 (CO, s).

HRMS (ESI) m/z: [(M+H)$^+$] ($C_{26}H_{35}N_6O_9$) calculated: 575.2460, found: 575.2462.

Elem. analysis: M·2.1TFA·1.7H$_2$O, calculated: C (42.9), H (4.7), N (10.0), F (14.2), found: C (42.7), H (4.4), N (9.7), F (13.9).

Example 81: Preparation of 2,2'-(4-((6-carboxypyridin-2-yl)methyl)-10-((6-chloropyridin-2-yl)methyl)-1,4,7,10-tetraazacyclododecane-1,7-diyl)diacetic acid (81)

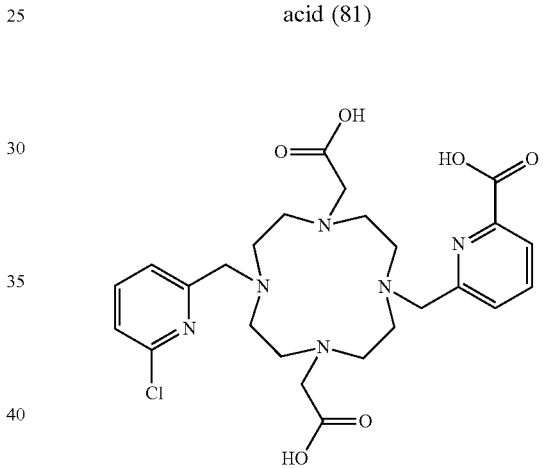

Starting compound A (90 mg, 0.225 mmol) and anhydrous potassium carbonate (124 mg, 0.900 mmol) were placed into a 25 mL flask under argon atmosphere and anhydrous acetonitrile (4 mL) was added. 2-chloro-6-(chloromethyl)pyridine hydrochloride (27 mg, 0.135 mmol) was dissolved in anhydrous acetonitrile (1 mL) and during 5 minutes dropwise added to the mixture while stirring. The reaction mixture was stirred under argon for 24 hours at 40° C. Solution of methyl 6-(chloromethyl)picolinate hydrochloride (80 mg, 0.359 mmol) in anhydrous acetonitrile (1 mL) was added and the reaction mixture was stirred under argon for another 24 hours at 40° C. The solids were filtered off and distilled water (4 mL) was added to the filtrate, followed by addition of LiOH·H$_2$O (28 mg, 0.674 mmol). The reaction mixture was stirred at room temperature for 30 minutes. Then, trifluoroacetic acid was added (0.130 mL, 1.71 mmol) and the solvents were evaporated on rotary evaporator. The resulting oil was purified on preparative HPLC (C18 column, acetonitrile/water gradient with 0.1% trifluoroacetic acid in the mobile phase). Fractions containing pure intermediate with free carboxylic group on pyridine were pooled, evaporated and dried in high vacuum. The residue was dissolved in neat trifluoroacetic acid (2 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 45 mg of the product as a white fluffy solid (0.057 mmol, 25% yield relative to A).

$^1$H NMR (D$_2$O with internal dioxane reference, 95° C., 500 MHz): $\delta_H$ 3.21-3.31 (cycle, m, 8H); 3.44 (CH$_2$—COOH, s, 4H); 3.51-3.56 (cycle, m, 4H); 3.56-3.61 (cycle, m, 4H); 4.56 (CH$_2$-arom., s, 2H); 4.67 (CH$_2$-arom., s, 2H); 7.58 (arom., dm, 1H, $^3J_{HH}$=8 Hz); 7.59 (arom., dm, 1H, $^3J_{HH}$=8 Hz); 7.89 (arom., dd, 1H, $^3J_{HH}$=8 Hz, $^4J_{HH}$=1 Hz); 7.97 (arom., dd, 1H, $^3J_{HH}$=8 Hz, $^3J_{HH}$=8 Hz); 8.20 (arom., t, 1H, $^3J_{HH}$=8 Hz); 8.26 (arom., dd, 1H, $^3J_{HH}$=8 Hz, $^4J_{HH}$=1 Hz). $^{13}$C{$^1$H} NMR (D$_2$O with internal dioxane reference, 95° C., 125 MHz): $\delta_C$ 49.4 (cycle, s); 49.5 (cycle, s); 51.9 (cycle, s); 52.1 (cycle, s); 54.4 (CH$_2$—COOH, s); 58.5 (CH$_2$-arom., s); 58.8 (CH$_2$-arom., s); 124.8 (arom., s); 126.3 (arom., s); 126.6 (arom., s); 129.7 (arom., s); 141.1 (arom., s); 142.1 (arom., s); 148.5 (arom., s); 150.4 (arom., s); 150.8 (arom., s); 151.7 (arom., s); 167.7 (CO, s); 173.7 (CO, s).

HRMS (ESI) m/z: [(M–H)$^-$] (C$_{25}$H$_{32}$ClN$_6$O$_6$) calculated: 547.2077, found: 547.2075.

Elem. analysis: M·1.9TFA·1.7H$_2$O, calculated: C (43.4), H (4.8), N (10.6), F (13.6), Cl (4.5) found: C (43.4), H (4.3), N (10.0), F (13.3), Cl (4.4).

Example 82: Preparation of di-tert-butyl 2,2'-(4-((6-(methoxycarbonyl)pyridin-2-yl)methyl)-1,4,7,10-tetraazacyclododecane-1,7-diyl)diacetate (82a)

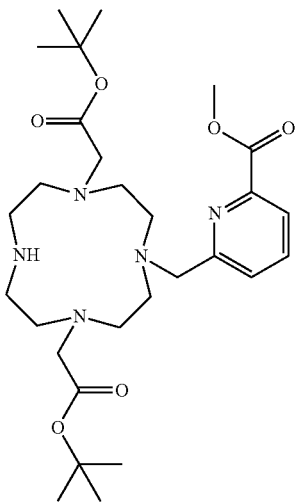 [SMILES: COC(=O)c1cccc(CN2CCN(CC(=O)OC(C)(C)C)CCNCCN(CC(=O)OC(C)(C)C)CC2)n1]

Starting compound A (400 mg, 1.00 mmol) was placed into a 50 mL flask under argon atmosphere and anhydrous acetonitrile (10 mL) was added. Solution of methyl 6-(chloromethyl)picolinate hydrochloride (111 mg, 0.500 mmol) in anhydrous acetonitrile (2 mL) was added dropwise during 5 minutes and the reaction mixture was stirred under argon for 4 days at room temperature. The solids were filtered off and the filtrate evaporated on rotary evaporator. The resulting oil was purified on preparative HPLC (C18 column, acetonitrile/water gradient with 0.1% trifluoroacetic acid in the mobile phase). Fractions containing pure product were pooled, evaporated and dried in high vacuum, giving 339 mg of thick yellow oil (0.339 mmol, 68% yield relative to methyl 6-(chloromethyl)picolinate hydrochloride).

$^1$H NMR (CD$_3$OD, 25° C., 500 MHz): $\delta_H$ 1.37 (CH$_3$, s, 18H); 2.92-3.08 (cycle, m, 4H); 3.08-3.45 (cycle, m, 12H); 3.57-3.78 (CH$_2$—CO, m, 4H); 4.08 (CH$_3$, s, 3H); 4.80 (CH$_2$-arom., s, 2H); 7.76 (arom., dd, 1H, $^3J_{HH}$=8 Hz, $^4J_{HH}$=1 Hz); 8.16 (arom., t, 1H, $^3J_{HH}$=8 Hz); 8.23 (arom., dd, 1H, $^3J_{HH}$=8 Hz, $^4J_{HH}$=1 Hz); $^{13}$C{$^1$H} NMR (CD$_3$OD, 25° C., 125 MHz): 28.3 (cycle, s); 48.9 (cycle, s); 49.5 (cycle, s); 53.7 (CH$_2$—CO, s); 53.9 (CH$_3$, s); 54.7 (cycle, s); 58.0 (CH$_2$-arom., s); 126.9 (arom., s); 128.5 (arom., s); 141.1 (arom., s); 147.6 (arom., s); 152.1 (arom., s); 166.3 (CO, s); 171.2 (CO, s).

HRMS (ESI) m/z: [(M+H)$^+$] (C$_{28}$H$_{48}$N$_5$O$_6$) calculated: 550.3599, found: 550.3600.

Elem. analysis: M·3.8TFA·0.9H$_2$O, calculated: C (42.8), H (5.3), N (7.0), F (21.7), found: C (42.5), H (5.0), N (6.9), F (21.4).

Preparation of 2,2'-(4-((6-bromopyridin-2-yl)methyl)-10-((6-carboxypyridin-2-yl)methy)-1,4,7,10-tetraazacyclododecane-1,7-diyl)diacetic acid (82)

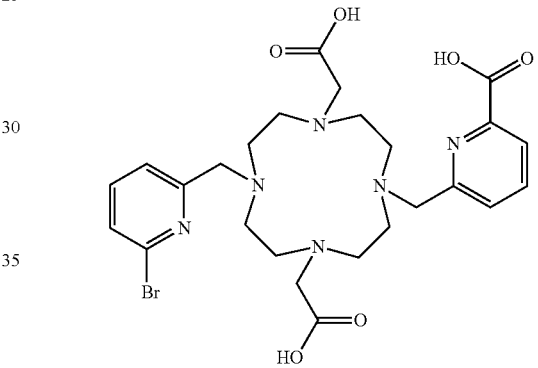

Starting compound 82a (107 mg, 0.107 mmol) and anhydrous potassium carbonate (152 mg, 1.10 mmol) were placed into a 25 mL flask under argon atmosphere and anhydrous acetonitrile (5 mL) was added. Solution of 2-bromo-6-(chloromethyl)pyridine hydrochloride (33 mg, 0.137 mmol) in anhydrous acetonitrile (1 mL) was added and the reaction mixture was stirred under argon for 4 days at 50° C. The solids were filtered off and distilled water (4 mL) was added to the filtrate, followed by addition of LiOH·H$_2$O (17 mg, 0.414 mmol). The reaction mixture was stirred at room temperature for 30 minutes. Then, trifluoroacetic acid was added (0.063 mL, 0.828 mmol) and the solvents were evaporated on rotary evaporator. The resulting oil was purified on preparative HPLC (C18 column, acetonitrile/water gradient with 0.1% trifluoroacetic acid in the mobile phase). Fractions containing pure intermediate with free carboxylic group on pyridine were pooled, evaporated and dried in high vacuum. The residue was dissolved in neat trifluoroacetic acid (2 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 62 mg of the product as a white fluffy solid (0.073 mmol, 68% yield relative to 82a).

¹H NMR (D₂O with internal dioxane reference, 95° C., 500 MHz): $\delta_H$ 3.19-3.31 (cycle, m, 8H); 3.43 (CH₂—COOH, s, 4H); 3.48-3.55 (cycle, m, 4H); 3.55-3.62 (cycle, m, 4H); 4.55 (CH₂-arom., s, 2H); 4.66 (CH₂-arom., s, 2H); 7.60 (arom., d, 1H, $^3J_{HH}$=8 Hz); 7.73 (arom., d, 1H, $^3J_{HH}$=8 Hz); 7.84 (arom., t, 1H, $^3J_{HH}$=8 Hz); 7.88 (arom., d, 1H, $^3J_{HH}$=8 Hz); 8.19 (arom., t, 1H, $^3J_{HH}$=8 Hz); 8.24 (arom., d, 1H, $^3J_{HH}$=8 Hz). ¹³C{¹H} NMR (D₂O with internal dioxane reference, 95° C., 125 MHz): 49.3 (cycle, s); 49.4 (cycle, s); 52.0 (cycle, s); 52.2 (cycle, s); 54.4 (CH₂—COOH, s); 58.6 (CH₂-arom., s); 58.9 (CH₂-arom., s); 125.3 (arom., s); 126.7 (arom., s); 129.8 (arom., s); 130.2 (arom., s); 141.2 (arom., s); 141.7 (arom., s); 142.3 (arom., s); 148.5 (arom., s); 150.4 (arom., s); 151.3 (arom., s); 167.7 (CO, s); 173.7 (CO, s).

HRMS (ESI) m/z: [(M+H)⁺] ($C_{25}H_{34}BrN_6O_6$) calculated: 593.1718, found: 593.1718.

Elem. analysis: M·2.0TFA·1.5H₂O, calculated: C (41.1), H (4.5), N (9.9), F (13.4), Br (9.4) found: C (40.9), H (4.1), N (9.6), F (13.3), Br (9.0).

Example 83: Preparation of 2,2'-(4-((6-carboxypyridin-2-yl)methyl)-10-((6-methylpyridin-2-yl)methyl)-1,4,7,10-tetraazacyclododecane-1,7-diyl)diacetic acid (83)

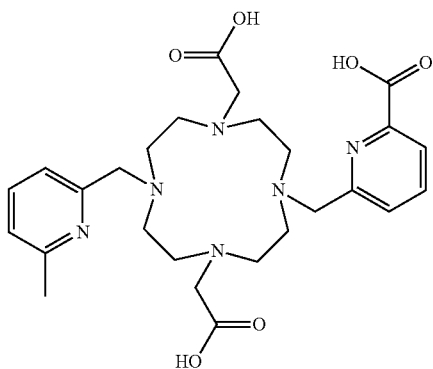 [SMILES: Cc1cccc(CN2CCN(CC(=O)O)CCN(Cc3cccc(C(=O)O)n3)CCN(CC(=O)O)CC2)n1]

Starting compound A (224 mg, 0.560 mmol) and anhydrous potassium carbonate (280 mg, 0.900 mmol) were placed into a 25 mL flask under argon atmosphere and anhydrous acetonitrile (5 mL) was added. 2-(chloromethyl)-6-methylpyridine hydrochloride (100 mg, 0.560 mmol) was dissolved in anhydrous acetonitrile (1 mL) and during 5 minutes dropwise added to the mixture while stirring. The reaction mixture was stirred under argon for 24 hours at room temperature. The solids were filtered off and the solvent evaporated. The resulting oil was purified on preparative HPLC (C18 column, acetonitrile/water gradient with 0.1% trifluoroacetic acid in the mobile phase). Fractions containing the intermediate with one (6-methylpyridin-2-yl)methyl arm were pooled, evaporated and dried in high vacuum. The resulting residue, anhydrous potassium carbonate (298 mg, 2.16 mmol) and methyl 6-(chloromethyl) picolinate hydrochloride (46 mg, 0.207 mmol) were placed under argon and anhydrous acetonitrile (5 mL) was added. The mixture was stirred for 24 hours at 60° C. The solids were filtered off and distilled water (5 mL) was added, followed by addition of LiOH·H₂O (23 mg, 0.548 mmol). The reaction mixture was stirred at room temperature for 60 minutes. Then, trifluoroacetic acid was added (0.043 mL, 0.562 mmol) and the solvents were evaporated on rotary evaporator. The resulting oil was purified on preparative HPLC (C18 column, acetonitrile/water gradient with 0.1% trifluoroacetic acid in the mobile phase). Fractions containing pure intermediate with free carboxylic group on pyridine were pooled, evaporated and dried in high vacuum. The residue was dissolved in neat trifluoroacetic acid (2 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 93 mg of the product as a white fluffy solid (0.113 mmol, 20% yield relative to A).

HRMS (ESI) m/z: [(M+H)⁺] ($C_{26}H_{37}N_6O_6$) calculated: 529.2769, found: 529.2771.

Elem. analysis: M·2.4TFA·1.2H₂O, calculated: C (44.9), H (5.0), N (10.2), F (16.6), found: C (45.1), H (4.9), N (10.0), F (16.4).

Example 84: Preparation of 2,2'-(4-((6-carboxypyridin-2-yl)methyl)-10-(pyridin-4-ylmethyl)-1,4,7,10-tetraazacyclododecane-1,7-diyl)diacetic acid (84)

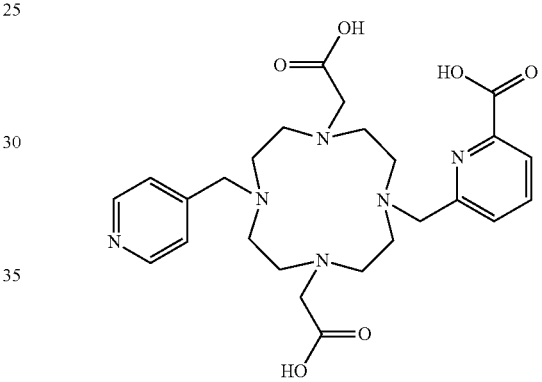

Starting compound A (300 mg, 0.749 mmol) and anhydrous potassium carbonate (520 mg, 3.76 mmol) were placed into a 50 mL flask under argon atmosphere and anhydrous acetonitrile (15 mL) was added. Methyl 6-(chloromethyl)picolinate hydrochloride (100 mg, 0.450 mmol) was dissolved in anhydrous acetonitrile (2.5 mL) and during 5 minutes dropwise added to the mixture while stirring. The reaction mixture was stirred under argon for 24 hours at room temperature. Then, solution of 4-(chloromethyl)pyridine hydrochloride (197 mg, 1.20 mmol) in anhydrous acetonitrile (2.5 mL) was added and the reaction mixture was stirred under argon for 3 days at room temperature. The solids were filtered off and the solvent evaporated. The resulting oil was purified on preparative HPLC (C18 column, acetonitrile/water gradient with 0.1% trifluoroacetic acid in the mobile phase). Fractions containing the product with all carboxylic groups in ester form were pooled, evaporated and dried in high vacuum. The residue was dissolved in a mixture of acetonitrile (5 mL) and distilled water (5 mL) and LiOH·H₂O (74 mg, 1.76 mmol) was added. The reaction mixture was stirred at room temperature for 2 hours. Then, trifluoroacetic acid was added (0.220 mL, 2.88 mmol) and the solvents were evaporated on rotary evaporator. The resulting oil was purified on preparative HPLC (C18 column, acetonitrile/water gradient with 0.1% trifluoroacetic acid in the mobile phase). Fractions containing pure intermediate with free carboxylic group on pyridine were pooled, evaporated and dried in high vacuum. The residue was dissolved in neat trifluoroacetic acid (3 mL) and stirred for 24 h at room temperature. Trifluoroacetic acid was evaporated on rotary evaporator. The residue was dissolved in distilled water (2 ml), loaded onto a solid-phase extraction column (C18 reversed phase, 500 mg) and the product eluted with distilled water (10 mL). The eluate was lyophilized, residue redissolved in distilled water (2 mL) and lyophilized again, giving 142 mg of the product as a white fluffy solid (0.160 mmol, 21% yield relative to A).

$^1$H NMR (D$_2$O with internal dioxane reference, 25° C., 500 MHz): $\delta_H$ 2.68-2.89 (cycle, m, 2H); 2.89-3.63 (cycle+CH$_2$—COOH, m, 18H); 3.93 (CH$_2$-arom, bs, 2H); 4.12 (CH$_2$-arom, bs, 2H); 8.14-8.21 (arom., m, 3H); 8.36 (arom., dd, 1H, $^3J_{HH}$=8 Hz, $^4J_{HH}$=1 Hz); 8.49 (arom., t, 1H, $^3J_{HH}$=8 Hz); 8.75-8.80 (arom., m, 2H); $^{13}$C{$^1$H} NMR (D$_2$O with internal dioxane reference, 25° C., 125 MHz): $\delta_C$ 47.9 (cycle, bs); 48.10 (cycle, bs); 50.6 (cycle, bs); 50.8 (cycle, bs); 54.7 (CH$_2$-arom., s); 55.4 (CH$_2$—COOH, s); 56.9 (CH$_2$-arom., s); 126.6 (arom., s); 128.4 (arom., s); 131.4 (arom., s); 141.6 (arom., s); 145.9 (arom., s); 146.5 (arom., s); 151.3 (arom., s); 163.9 (arom., s); 168.5 (CO, s).

HRMS (ESI) m/z: [(M+H)$^+$] (C$_{25}$H$_{35}$N$_6$O$_6$) calculated: 515.2613, found: 515.2613.

Elem. analysis: M·2.9TFA·2.2H$_2$O, calculated: C (41.8), H (4.7), N (9.5), F (18.7), found: C (42.2), H (4.6), N (9.1), F (18.6).

Example 85: Preparation of 2,2'-(4-((6-carboxypyridin-2-yl)methyl)-10-methyl-1,4,7,10-tetraazacyclododecane-1,7-diyl)diacetic acid (85)

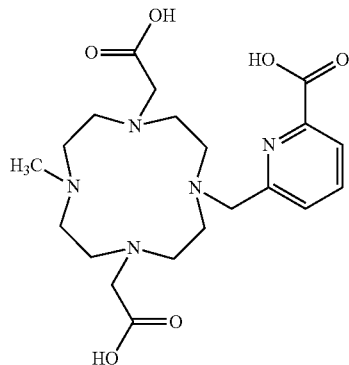 [SMILES: CN1CCN(CC(=O)O)CCN(Cc2cccc(C(=O)O)n2)CCN(CC(=O)O)CC1]

Procedure in Example 84 was used with minor modification. Reaction of starting compound A (200 mg, 0.500 mmol), anhydrous potassium carbonate (345 mg, 2.50 mmol) and iodomethane (43 mg, 0.303 mmol) in anhydrous acetonitrile (15 mL) was stirred for 24 hours at room temperature. Then, solution of methyl 6-(chloromethyl)picolinate hydrochloride (180 mg, 0.810 mmol) in anhydrous acetonitrile (2.5 mL) was added and the reaction mixture was stirred under argon for 24 hours at 40° C. Further processing, including the hydrolysis of the methyl ester group using LiOH·H$_2$O (30 mg, 0.714 mmol) was analogous to Example 84, giving 50 mg of the product as a white fluffy solid (0.072 mmol, 14% yield relative to A).

$^1$H NMR (D$_2$O with internal dioxane reference, 95° C., 500 MHz): $\delta_H$ 3.06 (CH$_3$, s, 3H); 3.11-3.57 (cycle and CH$_2$—COOH, m, 16H); 3.57-3.61 (cycle, m, 4H); 4.72 (CH$_2$-arom., s, 2H); 7.82 (arom., dd, 1H, $^3J_{HH}$=8 Hz, $^4J_{HH}$=1 Hz); 8.18 (arom., t, 1H, $^3J_{HH}$=8 Hz); 8.25 (arom., dd, 1H, $^3J_{HH}$=8 Hz, $^4J_{HH}$=1 Hz). $^{13}$C{$^1$H} NMR (D$_2$O with internal dioxane reference, 95° C., 125 MHz): $\delta_C$ 43.7 (CH$_3$, s); 49.2 (cycle, s); 49.3 (cycle, s); 52.9 (cycle, s); 54.1 (cycle, s); 54.5 (CH$_2$—COOH, s); 58.8 (CH$_2$-arom., s); 126.7 (arom., s); 129.0 (arom., s); 141.0 (arom., s); 148.6 (arom., s); 149.9 (arom., s); 167.8 (CO, s); 174.6 (CO, s).

HRMS (ESI) m/z: [(M+H)$^+$] (C$_{20}$H$_{32}$N$_5$O$_6$) calculated: 438.2347, found: 438.2348.

Elem. analysis: M·1.9TFA·2.2H$_2$O, calculated: C (41.2), H (5.4), N (10.1), F (15.6), found: C (41.1), H (5.0), N (9.8), F (15.4).

Example 86: Preparation of 2,2'-(4-((6-chloropyridin-2-yl)methyl)-10-(phosphonomethyl)-1,4,7,10-tetraazacyclododecane-1,7-diyl)diacetic acid (86)

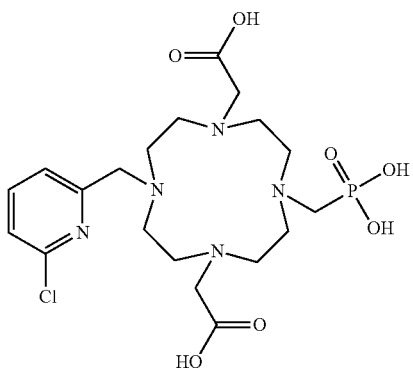 [SMILES: O=C(O)CN1CCN(Cc2cccc(Cl)n2)CCN(CC(=O)O)CCN(CP(=O)(O)O)CC1]

Starting compound A (300 mg, 0.749 mmol), paraformaldehyde (15 mg, 0.500 mmol) and triethylphosphite (417 mg, 2.508 mmol) were placed into a 4 mL vial under argon atmosphere and the reaction mixture was stirred for 5 days at room temperature. The mixture was purified on preparative HPLC (C18 column, acetonitrile/water gradient with 0.1% trifluoroacetic acid in the mobile phase). Fractions containing the intermediate with one (diethoxyphosphoryl)methyl arm were pooled, evaporated and dried in high vacuum. The resulting residue, anhydrous potassium carbonate (224 mg, 1.62 mmol) and 2-(bromomethyl)-6-chloropyridine (53 mg, 0.257 mmol) were placed under argon and anhydrous acetonitrile (6 mL) was added. The reaction mixture was stirred for 24 hours at room temperature. The solids were filtered off and the solvent evaporated. The resulting oil was purified on preparative HPLC (C18 column, acetonitrile/water gradient with 0.1% trifluoroacetic acid in the mobile phase). Fractions containing pure, fully protected product were pooled, evaporated and dried in high vacuum. The residue was dissolved in 6 M HCl (10 mL) and heated at 90° C. for 2 days. The mixture was evaporated to dryness, residue dissolved in distilled water (5 mL) and evaporated again (repeated two-times), followed by lyophilization from distilled water (2 mL, repeated two-times), giving 74 mg of the product as a white fluffy solid (0.113 mmol, 15% yield relative to A).

$^1$H NMR (D$_2$O with internal dioxane reference, 95° C., 500 MHz): $\delta_H$ 3.17-3.27 (cycle, m, 8H); 3.52 (CH$_2$—P, d, 2H, $^2J_{HP}$=13 Hz); 3.54-3.59 (cycle, m, 4H); 3.60 (CH$_2$—COOH, s, 4H); 3.62-3.69 (cycle, m, 4H); 7.57 (arom., dd, 1H, $^3J_{HH}$=8 Hz, $^4J_{HH}$=1 Hz); 7.60 (arom., dd, 1H, $^3J_{HH}$=8 Hz, $^4J_{HH}$=1 Hz); 7.97 (arom., dd, 1H, $^3J_{HH}$=8 Hz, $^3J_{HH}$=8 Hz). $^{13}$C{$^1$H} NMR (D$_2$O with internal dioxane reference, 95° C., 125 MHz): $\delta_C$ 49.4 (cycle, s); 49.6 (cycle, s); 51.7

(CH$_2$—P, d, $^1J_{CP}$=137 Hz); 52.4 (cycle, s); 53.0 (cycle, $^3J_{CP}$=3 Hz); 54.6 (CH$_2$—COOH, s); 58.6 (CH$_2$-arom., s); 124.7 (arom., s); 126.5 (arom., s); 142.2 (arom., s); 150.6 (arom., s); 151.9 (arom., s); 174.3 (CO, s). $^{31}$P{$^1$H} NMR (D$_2$O with external H$_3$PO$_4$ reference, 95° C., 202 MHz): δ$_P$ 8.1 ppm (s).

HRMS (ESI) m/z: [(M+H)$^+$] (C$_{19}$H$_{32}$ClN$_5$O$_7$P) calculated: 508.1723, found: 508.1725.

Elem. analysis: M·3.0HCl·2.0H$_2$O, calculated: C (34.9), H (5.9), N (10.7), found: C (35.0), H (5.6), N (10.5).

Example 87: Preparation of 2,2'-(4-((6-bromopyridin-2-yl)methyl)-10-((hydroxy(methyl)phosphoryl)methyl)-1,4,7,10-tetraazacyclododecane-1,7-diyl) diacetic acid (87)

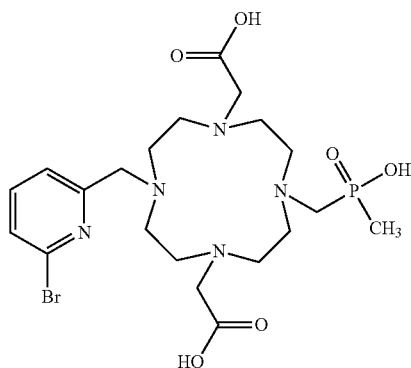 [SMILES: CP(=O)(O)CN1CCN(CC(=O)O)CCN(Cc2cccc(Br)n2)CCN(CC(=O)O)CC1]

Starting compound A (510 mg, 1.27 mmol) and anhydrous potassium carbonate (352 mg, 2.55 mmol) were placed into a 50 mL flask under argon atmosphere and anhydrous acetonitrile (20 mL) was added. 2-bromo-6-(chloromethyl)pyridine hydrochloride (155 mg, 0.640 mmol) was dissolved in anhydrous acetonitrile (2.5 mL) and during 5 minutes dropwise added to the mixture while stirring. The reaction mixture was stirred under argon for 3 days at room temperature. The solids were filtered off and the solvent evaporated. The resulting oil was purified on preparative HPLC (C18 column, acetonitrile/water gradient with 0.1% trifluoroacetic acid in the mobile phase). Fractions containing pure mono-alkylated intermediate in tert.butyl ester form were pooled and the solvent evaporated. The resulting residue, isopropyl methylphosphinate (133 mg, 1.09 mmol) and paraformaldehyde (65 mg, 2.167 mmol) were placed under argon and anhydrous acetonitrile (5 mL) was added. The reaction mixture was stirred for 3 days at room temperature. The solvent was evaporated and resulting oil was purified on preparative HPLC (C18 column, acetonitrile/water gradient with 0.1% trifluoroacetic acid in the mobile phase). Fractions containing the product with both carboxylic groups and phosphinate in ester form were pooled, evaporated and dried in high vacuum. The residue was dissolved in 6 M HCl (2 mL) and heated at 70° C. for 2 days. The mixture was evaporated to dryness, residue dissolved in distilled water (5 mL) and evaporated again (repeated two-times), followed by lyophilization from distilled water (2 mL, repeated two-times), giving 33 mg of the product as a white fluffy solid (0.047 mmol, 7% yield relative to 2-bromo-6-(chloromethyl)pyridine hydrochloride).

$^1$H NMR (D$_2$O with internal dioxane reference, 95° C., 500 MHz): δ$_H$ 1.63 (CH$_3$, d, 3H, $^2J_{HP}$=15 Hz); 3.22-3.34 (cycle, m, 8H); 3.49-3.55 (cycle, m, 4H); 3.60 (CH$_2$—P, d, 2H, $^2J_{HP}$=8 Hz); 3.62-3.67 (cycle, m, 4H); 3.68 (CH$_2$—COOH, s, 4H); 4.53 (CH$_2$-arom., s, 2H); 7.62 (arom., d, $^3J_{HH}$=8 Hz); 7.75 (arom., d, $^3J_{HH}$=8 Hz); 7.85 (arom., t, $^3J_{HH}$=8 Hz); $^{13}$C{$^1$H} NMR (D$_2$O with internal dioxane reference, 95° C., 125 MHz): 16.7 (CH$_3$, d, $^1J_{CP}$=97 Hz); 49.7 (cycle, s); 49.8 (cycle, s); 51.8 (cycle, s); 53.1 (cycle, s); 53.3 (CH$_2$—P, $^1J_{CP}$=89 Hz); 54.6 (CH$_2$—COOH, s); 58.5 (CH$_2$-arom., s); 125.0 (arom., s); 130.1 (arom., s); 141.7 (arom., s); 142.2 (arom., s); 151.8 (arom., s); 173.4 (CO, s); $^{31}$P{$^1$H} NMR (D$_2$O without reference, 95° C., 202 MHz): 39.3 ppm (s).

HRMS (ESI) m/z: [(M+H)$^+$] (C$_{20}$H$_{34}$BrN$_5$O$_6$P) calculated: 550.1425, found: 550.1427.

Elem. analysis: M·3.0HCl·2.0H$_2$O, calculated: C (34.5), H (5.8), N (10.1), found: C (34.1), H (5.6), N (10.0).

Example 88: Preparation of 2,2'-(4-((6-chloropyridin-2-yl)methyl)-10-((hydroxy(methyl)phosphoryl)methyl)-1,4,7,10-tetraazacyclododecane-1,7-diyl) diacetic acid (88)

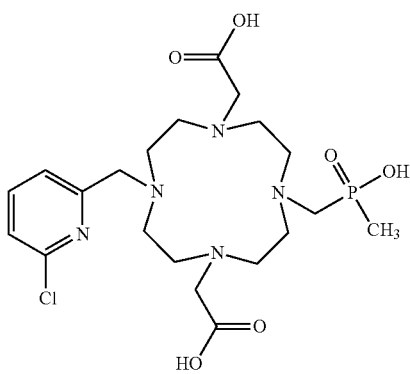 [SMILES: CP(=O)(O)CN1CCN(CC(=O)O)CCN(Cc2cccc(Cl)n2)CCN(CC(=O)O)CC1]

According to procedure in Example 87, reaction of starting compound A (550 mg, 1.37 mmol), 2-(bromomethyl)-6-chloropyridine (250 mg, 0.810 mmol) and anhydrous potassium carbonate (380 mg, 2.75 mmol) in acetonitrile (20 mL), followed by reaction with isopropyl methylphosphinate (55 mg, 0.450 mmol) and paraformaldehyde (90 mg, 3.00 mmol) in anhydrous acetonitrile (5 mL) extended for 9 days at 40° C. gave analogously 47 mg of the product as a white fluffy solid (0.071 mmol, 9% yield relative to 2-(bromomethyl)-6-chloropyridine).

HRMS (ESI) m/z: [(M−H)$^-$] (C$_{20}$H$_{32}$ClN$_5$O$_6$P) calculated: 504.1784, found: 504.1785.

Elem. analysis: M·3.5HCl·1.5H$_2$O, calculated: C (36.4), H (6.0), N (10.6), P (4.7), Cl (24.2), found: C (35.9), H (5.5), N (10.8), P (4.4), Cl (23.8).

Example 89: Preparation of 2,2',2''-(10-(2-oxo-2-(pyridin-2-yl)ethyl)-1,4,7,10-tetraazacyclododecane-1,4,7-triyl)triacetic acid (89)

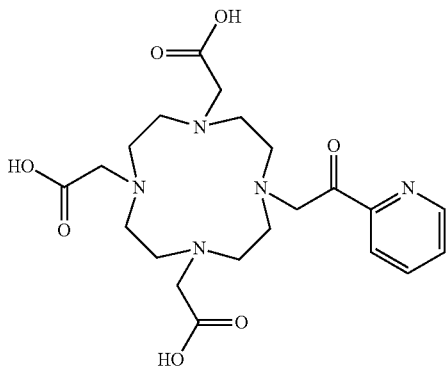 [SMILES: O=C(O)CN1CCN(CC(=O)O)CCN(CC(=O)c2ccccn2)CCN(CC(=O)O)CC1]

According to procedure in Example 1, reaction of starting compound B (200 mg, 0.336 mmol), 2-bromo-1-(pyridin-2-yl)ethan-1-one hydrobromide (105 mg, 0.374 mmol) and anhydrous potassium carbonate (185 mg, 1.34 mmol) in acetonitrile (15 mL) gave analogously 116 mg of the product as a white fluffy solid (0.146 mmol, 43% yield relative to B).

HRMS (ESI) m/z: [(M+H)$^+$] ($C_{21}H_{32}N_5O_7$) calculated: 466.2296, found: 466.2297. Elem. analysis: M·2.9TFA, calculated: C (40.4), H (4.3), N (8.8), F (20.8), found: C (40.1), H (4.2), N (9.2), F (20.8).

Example 90: Preparation of 2,2',2''-(10-(pyrimidin-2-ylmethyl)-1,4,7,10-tetraazacyclododecane-1,4,7-triyl)triacetic acid (90)

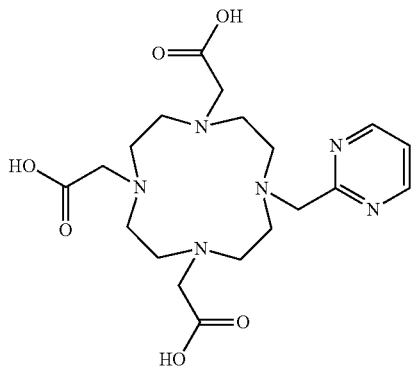 [SMILES: O=C(O)CN1CCN(CC(=O)O)CCN(Cc2ncccn2)CCN(CC(=O)O)CC1]

According to procedure in Example 1, reaction of starting compound B (200 mg, 0.336 mmol), 2-(chloromethyl)pyrimidine hydrochloride (83 mg, 0.503 mmol) and anhydrous potassium carbonate (185 mg, 1.34 mmol) in acetonitrile (15 mL) extended to 2 days at 60° C. gave analogously 24 mg of the product as a white fluffy solid (0.038 mmol, 11% yield relative to B).

$^1$H NMR (D$_2$O with internal dioxane reference, 95° C., 500 MHz): $\delta_H$ 3.27-3.36 (cycle, m, 8H); 3.36-3.43 (cycle, m, 4H); 3.46-3.52 (cycle, m, 4H); 3.69 (CH$_2$—COOH, bs, 4H); 3.91 (CH$_2$—COOH, s, 2H); 4.58 (CH$_2$-arom., s, 2H, undergoes slow exchange for deuterium); 7.58 (arom., t, 1H, $^3J_{HH}$=5 Hz); 8.86 (arom., d, 2H, $^3J_{HH}$=5 Hz). $^{13}$C{$^1$H} NMR (D$_2$O with internal dioxane reference, 95° C., 125 MHz): $\delta_C$ 50.0 (cycle, s); 50.3 (cycle, s); 51.2 (cycle, s); 51.7 (cycle, s); 54.9 (CH$_2$—COOH, s); 56.2 (CH$_2$—COOH, s); 58.5 (CH$_2$-arom., s, undergoes slow deuteration); 122.0 (arom., s); 158.9 (arom., s); 166.3 (arom., s); 171.3 (CO, s); 172.5 (CO, s).

HRMS (ESI) m/z: [(M+H)$^+$] ($C_{19}H_{31}N_6O_6$) calculated: 439.2300, found: 439.2300. Elem. analysis: M·1.3TFA·2.2H$_2$O, calculated: C (41.4), H (5.7), N (13.4), F (11.8), found: C (41.2), H (5.2), N (12.9), F (11.7).

Example 91

Preparation of benzyl (S)-2-((methylsulfonyl)oxy)propanoate (91a)

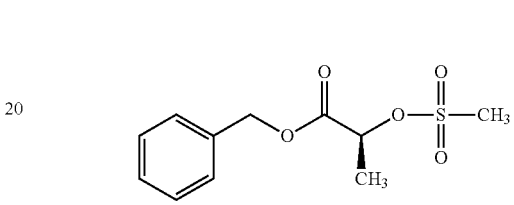

Benzyl (S)-2-((methylsulfonyl)oxy)propanoate (1.00 g, 5.55 mmol), and triethylamine (726 mg, 7.18 mmol) were dissolved in anhydrous tetrahydrofurane (10 mL) under argon and cooled to 5° C. Mesyl chloride (666 mg, 5.82 mmol) was added dropwise while stirring over period of 10 min. The reaction mixture was let to warm up to room temperature and was stirred for 24 hours. The reaction mixture was concentrated on rotary evaporator and partitioned between dichloromethane (15 mL) and water (20 mL). The aqueous phase was then washed with dichloromethane (2×15 mL). Combined organic phases were dried with Na$_2$SO$_4$, filtered and solvent was evaporated, giving 1.33 g of product as colorless oil (5.15 mmol, 93% yield relative to benzyl (S)-2-((methylsulfonyl)oxy)propanoate).

$^1$H NMR (CDCl$_3$, 25° C., 500 MHz): $\delta_H$ 1.64 (CH$_3$—CH, d, 3H, $^3J_{HH}$=7 Hz); 3.12 (CH$_3$—S, s, 3H); 5.19 (CH—CH$_3$, q, 1H, $^3J_{HH}$=7 Hz); 5.23-5.29 (CH$_2$, m, 2H); 7.33-7.45 (arom., m, 5H).

HRMS (ESI) m/z: [(M+H)$^+$] ($C_{11}H_{14}NaO_5S$) calculated: 281.0454, found: 281.0455.

Preparation of 2,2'-(4-(1-carboxyethyl)-10-((6-chloropyridin-2-yl)methyl)-1,4,7,10-tetraazacyclododecane-1,7-diyl)diacetic acid (91)

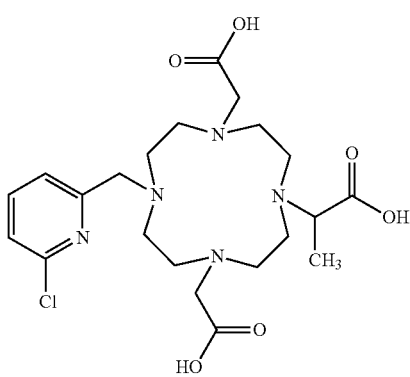 [SMILES: CC(C(=O)O)N1CCN(CC(=O)O)CCN(Cc2cccc(Cl)n2)CCN(CC(=O)O)CC1]

Starting compound A (300 mg, 0.749 mmol), benzyl (S)-2-((methylsulfonyl)oxy)propanoate (212 mg, 0.821 mmol) and anhydrous potassium carbonate (414 mg, 3.00 mmol) were mixed in anhydrous acetonitrile (20 mL) and stirred for 4 days at room temperature. The solids were filtered off, the filtrate evaporated and the resulting residue was purified on preparative HPLC (C18 column, acetonitrile/water gradient with 0.1% trifluoroacetic acid in the mobile phase). Fractions containing the mono-alkylated intermediate were combined, evaporated and dried in high vacuum. The resulting residue, 2-(bromomethyl)-6-chloropyridine (32 mg, 0.104 mmol) and anhydrous potassium carbonate (60 mg, 0.434 mmol) were mixed in anhydrous acetonitrile (3 mL) and stirred for 24 hours at room temperature. The solids were filtered off and the filtrate was purified on preparative HPLC as above. Fractions containing the product in the form of ester were combined and evaporated on rotary evaporator. The residue was dissolved in 6 M HCl (5 mL) and heated to 80° C. for 2 days. The mixture was evaporated to dryness, residue dissolved in distilled water (5 mL) and evaporated again (repeated two-times), followed by lyophilization from distilled water (2 mL, repeated two-times), giving 28 mg of the product as a white fluffy solid (0.043 mmol, 6% yield relative to A).

$^1$H NMR (D$_2$O with internal dioxane reference, 95° C., 500 MHz): $\delta_H$ 1.60 (CH$_3$, d, 3H, $^3J_{HH}$=7 Hz); 3.08-3.22 (cycle, m, 4H); 3.24-3.71 (cycle+CH$_2$—COOH, m, 16H); 4.36 (CH—CH$_3$, q, 1H, $^3J_{HH}$=7 Hz); 4.39 (CH$_2$-arom., d, 1H, $^2J_{HH}$=14 Hz); 4.67 (CH$_2$-arom., d, 1H, $^2J_{HH}$=14 Hz); 7.55-7.58 (arom., m, 2H); 7.94 (arom., t, 1H, $^3J_{HH}$=8 Hz).

HRMS (ESI) m/z: [(M+H)$^+$] (C$_{21}$H$_{33}$ClN$_5$O$_6$) calculated: 486.2214, found: 486.2116. Elem. analysis: M·3.4HCl·2.2H$_2$O, calculated: C (38.8), H (6.2), N (10.8), Cl (24.0), found: C (38.7), H (6.1), N (10.9), Cl (24.0).

Example 92: 2,2'-(4-((6-chloropyridin-2-yl)methyl)-10-(2-(methylsulfonamido)ethyl)-1,4,7,10-tetraazacyclododecane-1,7-diyl)diacetic acid (92)

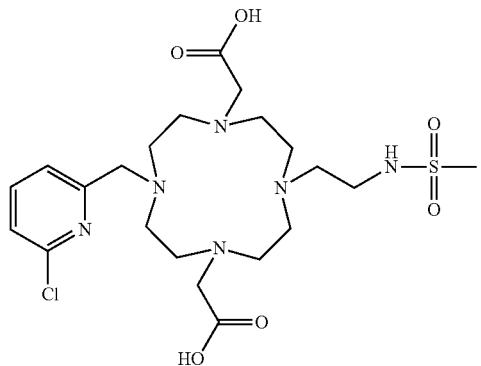 [SMILES: CS(=O)(=O)NCCN1CCN(CC(=O)O)CCN(Cc2cccc(Cl)n2)CCN(CC(=O)O)CC1]

Procedure in Example 91 was used with minor modification. Reaction of starting compound A (300 mg, 0.749 mmol), 2-(methylsulfonamido)ethyl methanesulfonate (179 mg, 0.824 mmol, prepared according to Harvey, P. et al. (2013), Chem. Sci., 4(11), 4251-4258) and anhydrous potassium carbonate (414 mg, 3.00 mmol) in acetonitrile (20 mL) was followed by reaction with 2-(bromomethyl)-6-chloropyridine (146 mg, 0.473 mmol) and anhydrous potassium carbonate (327 mg, 2.37 mmol) in anhydrous acetonitrile (15 mL) as in Example 91. The product in the form of tert.butyl ester was then dissolved in trifluoroacetic acid (3 mL) and processed analogously to Example 1, giving 100 mg of the product as a white fluffy solid (0.130 mmol, 17% yield relative to A).

$^1$H NMR (D$_2$O with internal dioxane reference, 95° C., 500 MHz): $\delta_H$ 3.15 (CH$_3$, s, 3H); 3.28-3.30 (cycle, m, 8H); 3.47-3.62 (cycle+CH$_2$—COOH+CH$_2$—CH$_2$—NH—S, m, 16H); 4.57 (CH$_2$-arom., s, 2H); 7.57 (arom., dd, 1H, $^3J_{HH}$=8 Hz, $^4J_{HH}$=1 Hz); 7.60 (arom., dd, 1H, $^3J_{HH}$=8 Hz, $^4J_{HH}$=1 Hz); 7.96 (arom., t, 1H, $^3J_{HH}$=8 Hz). $^{13}$C{$^1$H} NMR (D$_2$O with internal dioxane reference, 95° C., 125 MHz): $\delta_C$ 38.1 (CH$_2$—NH—S, s); 39.7 (CH$_3$, s); 49.7 (cycle, s); 49.8 (cycle, s); 51.7 (cycle, s); 52.5 (cycle, s); 54.6 (CH$_2$—CH$_2$—NH—S, s); 55.0 (CH$_2$—COOH, s); 58.7 (CH$_2$-arom., s); 124.7 (arom., s); 126.5 (arom., s); 142.3 (arom., s); 150.8 (arom., s); 152.0 (arom., s); 174.4 (CO, s).

HRMS (ESI) m/z: [(M+H)$^+$] (C$_{21}$H$_{36}$ClN$_6$O$_6$S) calculated: 535.2100, found: 535.2102. Elem. analysis: M·1.9TFA·1.9H$_2$O, calculated: C (38.6), H (5.3), N (9.1), F (14.0), S (4.2), Cl (4.6), found: C (37.9), H (4.8), N (10.2), F (13.6), S (3.9), Cl (5.0).

Example 93: Preparation of 4-carboxy-2-((4,7,10-tris(2-(tert-butoxy)-2-oxoethyl)-1,4,7,10-tetraazacyclododecan-1-yl)methyl)pyridine 1-oxide salt with N,N-diisopropylethylamine (93a)

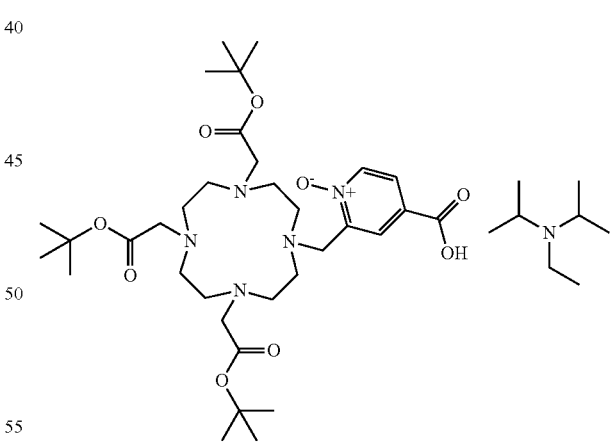

Compound was synthesized according to published procedure [Polasek M. et al. (2009), Bioconjugate Chem. 20(11), 2142-2153]. NMR and MS spectra agreed with those reported in literature.

Preparation of 4-(butylcarbamoyl)-2-((4,7,10-tris(carboxymethyl)-1,4,7,10-tetraazacyclododecan-1-yl)methyl)pyridine 1-oxide (93)

Example 94: Preparation of 4-(hexylcarbamoyl)-2-((4,7,10-tris(carboxymethyl)-1,4,7,10-tetraazacyclododecan-1-yl)methyl)pyridine 1-oxide (94)

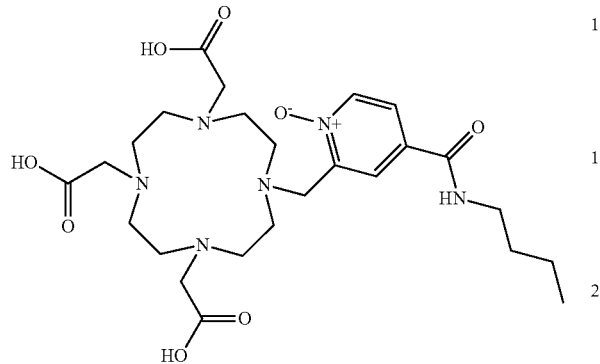

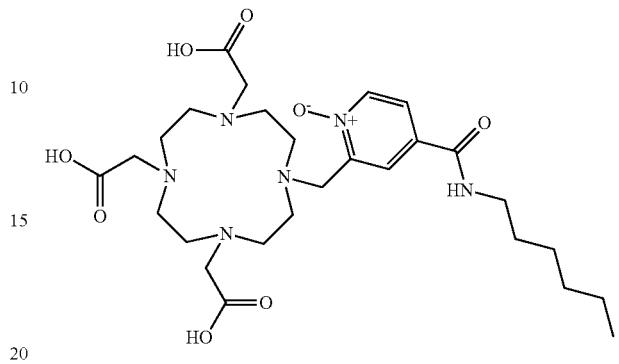

Starting compound 93a (75 mg, 0.094 mmol), 4-(dimethylamino)pyridine (11.5 mg, 0.094 mmol) and 1-butylamine (34.5 mg, 0.472 mmol) were dissolved in acetonitrile (1.5 mL). HATU (53.8 mg, 0.142 mmol) was added and the mixture was stirred for 1 hour at room temperature. Then water (0.5 mL) was added and the solution was purified on preparative HPLC (C18 column, acetonitrile/water gradient with 0.1% trifluoroacetic acid in the mobile phase). Fractions containing pure product in the form of tert.butyl ester were pooled, evaporated and dried in high vacuum. The residue was a dissolved in neat trifluoroacetic acid (2 mL) and stirred for 24 h at room temperature. Trifluoroacetic acid was evaporated on rotary evaporator. The residue was dissolved in 20% acetonitrile in water (2 ml) and purified on preparative HPLC (as above). Fractions with pure product were pooled, concentrated on rotary evaporator, lyophilized, redissolved in distilled water (2 mL) and lyophilized again, giving 53.8 mg of the product as a white fluffy solid (0.071 mmol, 76% yield relative to 93a).

$^1$H NMR ($d_6$-DMSO, 95° C., 500 MHz): $\delta_H$ 0.93 (CH$_3$, t, $^3J_{HH}$=7.4 Hz, 3H); 1.33-1.41 (CH$_2$-aliph., m, 2H); 1.53-1.59 (CH$_2$-aliph., m, 2H); 3.02-3.06 (cycle, m, 4H); 3.07-3.12 (cycle, m, 8H); 3.14-3.19 (cycle, m, 4H); 3.28-3.34 (CH$_2$-aliph., m, 2H); 3.61 (CH$_2$—COOH, s, 4H); 3.72 (CH$_2$—COOH, s, 2H); 4.25 (CH$_2$-arom., s, 2H); 7.87-7.89 (arom., m, 1H); 8.07-8.08 (arom., m, 1H); 8.34-8.36 (arom., m, 1H); 8.46-8.53 (CO—NH, m, 1H). $^{13}$C{$^1$H} NMR ($d_6$-DMSO, 95° C., 125 MHz): $\delta_C$ 14.0 (CH$_3$, s); 20.1 (CH$_2$-aliph., s); 31.6 (CH$_2$-aliph., s); 39.8 (CH$_2$—NH—CO, s); 50.8 (cycle, s); 51.1 (cycle, s); 51.4 (cycle, s); 51.4 (cycle, s); 53.7 (CH$_2$-arom., s); 54.0 (CH$_2$—COOH, s); 55.2 (CH$_2$—COOH, s); 124.8 (arom., s); 127.4 (arom., s); 131.6 (arom., s); 140.1 (arom., s); 145.0 (arom., s); 163.4 (CO); 171.0 (2×CO).

HRMS (ESI) m/z: [(M−H)$^-$] (C$_{25}$H$_{39}$N$_6$O$_8$) calculated: 551.2835, found: 551.2824. Elem. analysis: M·1.4TFA·2.4H$_2$O, calculated: C (44.2), H (6.2), N (11.1), F (10.6), found: C (44.3), H (5.8), N (10.8), F (10.4).

According to procedure in Example 93, reaction of starting compound 93a (75 mg, 0.094 mmol), 4-(dimethylamino)pyridine (11.5 mg, 0.094 mmol), 1-hexylamine (47.7 mg, 0.472 mmol) and HATU (53.8 mg, 0.142 mmol) in acetonitrile (1.5 mL) gave analogously 54.5 mg of the product as a white fluffy solid (0.068 mmol, 72% yield relative to 93a).

HRMS (ESI) m/z: [(M−H)$^-$] (C$_{27}$H$_{43}$N$_6$O$_8$) calculated: 579.3148, found: 579.3140. Elem. analysis: M·1.5TFA·3H$_2$O, calculated: C (44.7), H (6.4), N (10.4), F (10.6), found: C (44.9), H (6.0), N (10.0), F (10.3).

Example 95: Preparation of 4-(octylcarbamoyl)-2-((4,7,10-tris(carboxymethyl)-1,4,7,10-tetraazacyclododecan-1-yl)methyl)pyridine 1-oxide (95)

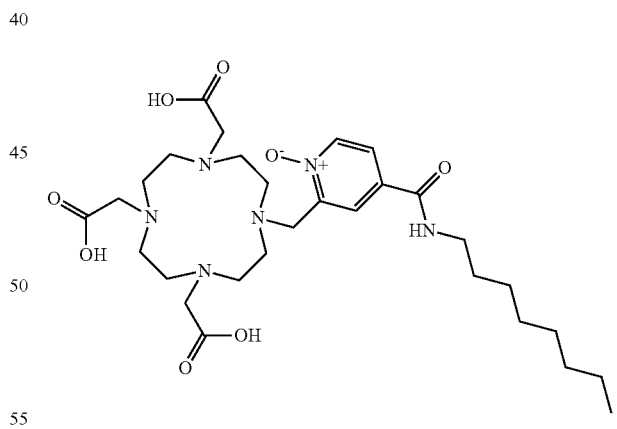

According to procedure in Example 93, reaction of starting compound 93a (75 mg, 0.094 mmol), 4-(dimethylamino)pyridine (11.5 mg, 0.094 mmol), 1-octylamine (61.0 mg, 0.472 mmol) and HATU (53.8 mg, 0.142 mmol) in acetonitrile (1.5 mL) gave analogously 57.5 mg of the product as a white fluffy solid (0.069 mmol, 74% yield relative to 93a).

HRMS (ESI) m/z: [(M+H)$^+$] (C$_{29}$H$_{49}$N$_6$O$_8$) calculated: 609.3606, found: 609.3604. Elem. analysis: M·1.8TFA·0.9H$_2$O, calculated: C (47.2), H (6.3), N (10.1), F (12.4), found: C (47.1), H (6.1), N (9.8), F (12.3).

Example 96: Preparation of 4-(tert-butylcarbamoyl)-2-((4,7,10-tris(carboxymethyl)-1,4,7,10-tetraazacyclododecan-1-yl)methyl)pyridine 1-oxide (96)

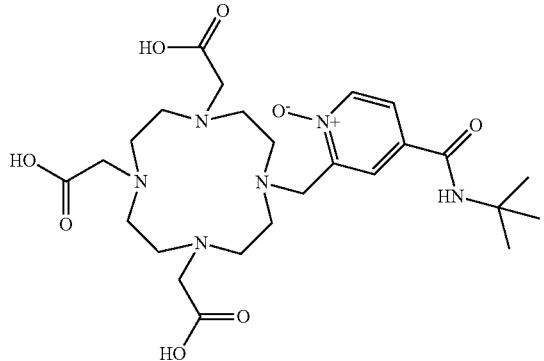 [SMILES: CC(C)(C)NC(=O)c1cc[n+]([O-])c(CN2CCN(CC(=O)O)CCN(CC(=O)O)CCN(CC(=O)O)CC2)c1]

According to procedure in Example 93, reaction of starting compound 93a (75 mg, 0.094 mmol), 4-(dimethylamino)pyridine (11.5 mg, 0.094 mmol), tert.-butylamine (34.5 mg, 0.472 mmol) and HATU (53.8 mg, 0.142 mmol) in acetonitrile (1.5 mL) gave analogously 62 mg of the product as a white fluffy solid (0.076 mmol, 81% yield relative to 93a).

$^1$H NMR (d$_6$-DMSO, 95° C., 500 MHz): $\delta_H$ 1.42 ((CH$_3$)$_3$C—, s, 9H); 3.07-3.14 (cycle, m, 8H); 3.14-3.21 (cycle, m, 8H); 3.60 (CH$_2$—COOH, s, 4H); 3.80 (CH$_2$—COOH, s, 2H); 4.33 (CH$_2$-arom., s, 2H); 7.79-7.83 (CO—NH, m, 1H); 7.91-7.92 (arom., m, 1H); 8.07-8.08 (arom., m, 1H); 8.32-8.33 (arom., m, 1H). $^{13}$C{$^1$H} NMR (d$_6$-DMSO, 95° C., 125 MHz): $\delta_C$ 29.1 ((CH$_3$)$_3$C—, s); 50.9 (cycle, s); 51.0 (2× cycle, s); 51.1 (cycle, s); 52.0 ((CH$_3$)$_3$C—, s); 53.7 (CH$_2$-arom.+CH$_2$—COOH, s); 55.2 (CH$_2$—COOH, s); 125.3 (arom., s); 127.8 (arom., s); 133.0 (arom., s); 139.9 (arom., s); 144.1 (arom., s); 163.1 (CO); 170.5 (CO); 171.1 (CO). HRMS (ESI) m/z: [(M–H)$^-$] (C$_{25}$H$_{39}$N$_6$O$_8$) calculated: 551.2835, found: 551.2827. Elem. analysis: M·1.8TFA·3H$_2$O, calculated: C (42.3), H (5.9), N (10.3), F (12.6), found: C (42.5), H (5.5), N (9.9), F (12.3).

Example 97: Preparation of 4-(benzylcarbamoyl)-2-((4,7,10-tris(carboxymethyl)-1,4,7,10-tetraazacyclododecan-1-yl)methyl)pyridine 1-oxide (97)

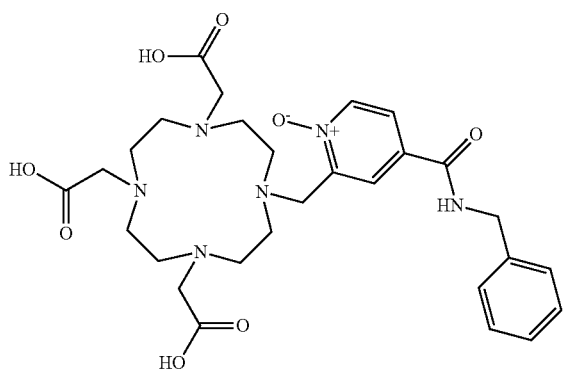 [SMILES: O=C(O)CN1CCN(CC(=O)O)CCN(Cc2cc(C(=O)NCc3ccccc3)cc[n+]2[O-])CCN(CC(=O)O)CC1]

According to procedure in Example 93, reaction of starting compound 93a (100 mg, 0.126 mmol), 4-(dimethylamino)pyridine (15.4 mg, 0.126 mmol), benzylamine (67.4 mg, 0.472 mmol) and HATU (71.7 mg, 0.189 mmol) in acetonitrile (1.5 mL) gave analogously 72.4 mg of the product as a white fluffy solid (0.089 mmol, 70% yield relative to 93a).

$^1$H NMR (d$_6$-DMSO, 95° C., 500 MHz): $\delta_H$ 3.04-3.09 (cycle, m, 4H); 3.09-3.15 (cycle, m, 8H); 3.15-3.21 (cycle, m, 4H); 3.62 (CH$_2$—COOH, s, 4H); 3.75 (CH$_2$—COOH, s, 2H); 4.29 (CH$_2$-arom., s, 2H); 4.52 (NH—CH$_2$-arom., d, $^3$J$_{HH}$=5.7 Hz, 2H); 7.23-7.38 (arom., m, 5H); 7.93-7.97 (arom., m, 1H); 8.13-8.14 (arom., m, 1H); 8.36-8.38 (arom., m, 1H); 9.07-9.14 (CO—NH, m, 1H). $^{13}$C{$^1$H} NMR (d$_6$-DMSO, 95° C., 125 MHz): $\delta_C$ 43.7 (NH—CH$_2$-arom., s); 50.9 (cycle, s); 51.0 (cycle, s); 51.2 (cycle, s); 51.3 (cycle, s); 53.7 (CH$_2$-arom., s); 53.9 (CH$_2$—COOH, s); 55.2 (CH$_2$—COOH, s); 125.0 (arom., s); 127.4 (arom., s); 127.6 (arom., s); 128.0 (arom., s); 128.8 (arom., s); 131.4 (arom., s); 139.5 (arom., s); 140.2 (arom., s); 144.8 (arom., s); 163.6 (CO); 170.8 (CO); 171.0 (CO). HRMS (ESI) m/z: [(M–H)$^-$] (C$_{28}$H$_{37}$N$_6$O$_8$) calculated: 585.2678, found: 585.2669. Elem. analysis: M·1.6TFA·2.7H$_2$O, calculated: C (45.8), H (5.6), N (10.3), F (11.2), found: C (46.0), H (5.2), N (9.9), F (10.9).

Example 98: Preparation of 4-(butoxycarbonyl)-2-((4,7,10-tris(carboxymethyl)-1,4,7,10-tetraazacyclododecan-1-yl)methyl)pyridine 1-oxide (98)

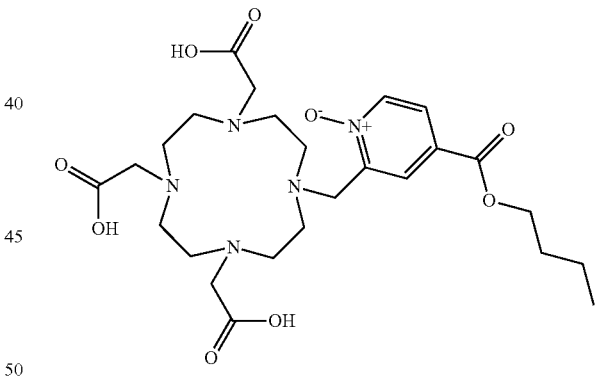

According to procedure in Example 93, reaction of starting compound 93 (75 mg, 0.094 mmol), 4-(dimethylamino)pyridine (11.5 mg, 0.094 mmol), 1-butanol (175 mg, 2.36 mmol) and HATU (53.8 mg, 0.142 mmol) in acetonitrile (1.5 mL) gave analogously 59.1 mg of the product as a white fluffy solid (0.076 mmol, 81% yield relative to 93a).

HRMS (ESI) m/z: [(M+H)$^+$] (C$_{25}$H$_{40}$N$_5$O$_9$) calculated: 554.2821, found: 554.2818.

Elem. analysis: M·1.9TFA·0.5H$_2$O, calculated: C (44.4), H (5.4), N (9.0), F (13.9), found: C (44.3), H (5.3), N (8.8), F (14.0).

Example 99. Preparation of 4-((hexyloxy)carbonyl)-2-((4,7,10-tris(carboxymethyl)-1,4,7,10-tetraazacyclododecan-1-yl)methyl)pyridine 1-oxide (99)

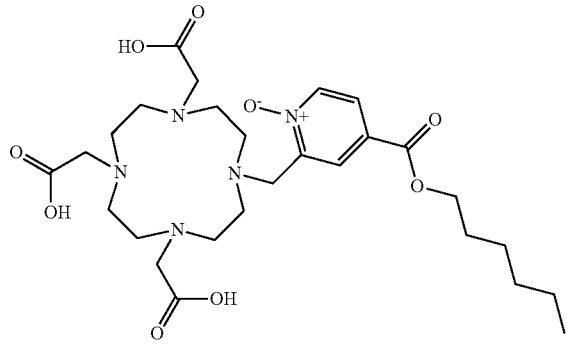 [SMILES: CCCCCCOC(=O)c1cc[n+]([O-])c(CN2CCN(CC(=O)O)CCN(CC(=O)O)CCN(CC(=O)O)CC2)c1]

According to procedure in Example 93, reaction of starting compound 93a (75 mg, 0.094 mmol), 4-(dimethylamino)pyridine (11.5 mg, 0.094 mmol), 1-hexanol (241 mg, 2.36 mmol) and HATU (53.8 mg, 0.142 mmol) in acetonitrile (1.5 mL) gave analogously 54.5 mg of the product as a white fluffy solid (0.069 mmol, 73% yield relative to 93a).

HRMS (ESI) m/z: [(M+H)$^+$] ($C_{27}H_{44}N_5O_9$) calculated: 582.3134, found: 582.3134.

Elem. analysis: M·1.7TFA·0.9H$_2$O, calculated: C (46.1), H (5.9), N (8.9), F (12.2), found: C (46.1), H (5.8), N (8.7), F (12.1).

Example 100: Preparation of 4-((octyloxy)carbonyl)-2-((4,7,10-tris(carboxymethyl)-1,4,7,10-tetraazacyclododecan-1-yl)methyl)pyridine 1-oxide (100)

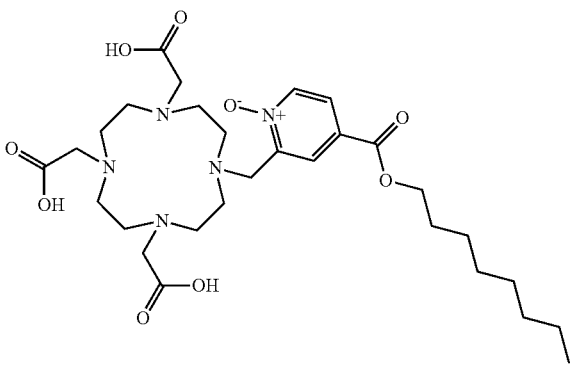 [SMILES: CCCCCCCCOC(=O)c1cc[n+]([O-])c(CN2CCN(CC(=O)O)CCN(CC(=O)O)CCN(CC(=O)O)CC2)c1]

According to procedure in Example 93, reaction of starting compound 93a (75 mg, 0.094 mmol), 4-(dimethylamino)pyridine (11.5 mg, 0.094 mmol), 1-octanol (307 mg, 2.36 mmol) and HATU (53.8 mg, 0.142 mmol) in acetonitrile (1.5 mL) gave analogously 46.8 mg of the product as a white fluffy solid (0.057 mmol, 61% yield relative to 93a).

HRMS (ESI) m/z: [(M+H)$^+$] ($C_{29}H_{48}N_5O_9$) calculated: 610.3447, found: 610.3448.

Elem. analysis: M·1.7TFA·0.9H$_2$O, calculated: C (47.5), H (6.2), N (8.5), F (11.8), found: C (47.6), H (6.1), N (8.4), F (11.5).

Example 101: Preparation of 4-((benzyloxy)carbonyl)-2-((4,7,10-tris(carboxymethyl)-1,4,7,10-tetraazacyclododecan-1-yl)methyl)pyridine 1-oxide (101)

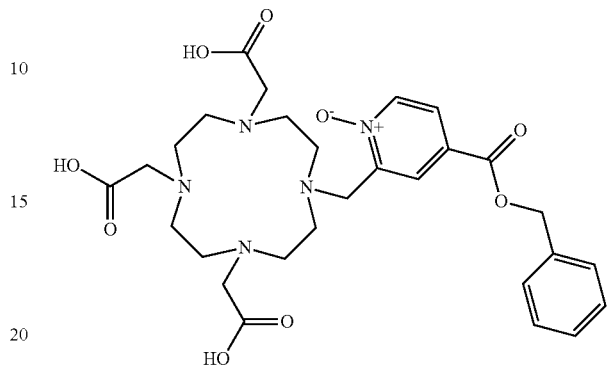

According to procedure in Example 93, reaction of starting compound 93a (75 mg, 0.094 mmol), 4-(dimethylamino)pyridine (11.5 mg, 0.094 mmol), benzyl alcohol (255 mg, 2.36 mmol) and HATU (53.8 mg, 0.142 mmol) in acetonitrile (1.5 mL) gave analogously 55.1 mg of the product as a white fluffy solid (0.069 mmol, 73% yield relative to 93a).

HRMS (ESI) m/z: [(M−H)$^-$] ($C_{28}H_{36}N_5O_9$) calculated: 586.2519, found: 586.2508. Elem. analysis: M·1.5TFA·2.3H$_2$O, calculated: C (46.5), H (5.4), N (8.8), F (10.7), found: C (46.7), H (5.0), N (8.6), F (10.4).

Example 102: Preparation of 4-(isopropoxycarbonyl)-2-((4,7,10-tris(carboxymethyl)-1,4,7,10-tetraazacyclododecan-1-yl)methyl)pyridine 1-oxide (102)

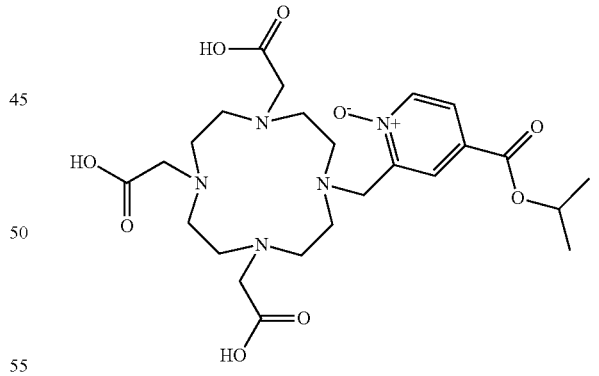

According to procedure in Example 93, reaction of starting compound 93a (75 mg, 0.094 mmol), 4-(dimethylamino)pyridine (11.5 mg, 0.094 mmol), a isopropanol (142 mg, 2.36 mmol) and HATU (53.8 mg, 0.142 mmol) in acetonitrile (1.5 mL) gave analogously 17.5 mg of the product as a white fluffy solid (0.022 mmol, 24% yield relative to 93a).

HRMS (ESI) m/z: [(M+H)$^+$] ($C_{24}H_{38}N_5O_9$) calculated: 540.2664, found: 540.2663.

Elem. analysis: M·1.8TFA·1.9H$_2$O, calculated: C (42.5), H (5.5), N (9.0), F (13.2), found: C (42.5), H (5.1), N (8.7), F (13.2).

Example 103: Preparation of methyl 6-(chloromethyl)nicotinate hydrochloride (103a)

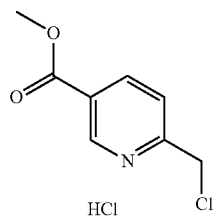

Methyl 6-(hydroxymethyl)nicotinate (3.33 g, 20 mmol) was added slowly in small portions to a stirred thionyl chloride (16.4 g) cooled to 0° C. The solution was then let warm up to room temperature. After 1 hour, the thionyl chloride was evaporated on rotary evaporator. The residue spontaneously crystallized and was recrystallized from concentrated chloroform solution to give product as white crystals (3.88 g, 17.5 mmol, 87% yield).

MS (ESI) m/z: [(M+H)$^+$] ($C_8H_9ClNO_2$) calculated: 186.0, found: 186.1.

Preparation of 2-(chloromethyl)-5-(methoxycarbonyl)pyridine 1-oxide (103b)

Starting compound 103a (650 mg, 2.93 mmol) was dissolved in chloroform (65 mL) and cooled in water/ice bath. Then, m-chloroperoxobenzoic acid (77%, 1.54 g, 6.87 mmol) was added and the reaction mixture was stirred for 24 hours while letting to warm up to room temperature. The solvent was evaporated on rotary evaporator and the residue was purified by flash chromatography on silica with gradient 0-20% methanol in dichloromethane, giving 366 mg of the product as white solid (1.82 mmol, 62% yield).

MS (ESI) m/z: [(M+H)$^+$] ($C_8H_9ClNO_3$) calculated: 202.0, found: 202.1.

Preparation of 5-carboxy-2-((4,7,10-tris(2-(tert-butoxy)-2-oxoethyl)-1,4,7,10-tetraazacyclododecan-1-yl)methyl)pyridine 1-oxide salt with N,N-diisopropylethylamine (103c)

Starting compound B (953 mg, 1.60 mmol), starting compound 103b (355 mg, 1.76 mmol), anhydrous potassium carbonate (457 mg, 3.31 mmol) and acetonitrile (20 mL) were mixed and stirred under argon for 24 hours at room temperature. The solids were filtered off and the filtrate was diluted with water (20 mL). Then, LiOH·H$_2$O (148 mg, 3.52 mmol) was added and the mixture was stirred at room temperature. After 60 minutes the reaction was complete (followed by LC-MS) and the methyl ester group was hydrolyzed. The reaction mixture was acidified with trifluoroacetic acid (0.306 mL, 4.00 mmol) and evaporated on rotary evaporator. The residue was purified on flash chromatography (C18 column, acetonitrile/water gradient with 0.2% N,N-diisopropylethylamine). Fractions containing pure intermediate with free carboxylate on pyridine were pooled and evaporated. The residue was dissolved in 50/50 methanol/water mixture and passed slowly through column of Dowex 50 saturated with N,N-diisopropylethylamine. The product was eluted with methanol/water (50/50) mixture. Collected eluate was evaporated, dried in high vacuum and lyophilized from benzene/acetonitrile (50/50) mixture to give product as pale yellow solid foam (929 mg, 1.17 mmol, 73% relative to B).

$^1$H NMR (CD$_3$OD, 25° C., 500 MHz): $\delta_H$ 1.36-1.42 (DIPEA 5×CH$_3$, m, 15H); 1.53 ((CH$_3$)$_3$C—, s, 18H); 1.62 ((CH$_3$)$_3$C—, s, 9H); 3.09-3.86 (2×CH$_2$CO+8× cycle CH$_2$, m, 20H); 3.25 (DIPEA CH$_2$CH$_3$, q, $^3J_{HH}$=7.3, 2H); 3.75 (DIPEA CH(CH$_3$)$_2$, hept, $^3J_{HH}$=7.5, 2H); 3.75 (CH$_2$CO, bs, 4H); 4.09 (CH$_2$CO, bs, 2H); 4.77 (CH$_2$-arom., bs, 2H); 7.88-7.93 (arom., m, 1H); 8.09-8.17 (arom., m, 1H); 8.82-8.87 (arom., m, 1H). $^{13}$C{$^1$H} NMR (CD$_3$OD, 25° C., 125 MHz): $\delta_C$ 15.9 (DIPEA CH$_3$, s); 17.3 (DIPEA CH$_3$, s); 27.1 ((CH$_3$)$_3$C—, s); 27.2 ((CH$_3$)$_3$C—, s); 42.4 (DIPEA CH$_2$CH$_3$, s); 49.1 (2× cycle, bs); 50.2 (2× cycle, bs); 53.2 (CH$_2$-arom., bs); 54.4 (DIPEA CH(CH$_3$)$_2$, s); 54.4 (CH$_2$CO, bs); 54.8 (CH$_2$CO, bs); 82.9 ((CH$_3$)$_3$C—, s); 84.2 ((CH$_3$)$_3$C—, s); 129.0 (2× arom., s); 131.5 (arom., s); 140.3 (arom., s); 163.4 (CO, s); 169.6 (CO, s); 169.7 (CO, s). HRMS (ESI) m/z: [(M+H)$^+$] ($C_{33}H_{56}N_5O_9$) calculated: 666.4073, found: 666.4075.

Preparation of 5-(butylcarbamoyl)-2-((4,7,10-tris(carboxymethyl)-1,4,7,10-tetraazacyclododecan-1-yl)methyl)pyridine 1-oxide (103)

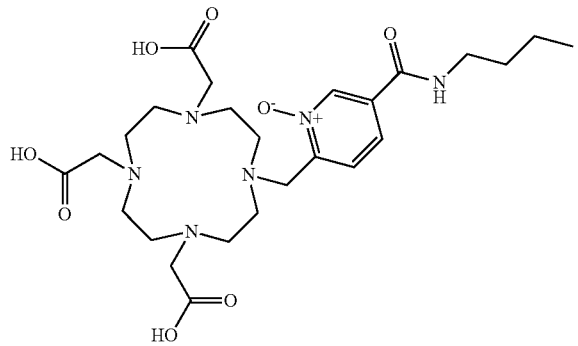 [SMILES: CCCCNC(=O)c1ccc(CN2CCN(CC(=O)O)CCN(CC(=O)O)CCN(CC(=O)O)CC2)[n+]([O-])c1]

According to procedure in Example 93, reaction of starting compound 103c (75 mg, 0.094 mmol), 4-(dimethylamino)pyridine (11.5 mg, 0.094 mmol), 1-butylamine (34.5 mg, 0.472 mmol) and HATU (53.8 mg, 0.142 mmol) in acetonitrile (1.5 mL) gave analogously 26.7 mg of the product as a white fluffy solid (0.034 mmol, 37% yield relative to 103c).

$^1$H NMR (D$_2$O, 95° C., 500 MHz): $\delta_H$ 1.47 (CH$_3$, t, $^3J_{HH}$=7.4 Hz, 3H); 1.90-1.97 (CH$_2$-aliph., m, 2H); 2.12-3.18 (CH$_2$-aliph., m, 2H); 3.80-3.85 (cycle, m, 4H); 3.85-3.92 (cycle, m, 8H); 3.92-4.00 (cycle+CH$_2$-aliph., m, 6H); 4.24 (CH$_2$—COOH, s, 4H); 4.43 (CH$_2$—COOH, s, 2H); 5.06 (CH$_2$-arom., s, 2H); 8.42-8.43 (arom., m, 1H); 8.47-8.49 (arom., m, 1H); 9.22-9.23 (arom., m, 1H). $^{13}$C{$^1$H} NMR (D$_2$O, 95° C., 125 MHz): $\delta_C$ 13.6 (CH$_3$, s); 20.16 (CH$_2$-aliph., s); 31.1 (CH$_2$-aliph., s); 40.8 (CH$_2$—NH—CO, s); 50.6 (3× cycle, s); 51.1 (cycle, s); 53.4 (CH$_2$-arom., s); 54.7 (CH$_2$—COOH, s); 55.5 (CH$_2$—COOH, s); 129.4 (arom., s); 129.9 (arom., s); 135.5 (arom., s); 139.8 (arom., s); 146.0 (arom., s); 165.5 (CO); 171.7 (CO); 171.9 (CO). HRMS (ESI) m/z: [(M+H)$^+$] ($C_{25}H_{41}N_6O_8$) calculated: 553.2980, found: 553.2978. Elem. analysis: M·1.6TFA·2.4H$_2$O, calculated: C (43.5), H (6.0), N (10.8), F (11.7), found: C (43.6), H (5.6), N (10.4), F (11.6).

Example 104: Preparation of 5-((benzyloxy)carbo-nyl)-2-((4,7,10-tris(carboxymethyl)-1,4,7,10-tet-raazacyclododecan-1-yl)methyl)pyridine 1-oxide (104)

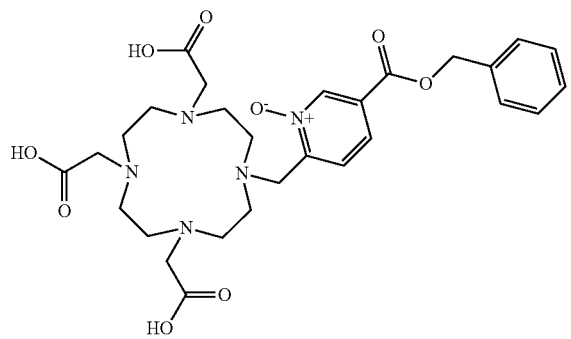 [SMILES: O=C(O)CN1CCN(CC(=O)O)CCN(Cc2ccc(C(=O)OCc3ccccc3)c[n+]2[O-])CCN(CC(=O)O)CC1]

According to procedure in Example 93, reaction of starting compound 103c (75 mg, 0.094 mmol), 4-(dimethylamino)pyridine (11.5 mg, 0.094 mmol), benzyl alcohol (255 mg, 0.472 mmol) and HATU (53.8 mg, 0.142 mmol) in acetonitrile (1.5 mL) gave analogously 16.7 mg of the product as a white fluffy solid (0.020 mmol, 21% yield relative to 103c).

HRMS (ESI) m/z: [(M+H)$^+$] ($C_{28}H_{38}N_5O_9$) calculated: 588.2664, found: 588.2666.

Elem. analysis: M·1.8TFA·1.9H$_2$O, calculated: C (45.9), H (5.2), N (8.5), F (12.4), found: C (46.0), H (5.0), N (8.3), F (12.2).

II Separation of s-, p- and d-Block Metals

The chelator molecules described in this invention were tested for their ability to separate s-, p- and d-block metals by first forming chelates with a chelator that provides chromatographic selectivity towards the metals and then subjecting the chelates to conventional chromatographic separation.

Example 105: Variability in Retention of Metal Chelates on Reversed-Phase HPLC Usable for Separation Complexation of selected s-, p- and d-block metals ($Ca^{2+}$, $Fe^{2+}$, $Fe^{3+}$, $Co^{2+}$, $Ni^{2+}$, $Cu^{2+}$, $Zn^{2+}$, $Al^{3+}$, $Pb^{2+}$) were carried out in parallel as follows. Distilled water (815 µL), approximately 0.01 M aqueous solution of the chelator 2,2',2''-(10-((6-chloropyridin-2-yl)methyl)-1,4,7,10-tetraazacyclododecane-1,4,7-triyl)triacetic acid (prepared in Example 2), or 1-((4,7,10-tris(carboxymethyl)-1,4,7,10-tetraazacyclododecan-1-yl)methyl)isoquinoline 2-oxide or (prepared in Example 21) (60 µL, approx. 0.6 µmol) and approximately 0.005 M aqueous solution of a metal salt of a composition given in Table 1 (100 µL, approx. 0.5 µmol) were mixed in a 2 mL plastic Eppendorf vial equipped with a Teflon-coated magnetic stir bar. The mixture was stirred and 0.1 M aqueous sodium hydroxide (25 µL, 2.5 µmol) was added. The reaction mixture was stirred at room temperature for 2 hours, centrifugated and transferred into a glass HPLC. HPLC analysis was performed by injecting 2 µL, using column Phenomenex Luna C18(2) (150×4.6 mm, 5 µm), a mobile phase consisting of 10% acetonitrile in water with 0.02% TFA at a flow rate of 1 mL/min, and detection by UV absorbance at 280 nm. Retention times for respective metal chelates are summarized in Table 1. For a given chelator, differing retention times of different metals signify that such metals can be chromatographically separated in the form of chelates with that chelator. The results in Table 1 demonstrate that various combinations of metals from the s-, p- and d-block can be separated according to the present invention.

TABLE 1

| | | Compound (chelator) | |
| --- | --- | --- | --- |
| | | 2 | 21 |
| Metal ion | Metal compound | Retention time (minutes) | |
| $Ca^{2+}$ | $Ca(NO_3)_2$ | (2.22) * | (2.58) * |
| $Fe^{2+}$ | $Fe(NH_4)_2(SO_4)_2$ | 5.18 | 6.41 |
| $Fe^{3+}$ | $Fe(NO_3)_3$ | 5.15 | 6.42 |
| $Co^{2+}$ | $Co(NO_3)_2$ | 11.00 | 5.97 |
| $Ni^{2+}$ | $Ni(NO_3)_2$ | 7.66 | 4.67 |
| $Cu^{2+}$ | $CuCl_2$ | 7.58 | 5.30 |
| $Zn^{2+}$ | $Zn(NO_3)_2$ | 8.08 | 5.79 |
| $Al^{3+}$ | $Al(NO_3)_3$ | (2.21) * | (2.58) * |
| $Pb^{2+}$ | $Pb(NO_3)_2$ | 4.14 | 8.10 |

* Metal chelate unstable under the conditions, only free chelator detected (value in parentheses).

III Separation of Rare Earth Elements

The chelator molecules described in this invention were tested for their ability to separate rare earth elements by first forming chelates with a chelator that provides chromatographic selectivity towards rare earth elements and then subjecting the chelates to conventional chromatographic separation.

Example 106: Separation of No-Carrier-Added $^{177}$Lu from a Natural Yb Target on Reversed-Phase HPLC The present invention was tested on a separation of trace amounts of clinically relevant radionuclide $^{177}$Lu from a bulk amount of neutron-irradiated ytterbium target. The target made of YbCl$_3$ contained 1.756 mg of [nat]Yb (natural isotope composition, 99.999% metal purity) and provided a mixture of three radionuclides after irradiation: [177]Lu, [175]Yb and [169]Yb. Because of the presence of radionuclides [175]Yb and [169]Yb, the efficiency of Lu/Yb separation could be quantitatively assessed by measuring gamma emissions specific for each radionuclide in a calibrated gamma spectrometer.

Figure 2:
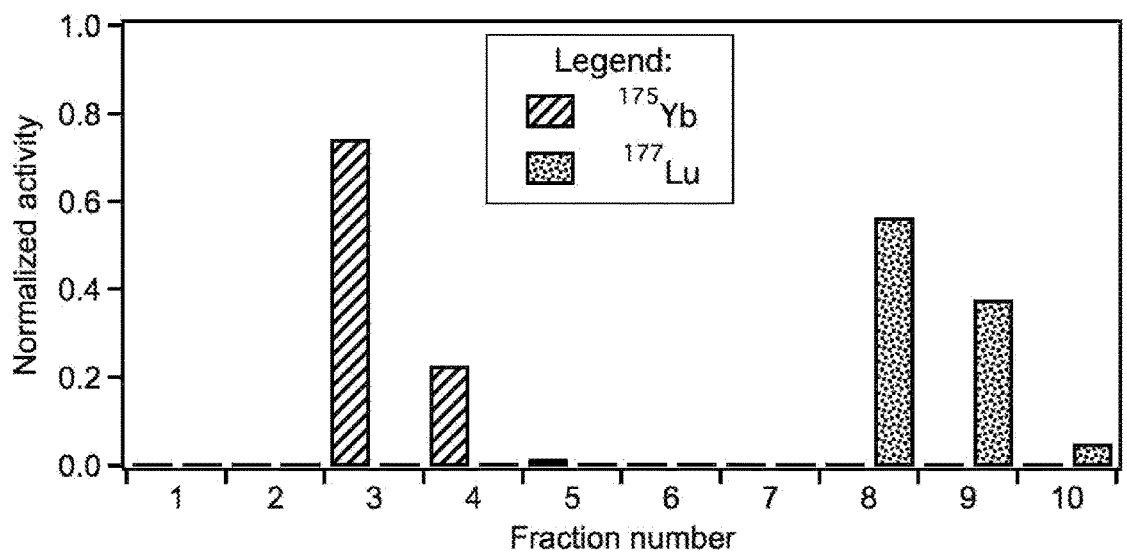
FIG. 2: A graph showing the content of $^{177}$Lu from $^{175}$Yb radionuclides in collected chromatographic fractions after a chromatographic separation using a reversed-phase C18 column and elution with methanol/water mobile phase as described in Example 93 in accordance with the present invention.

The target was dissolved in 0.5 M hydrochloric acid to a volume of 555 µL. An aliquot of 50 µL (0.9 mol of Yb+Lu) was pipetted into a 2 mL plastic Eppendorf vial. Then, 18.5 µL of 0.1 M stock solution (1.85 µmol) of the chelator 2,2',2''-(10-((6-chloropyridin-2-yl)methyl)-1,4,7,10-tetraazacyclododecane-1,4,7-triyl)triacetic acid (prepared in Example 2) in distilled water was added, followed by 28.7 µL of 1 M sodium hydroxide (28.7 µmol) in distilled water. The reaction was gently shaken in closed vial for 1 hour at 40° C. The reaction mixture was then subjected to chromatographic separation on an HPLC system equipped with a reversed-phase column (Supelco Discovery C18, 250×10 mm, 5 µm), a diode-array detector (DAD), gamma detector and automated fraction collector. The whole reaction mixture volume was injected at once. The chromatography was performed with 4.5 mL/minute flowrate and isocratic elution (14% methanol, 86% deionized water). Fractions of 0.9 mL were collected starting at 6.0 minutes. FIG. 1 shows UV absorbance at 280 nm and gamma detection chromatographic traces of this separation. The positions of collected fractions are marked in the lower panel of FIG. 1. Two important facts are apparent from FIG. 1. Firstly, the UV absorbance trace demonstrates that the Yb chelate is present in macroscopic (bulk) quantity, while the trace amount of Lu chelate is below the detection limit of the UV detector. Secondly, the gamma detection that is sensitive to both elements clearly shows separation of the trace amount of Lu chelate from the bulk Yb chelate. The composition of fractions collected during the chromatography is summarized in a graph in FIG. 2. Majority of $^{177}$Lu (94%) was collected in only two fractions (No. 8 and 9) with total volume of 1.8 mL. The content of ytterbium in these fractions was reduced to 0.19% of the original amount. This represents 500-fold reduction in the amount of carrier material achieved with a single chromatography under 9 minutes. The total amount of $^{177}$Lu recovered during the chromatography was 81%. Overall, this example demonstrates utility of the invention for fast and efficient separation of no-carrier-added $^{177}$Lu radionuclide.

Example 107: Separation of Er, Tm and Yb from Mutual Mixtures on Silica TLC

Figure 3:
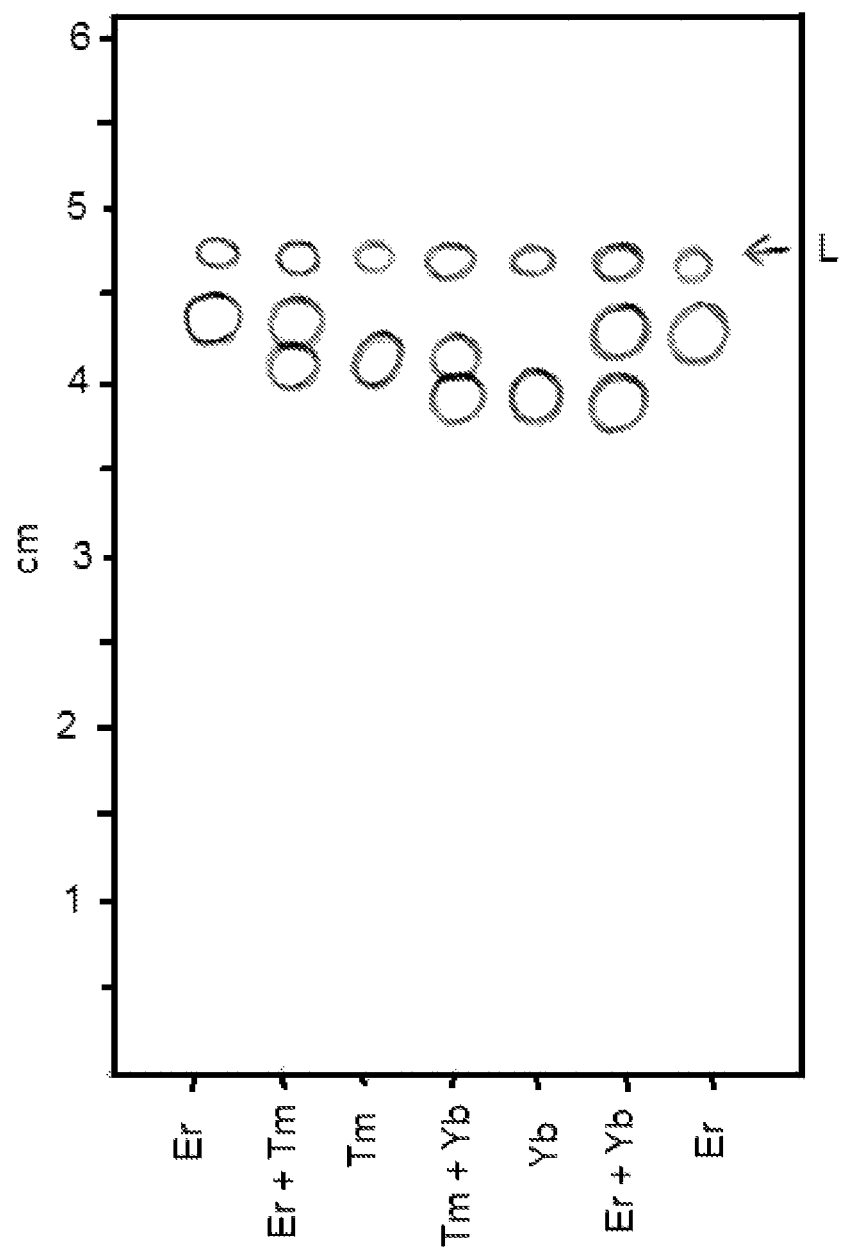
FIG. 3: A scan of a silica TLC plate showing separation of erbium (Er), thulium (Tm) and ytterbium (Yb) chelates as described in Example 94. "L" stands for excessive ligand (chelator).

Complexation of three rare earth elements (erbium, thulium and ytterbium) were carried out in parallel as follows. Distilled water (450 µL), approximately 0.1 M aqueous solution of the chelator 1-((4,7,10-tris(carboxymethyl)-1,4,7,10-tetraazacyclododecan-1-yl)methyl)isoquinoline 2-oxide (prepared in Example 21) (25 µL, approx. 2.5 µmol) and approximately 0.1 M aqueous solution of a rare earth trichloride (ErCl$_3$, TmCl$_3$ or YbCl$_3$; 25 µL, approx. 2.5 µmol) were pipetted into a 2 mL plastic Eppendorf vial equipped with a Teflon-coated magnetic stir bar. The mixture was stirred and 2 M aqueous sodium hydroxide (6.25 µL, 12.5 µmol) was added. The reaction mixture was stirred at room temperature for 24 hours. The resulting solutions of chelates (0.5 µL, 2.5 nmol) were spotted onto a silica TLC sheet (Merck, TLC Silica gel 60 F$_{254}$) as individual spots, and overlayed in pairs in order to simulate 1:1 mixtures of the rare earth elements. The TLC was developed using isopropanol/water/25% ammonium hydroxide (7/3/3 ratio) mobile phase. The spots were visualized under UV lamp (254 nm) as dark spots on green fluorescent background and marked with pencil. The TLC plate shown on FIG. 3 clearly demonstrates that mixtures of rare earth elements can be separated by this method. A small excess of the chelator was also separated from the chelates. The retention factors were: free chelator ($R_f$=0.78), Er chelate ($R_f$=0.71), Tm chelate ($R_f$=0.67), Yb chelate ($R_f$=0.64).

Example 108: Variability in Retention of Metal Chelates on Reversed-Phase HPLC Usable for Separation Solutions of metal chelates were prepared according to the procedure in Example 94 with the exception that, when necessitated by solubility of the chelator, 50% acetonitrile in water was used as a solvent. Then 100 µL of the solution was pipetted into a glass HPLC vial and diluted with distilled water or 50% acetonitrile in water (900 µL). The individual solutions were subjected to HPLC chromatography by injecting 2 µL, using column Phenomenex Luna Phenyl-Hexyl (150×4.6 mm, 5 m), a mobile phase specified in Table 1 at a flow rate of 1 mL/min, and detection by UV absorbance at 220, 254 or 280 nm. Retention times for respective metal chelates are summarized in Table 2. For a given chelator, differing retention times of different metals signify that such metals can be chromatographically separated in the form of chelates with that chelator. The results in Table 2 demonstrate that various combinations of metals from the rare earth element group can be separated according to the present invention.

TABLE 2

| | Compound (chelator) | | | | | | | | | | |
|---|---|---|---|---|---|---|---|---|---|---|---|
| | 1 | 6 | 8 | 15 | 23 | 28 | 45 | 46 | 49 | 64 | 80 |
| Metal ion | | | | Retention time (minutes) | | | | | | | |
| La$^{3+}$ | | | 6.72 | | | | | | | | 6.14 |
| Ce$^{3+}$ | | | | | | | | 6.47 | | | 5.79 |
| Pr$^{3+}$ | | | | | | | | 6.14 | | | 5.49 |
| Nd$^{3+}$ | | | | | | | | 5.67 | | 6.17 | 5.21 |
| Pm$^{3+}$* | | | | | | | | | | | |
| Sm$^{3+}$ | | | | | | | | 4.73 | | 5.53 | |
| Eu$^{3+}$ | | | | | | | 5.3 | | | 5.04 | |
| Gd$^{3+}$ | | | | | | 5.1 | 5.0 | | 5.34 | | |
| Tb$^{3+}$ | | | | | | 4.5 | 4.7 | | 4.86 | | |
| Dy$^{3+}$ | | | | | 4.2 | 6.08 | | | 4.35 | | |
| Ho$^{3+}$ | | | | | | 5.56 | | | | | |
| Er$^{3+}$ | | | | | 6.9 | 5.10 | | | | | |
| Tm$^{3+}$ | | | | | 6.0 | | | | | | |
| Yb$^{3+}$ | 4.53 | | | | 5.4 | | | | | | |
| Lu$^{3+}$ | 4.71 | | 4.59 | | | | | | | | |
| Y$^{3+}$ | 4.50 | 5.69 | | | | | | | | | |
| Sc$^{3+}$ | 5.89 | 3.85 | | | | | | | | | |
| | Mobile phase composition | | | | | | | | | | |
| % acetonitrile | 4 | 6 | 5 | 5 | 14 | 17 | 18 | 24 | 8 | 16 | 15 |
| Buffer | w | w | w | w | AF | w | w | AF | SA | w | AF |

*Unstable element, values not determined.
w pure water without additives
AF 0.01 mol/L ammonium formate pH = 7.0
SA 0.01 mol/L sodium acetate pH = 4.5

Example 109: Acidic Decomplexation Followed by Removal of the Free Chelator

Figure 4:
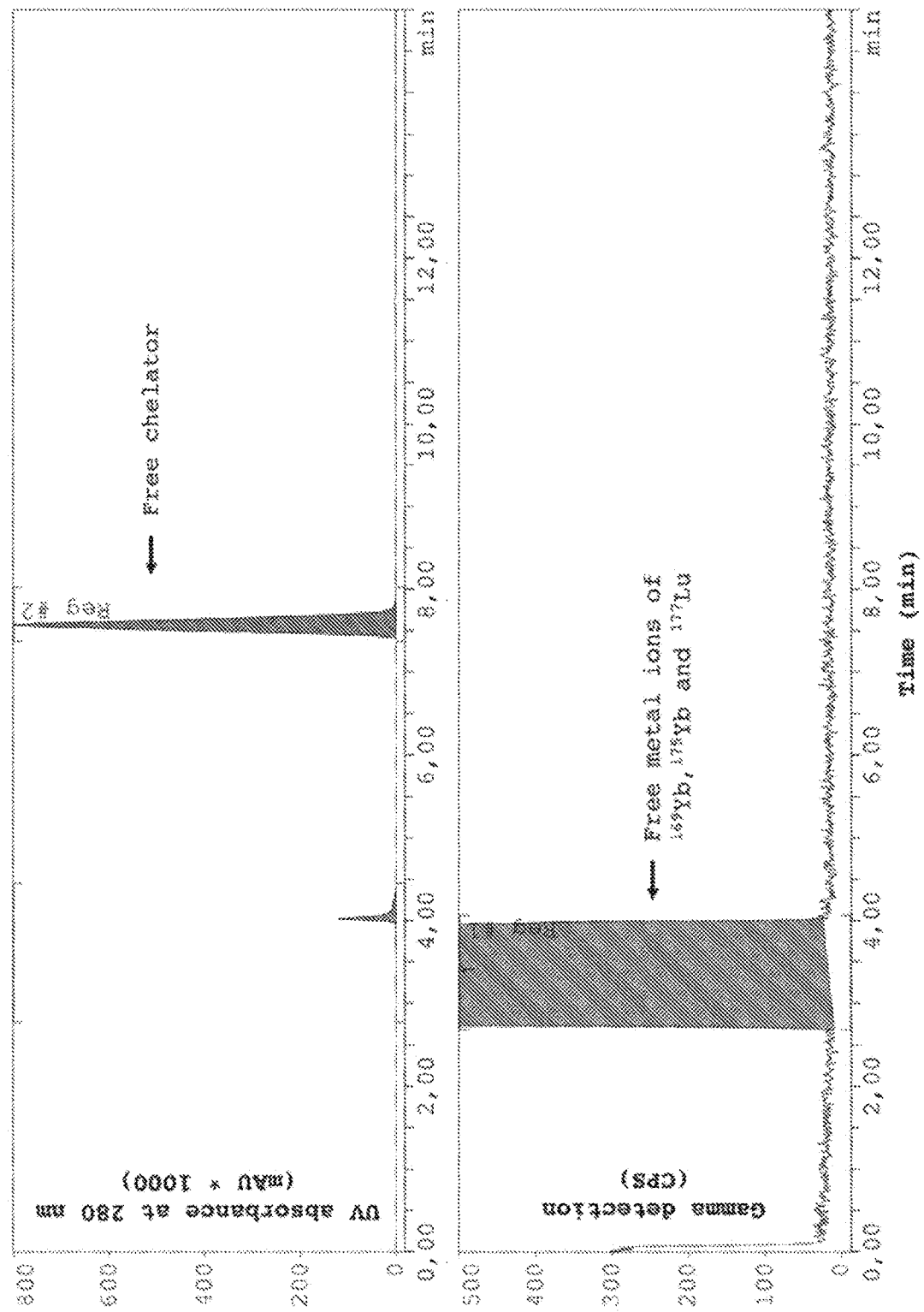
FIG. 4: A chromatogram showing UV absorbance at 280 nm (upper panel) and gamma detection (lower panel) demonstrating acidic decomplexation of a mixture of chelates and separation of the resulting free chelator from the free metal ions as described in Example 96.

Solution containing a mixture of chelates of non-radioactive ytterbium and radionuclides $^{177}$Lu, $^{175}$Yb and $^{169}$Yb with the chelator 2,2',2"-(10-((6-chloropyridin-2-yl)methyl)-1,4,7,10-tetraazacyclododecane-1,4,7-triyl)triacetic acid (prepared in Example 2) was prepared identically according to procedure in Example 93. Then, 20 μL of this solution were mixed with 20 μL of neat trifluoroacetic acid and incubated for 15 minutes at 40° C. The reaction mixture was then subjected to chromatographic separation on an HPLC system equipped with a reversed-phase column (Supelco Discovery C18, 250×10 mm, 5 μm), a diode-array detector (DAD) and gamma detector. The whole reaction mixture volume was injected at once. The chromatography was performed with 4.5 mL/minute flowrate and a linear gradient elution (from 3 to 25% methanol in deionized water containing 0.02% trifluoroacetic acid). FIG. 4 shows UV absorbance at 280 nm and gamma detection chromatographic traces of this separation. It is apparent from the gamma trace that all metal eluted early (peak labeled as "Reg #1") and that there was no corresponding peak in the UV trace. In accordance with this, the major peak observed in the UV trace corresponds to the free chelator (peak labeled as "Reg #2") and there was no corresponding peak in the gamma trace. These results confirm that the metal chelates were successfully decomposed to free metal ions and a free chelator, and that the chelator could be chromatographically removed from the metal ions.

INDUSTRIAL APPLICABILITY

The present invention is considered as susceptible of industrial application in separation and purification of metals, separation and purification of metal radionuclides, concentrating diluted solutions of metal radionuclides by means of solid phase extraction, recovery of isotopically enriched metal material used for production of metal radionuclides, purification of starting metal material prior to its use for production of metal radionuclides, decontamination of surfaces contaminated by metal radionuclides, selective recovery of metals from nuclear waste, selective recovery of metals from products of nuclear fission, hydrometallurgical processing of spent nuclear fuel and other radioactive waste.

The invention claimed is:

1. A method of chromatographically separating rare earth elements and/or s-, p- and d-block metals, the method comprising:
   contacting a compound of general formula (I) with a mixture of two or more metals, where the metals are selected from a rare earth element, an s-block metal, a p-block metal, or a d-block metal to form a separation mixture;
   applying the separation mixture to a chromatographic column;

wherein:

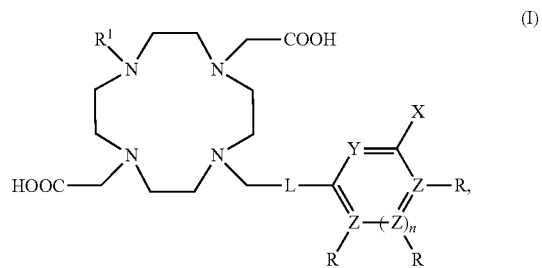

(I)

X is Cl or Br,
Y is nitrogen;
Z atoms are independently selected from the group consisting of carbon and nitrogen, wherein R is only present when the valence of Z allows it; wherein at least one Z is carbon; and wherein n is 0 or 1;
L is a covalent bond or —C(O)—;
each R is independently selected from the group consisting of H; $C_1$ to $C_6$ alkyl; $C_1$ to $C_6$ alkyloxy; $C_6$ to $C_{10}$ aryloxy; benzyloxy; $C_1$ to $C_6$ alkylthio; $C_6$ to $C_{10}$ arylthio; F; Cl; Br; I; OH; SH; $NH_2$; $C_1$ to $C_6$ alkylamino; di($C_1$ to $C_6$ alkyl)amino; $C_1$ to $C_6$ acylamino; di($C_1$ to $C_6$ acyl)amino; $C_6$ to $C_{10}$ arylamino; di($C_6$ to $C_{10}$ aryl)amino; CN; OH; nitro; $COOR_n$; $C(O)NHR_n$; and $C(O)N(R_n)_2$; and wherein $R_n$ is independently H or $C_1$ to $C_{10}$ alkyl or $C_6$ to $C_{10}$ aryl; and
$R^1$ is selected from the group consisting of H; —$C_1$ to $C_6$ alkyl; benzyl, which can be optionally substituted independently with one or more substituents selected from nitro and OH; —($C_1$ to $C_2$ alkylene) COOH, the alkylene of which can optionally be substituted with $C_1$ to $C_6$ alkyl; —$CH_2P(O)(OH)_2$; $CH_2P(O)(OH)(C_1$ to $C_6$ alkyl);

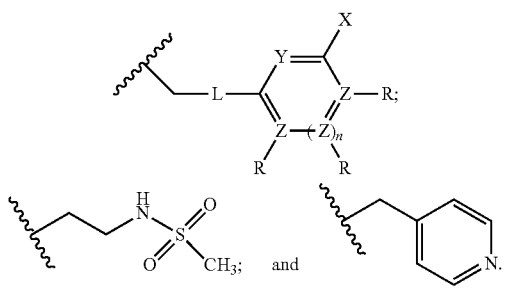

2. The method of claim 1, wherein the mixture of two more metals is a mixture of two or more rare earth elements.

3. The method of claim 1, wherein the mixture of two more metals is a mixture of two or more s-block, p-block, and d-block metals, selected from period table groups II.A, III.A, IV.A, V.A, I.B, II.B, and VIII.

4. The method of claim 1, wherein at most one Z other than carbon is present in each ring of the general formula (I).

5. The method of claim 1, wherein R is selected from the group consisting of H, OH, $OCH_3$, $NO_2$, F, Cl, Br, I, $CH_3$, COOH, $COOR_n$, $C(O)NHR_n$, and $C(O)N(R_n)_2$, and $R_n$ is independently H or $C_1$ to $C_{10}$ alkyl or $C_6$ to $C_{10}$ aryl.

6. The method of claim 1, wherein the compound of general formula (I) is 2,2',2"-(10-((6-chloropyridin-2-yl)

methyl)-1,4,7,10-tetraazacyclododecane-1,4,7-triyl)triacetic acid; 2,2',2''-(10-((6-bromopyridin-2-yl)methyl)-1,4,7,10-tetraazacyclododecane-1,4,7-triyl)triacetic acid; 2,2'-(4-((6-bromopyridin-2-yl)methyl)-10-(2-carboxyethyl)-1,4,7,10-tetraazacyclododecane-1,7-diyl)diacetic acid; 2,2'-(4-(2-carboxyethyl)-10-((6-chloropyridin-2-yl)methyl)-1,4,7,10-tetraazacyclododecane-1,7-diyl)diacetic acid; 2,2'-(4-((6-carboxypyridin-2-yl)methyl)-10-((6-chloropyridin-2-yl)methyl)-1,4,7,10-tetraazacyclododecane-1,7-diyl)diacetic acid; 2,2'-(4-((6-bromopyridin-2-yl)methyl)-10-((6-carboxypyridin-2-yl)methyl)-1,4,7,10 tetraazacyclododecane-1,7-diyl)diacetic acid; 2,2'-(4-((6-chloropyridin-2-yl)methyl)-10-(phosphonomethyl)-1,4,7,10-tetraazacyclododecane-1,7-diyl)diacetic acid; 2,2'-(4-((6-bromopyridin-2-yl)methyl)-10-((hydroxy(methyl)phosphoryl)methyl)-1,4,7,10-tetraazacyclododecane-1,7-diyl)diacetic acid; 2,2'-(4-((6-chloropyridin-2-yl)methyl)-10-((hydroxy(methyl)phosphoryl)methyl)-1,4,7,10-tetraazacyclododecane-1,7-diyl)diacetic acid; 2,2'-(4-(1-carboxyethyl)-10-((6-chloropyridin-2-yl)methyl)-1,4,7,10-tetraazacyclododecane-1,7-diyl)diacetic acid; or 2,2'-(4-((6-chloropyridin-2-yl)methyl)-10-(2-(methylsulfonamido)ethyl)-1,4,7,10-tetraazacyclododecane-1,7-diyl)diacetic acid.

7. A method of chromatographic separation of rare earth elements and/or s-, p- and d-block metals selected from groups II.A, III.A, IV.A, V.A, I.B, II.B, and VIII.B metals, from a mixture of at least two metal ions, at least one of them being a metal selected from Ce, Dy, Er, Eu, Gd, Ho, La, Lu, Nd, Pr, Pm, Sm, Sc, Tb, Tm, Yb, Y, alkaline earth metals, Al, Ga, In, Tl, Sn, Pb, Bi and transitional metals, the method comprising:
providing a mixture of at least one metal ion selected from the group consisting of Ce, Dy, Er, Eu, Gd, Ho, La, Lu, Nd, Pr, Pm, Sm, Sc, Tb, Tm, Yb, Y, alkaline earth metals, Al, Ga, In, Tl, Sn, Pb, Bi and transitional metals, and at least one further metal ion, wherein said further metal ion is selected from the group consisting of rare earth metal ions, transition metal ions, non-transition metal ions and actinide ions;
reacting the mixture of at least one metal ion with at least one compound of general formula (I) to form chelates; and
subjecting the chelates to chromatographic separation;
wherein:

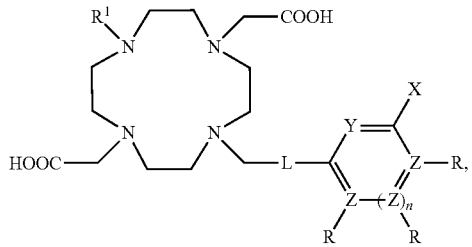
(I)

X is Cl or Br;
Y is nitrogen;
Z atoms are independently selected from the group consisting of carbon and nitrogen, wherein R is only present when the valence of Z allows it; and wherein at least one Z is carbon; and wherein n=0 or 1;
L is a covalent bond or —C(O)—;

each R is independently selected from the group consisting of H; $C_1$ to $C_6$ alkyl; $C_1$ to $C_6$ alkyloxy; $C_6$ to $C_{10}$ aryloxy; benzyloxy; $C_1$ to $C_6$ alkylthio; $C_6$ to $C_{10}$ arylthio; F; Cl; Br; I; OH; SH; $NH_2$; $C_1$ to $C_6$ alkylamino; di($C_1$ to $C_6$ alkyl)amino; $C_1$ to $C_6$ acylamino; di($C_1$ to $C_6$ acyl)amino; $C_6$ to $C_{10}$ arylamino; di($C_6$ to $C_{10}$ aryl)amino; CN; OH; nitro; $COOR_n$; $C(O)NHR_n$; and $C(O)N(R_n)_2$; wherein $R_n$ is independently H or $C_1$ to $C_{10}$ alkyl or $C_6$ to $C_{10}$ aryl;

$R^1$ is selected from the group consisting of H; —$C_1$ to $C_6$ alkyl; benzyl, which can be optionally substituted independently with one or more substituents selected from nitro, OH; —($C_1$ to $C_2$ alkylene) COOH, the alkylene of which can optionally be substituted with $C_1$ to $C_6$ alkyl; —$CH_2P(O)(OH)_2$; —$CH_2P(O)(OH)(C_1$ to $C_6$ alkyl);

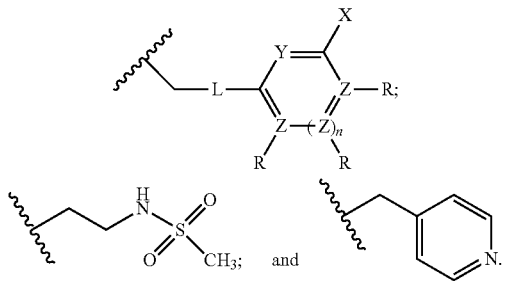

8. The method of chromatographic separation of claim 7, wherein the mixture comprises at least two rare earth metal selected from Ce, Dy, Er, Eu, Gd, Ho, La, Lu, Nd, Pr, Pm, Sm, Sc, Tb, Tm, Yb, and Y.

9. The method of claim 7, wherein the chromatographic separation comprises column chromatography, thin layer chromatography and/or high-performance liquid chromatography, and the metal ions are in a form of salts of organic or inorganic acids, oxides, hydroxides and/or carbonates.

10. The method of claim 7, wherein the contacting the mixture with a solution of the compound of general formula (I) in a molar ratio of metal ions to compound of general formula (I) from 1:0.5 to 1:100.

11. A compound of general formula (Ia),

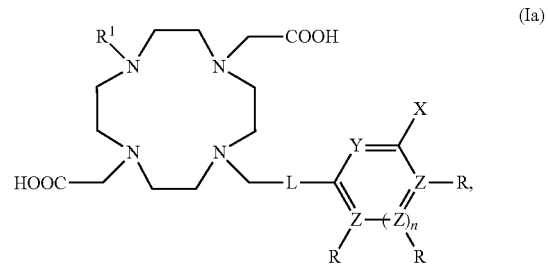
(Ia)

wherein
X is Cl or Br;
Y is nitrogen;
each Z is independently selected from the group consisting of carbon and nitrogen, wherein R is only present when the valence of Z allows it; and wherein at least one Z is carbon; and wherein n=0 or 1;
L is a covalent bond;

at most one Z is other than carbon in each ring of the general formula (Ia), containing Z atoms;

each R is independently selected from the group consisting of H; $C_1$ to $C_{10}$ alkyl; $C_1$ to $C_6$ alkyloxy; $C_6$ to $C_{10}$ aryloxy; benzyloxy; $C_1$ to $C_6$ alkylthio; $C_6$ to $C_{10}$ arylthio; F; Cl; Br; I; OH; SH; $NH_2$; $C_1$ to $C_6$ alkylamino; di($C_1$ to $C_6$ alkyl)amino; $C_1$ to $C_6$ acylamino; di($C_1$ to $C_6$ acyl)amino; $C_6$ to $C_{10}$ arylamino; di($C_6$ to $C_{10}$ aryl)amino; CN; OH; nitro; $COOR_n$; $C(O)NHR_n$; and $C(O)N(R_n)_2$; wherein $R_n$ is independently H or $C_1$ to $C_{10}$ alkyl or $C_6$ to $C_{10}$ aryl;

$R^1$ is selected from the group consisting of H; —$C_1$ to $C_6$ alkyl; benzyl, which can be optionally substituted independently with one or more substituents selected from nitro, and OH; —($C_1$ to $C_2$ alkylenyl)COOH, the alkylenyl of which can be optionally substituted with $C_1$ to $C_6$ alkyl; —$CH_2P(O)(OH)_2$; —$CH_2P(O)(OH)(C_1$ to $C_6$ alkyl);

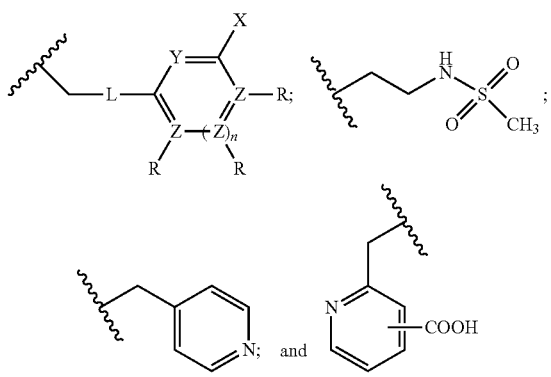

with the proviso that:
when Y is nitrogen, then at most one Z is nitrogen.

12. The compound of claim 11 that is: 2,2',2''-(10-((6-chloropyridin-2-yl)methyl)-1,4,7,10-tetraazacyclododecane-1,4,7-triyl)triacetic acid; 2,2',2''-(10-((6-bromopyridin-2-yl)methyl)-1,4,7,10-tetraazacyclododecane-1,4,7-triyl)triacetic acid; 2,2'-(4-((6-bromopyridin-2-yl)methyl)-10-(2-carboxyethyl)-1,4,7,10-tetraazacyclododecane-1,7-diyl)diacetic acid; 2,2'-(4-(2-carboxyethyl)-10-((6-chloropyridin-2-yl)methyl)-1,4,7,10-tetraazacyclododecane-1,7-diyl)diacetic acid; 2,2'-(4-((6-carboxypyridin-2-yl)methyl)-10-((6-chloropyridin-2-yl)methyl)-1,4,7,10-tetraazacyclododecane-1,7-diyl)diacetic acid; 2,2'-(4-((6-bromopyridin-2-yl)methyl)-10-((6-carboxypyridin-2-yl)methyl)-1,4,7,10-tetraazacyclododecane-1,7-diyl)diacetic acid; 2,2'-(4-((6-chloropyridin-2-yl)methyl)-10-(phosphonomethyl)-1,4,7,10-tetraazacyclododecane-1,7-diyl)diacetic acid; 2,2'-(4-((6-bromopyridin-2-yl)methyl)-10-((hydroxy(methyl)phosphoryl)methyl)-1,4,7,10-tetraazacyclododecane-1,7-diyl)diacetic acid; 2,2'-(4-((6-chloropyridin-2-yl)methyl)-10-((hydroxy(methyl)phosphoryl)methyl)-1,4,7,10-tetraazacyclododecane-1,7-diyl)diacetic acid; 2,2'-(4-(1-carboxyethyl)-10-((6-chloropyridin-2-yl)methyl)-1,4,7,10-tetraazacyclododecane-1,7-diyl)diacetic acid; or 2,2'-(4-((6-chloropyridin-2-yl)methyl)-10-(2-(methylsulfonamido)ethyl)-1,4,7,10-tetraazacyclododecane-1,7-diyl)diacetic acid.

13. The method of claim 3, wherein the mixture of metals is selected from the group consisting of $Ca^{2+}$, $Fe^{2+}$, $Fe^{3+}$, $Co^{2+}$, $Ni^{2+}$, $Cu^{2+}$, $Zn^{2+}$, $Al^{3+}$, $Pb^{2+}$, and $Bi^{3+}$.

14. The method of claim 7, further comprising repeating at least once the subjecting the chelates to chromatographic separation.

15. The method of claim 3 further comprising collecting separated chelates for each metal and adding an acid to decomplex the metal from the chelate.

16. The method of claim 9, wherein the metal ions are in a form of salts of chloride, bromide, sulfate, nitrate, methanesulfonate, trifluoromethanesulfonate, formate, acetate, lactate, malate, citrate, 2-hydroxyisobutyrate, mandelate, diglycolate, tartarate, oxide, hydroxide and/or carbonate.

17. The method of claim 7, wherein the contacting the mixture with a solution of the compound of general formula (I) in a molar ratio of metal ions to compound of general formula (I) from 1:0.5 to 1:100; and wherein the contacting further comprises adding an organic or inorganic base or buffer to the reaction mixture.

18. The compound of claim 11, wherein R is selected from the group consisting of H, F, Cl, Br, I, $CH_3$, $COOR_n$, $C(O)NHR_n$, and $C(O)N(R_n)_2$, and each $R_n$ is independently H or $C_1$ to $C_{10}$ alkyl or $C_6$ to $C_{10}$ aryl.

* * * * *

UNITED STATES PATENT AND TRADEMARK OFFICE
CERTIFICATE OF CORRECTION

PATENT NO. : 12,268,977 B2
APPLICATION NO. : 16/768169
DATED : April 8, 2025
INVENTOR(S) : Miloslav Polasek It is certified that error appears in the above-identified patent and that said Letters Patent is hereby corrected as shown below:

In the Claims

Claim 11, Column 109, Line 4, "$C_1$ to $C_{10}$ alkyl" should read -- $C_1$ to $C_6$ alkyl --.

Signed and Sealed this
Seventeenth Day of June, 2025

Coke Morgan Stewart
*Acting Director of the United States Patent and Trademark Office*